US008840899B2

(12) United States Patent
Ahmed et al.

(10) Patent No.: US 8,840,899 B2
(45) Date of Patent: Sep. 23, 2014

(54) USE OF MTOR INHIBITORS TO ENHANCE T CELL IMMUNE RESPONSES

(75) Inventors: Rafi Ahmed, Atlanta, GA (US);
Christian P. Larsen, Atlanta, GA (US);
Koichi Araki, Atlanta, GA (US)

(73) Assignee: Emory University, Atlanta, GA (US)

( * ) Notice: Subject to any disclaimer, the term of this patent is extended or adjusted under 35 U.S.C. 154(b) by 359 days.

(21) Appl. No.: 13/057,057

(22) PCT Filed: Aug. 5, 2009

(86) PCT No.: PCT/US2009/052886
§ 371 (c)(1),
(2), (4) Date: Feb. 1, 2011

(87) PCT Pub. No.: WO2010/017317
PCT Pub. Date: Feb. 11, 2010

(65) Prior Publication Data
US 2011/0129496 A1    Jun. 2, 2011

Related U.S. Application Data

(60) Provisional application No. 61/086,350, filed on Aug. 5, 2008.

(51) Int. Cl.
*A61K 39/12* (2006.01)
*A61K 39/02* (2006.01)
*A61K 39/002* (2006.01)
*G01N 33/50* (2006.01)
*C07K 14/005* (2006.01)
*A61K 45/06* (2006.01)
*A61K 39/39* (2006.01)
*A61K 31/4745* (2006.01)
*A61K 39/00* (2006.01)

(52) U.S. Cl.
CPC ........... *A61K 31/4745* (2013.01); *C07K 14/005* (2013.01); *A61K 39/12* (2013.01); *C12N 2740/13013* (2013.01); *A61K 45/06* (2013.01); *A61K 2039/55561* (2013.01); *A61K 2039/53* (2013.01); *C12N 2730/10134* (2013.01); *A61K 2039/55516* (2013.01); *C12N 2760/10034* (2013.01); *A61K 39/39* (2013.01); *C12N 2770/10022* (2013.01); *A61K 2039/5258* (2013.01); *C12N 2710/10343* (2013.01); *C12N 2710/24122* (2013.01)
USPC .................. 424/184.1; 424/204.1; 424/234.1; 424/265.1; 424/274.1; 424/277.1; 435/7.24

(58) Field of Classification Search
None
See application file for complete search history.

(56) References Cited

U.S. PATENT DOCUMENTS

| 2005/0180951 A1 | 8/2005 | Ohno |
| 2006/0127357 A1* | 6/2006 | Roncarolo et al. ........... 424/85.2 |
| 2008/0044405 A1 | 2/2008 | Dedecker et al. |
| 2008/0131445 A1 | 6/2008 | Bluestone et al. |

FOREIGN PATENT DOCUMENTS

| WO | 2006/090291 | 8/2006 | |
| WO | WO 2006090291 A2 * | 8/2006 | ............... C12N 5/00 |
| WO | 2007/124252 | 11/2007 | |

OTHER PUBLICATIONS

Kang et al. De novo induction of antigen-specific CD4+CD25+Foxp3+ regulatory T cells in vivo following systemic antigen administration accompanied by blockade of mTOR. Journal of Leukocyte Biology, May 2008, vol. 83, pp. 1230-1239.*
Gonzalez J et al: Rapamycin blocks IL-2-driven T cell cycle progression while preserving T cell survival Blood Cells, Molecules & Diseases vol. 27, No. 3, May 2001, pp. 572-585.
Uemura et al: Tumor vaccines in renal cell carcinoma World Journal of Urology, vol. 26, No. 2, Mar. 12, 2008 pp. 147-154.
Ha S-J et al Manipulating both the inhibitory and stimulatory immune system towards the success of therapeutic vaccination against chronic viral infections Immunological Reviews, vol. 223, No. 1, 2008 pp. 317-333.
Holger et al Impact of immunosuppressive drugs on adaptive and innate immune responses to Aspergillus fumigatus antigens Blood, American Society of Hematology, vol. 104, No. 11, Part I 2004 p. 611A.
Kang J et al. De novo induction of antigen-specific CD4+CD25+Foxp3+ regulatory T cells in vivo following systemic antigen administration accompanied by blockade of mTOR., J Leukoc Biol., vol. 83, No. 5, 2008 pp. 1230-1239.
Sardella G et al. Altered trafficking of CD8+ memory T cells after implantation of rapamycin-eluting stents in patients with coronary artery disease., Immunol Lett., vol. 96, No. 1, 2005, pp. 85-91.
Sharma D et al. Differential modulation of mitogen driven proliferation and homeostasis driven proliferation of T cells by rapamycin, Ly294002 and chlorophyllin. Mol. Immunol., vol. 44, No. 11, 2007, pp. 2831-2840.
Araki K., et al. mTOR regulates memory CD8 T-cell differentiation, NATURE., vol. 460, No. 7251, 2009, pp. 108-112.

(Continued)

*Primary Examiner* — Louise Humphrey
(74) *Attorney, Agent, or Firm* — Emory Patent Group

(57) ABSTRACT

It is disclosed herein that treatment of a subject with an mTOR inhibitor enhances antigen-specific T cell immune responses. Thus, provided herein is a method of enhancing an antigen-specific T cell response in a subject by administering to the subject a therapeutically effective amount of an mTOR inhibitor. The antigen can be any antigen, such as an antigen from a pathogen or a vaccine, or a tumor antigen. In some embodiments, the method further comprises administering to the subject a vaccine, such as a virus vaccine or a cancer vaccine. The mTOR inhibitor can be administered either before or after vaccination to enhance the quantity and quality of the T cell immune response and immunological memory. In some examples, the mTOR inhibitor is rapamycin or a rapamycin analog.

13 Claims, 26 Drawing Sheets

(56) References Cited

OTHER PUBLICATIONS

Araki, K., et al., Tor in the immune System, Curr Opin Cell Biol. Dec. 2011; 23(6): 707-715.

Araki, K., et al., The role of mTOR in memory CD8 T-cell differentiation. Immunol Rev. May 2010; 235(1):234-43.

Cao, W., et al., Toll-like receptor-mediated induction of type I interferon in plasmacytoid dendritic cells requires the rapamycin-sensitive PI(3)K-mTOR-p7OS6K pathway, 2008 Nat Immunol 9(10): 1157-1164.

Sauer S. et al. T cell receptor signaling controls Foxp3 expression via PI3K, Akt, and mTOR. Proc. Natl Acad. Sci. USA 105,7797-7802 (2008).

Haxhinasto, S., et al., the AKT-mTOR axis regulates de novo differentiation of CD4+Foxp3+ cells, 2008, J Exp Med 205:565-574.

Weichart, T., et al. The TSC-mTOR signaling pathway regulates the innate inflammatory response. Immunity 29, 565-577 (2008).

Ohtani, M., et al., Mammalian target of rapamycin and glycogen synthase kinase 3 differentially regulate lipopolysaccharide-induced interleukin-12 production in dendritic cells, 2008, Blood 112:635-643.

Williams, M., et al., Effector and Memory CTL Differentiation, 2007, Annu Rev Immunol 25: 171-192.

Kaech, S., et al., Heterogeneity and cell-fate decisions in effector and memory CD8+ T cell differentiation during viral infection, 2007 Immunity 27,393-405.

* cited by examiner

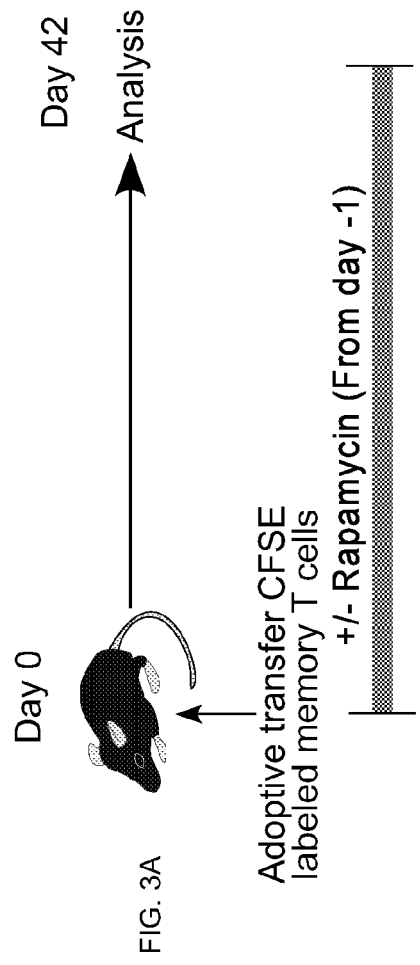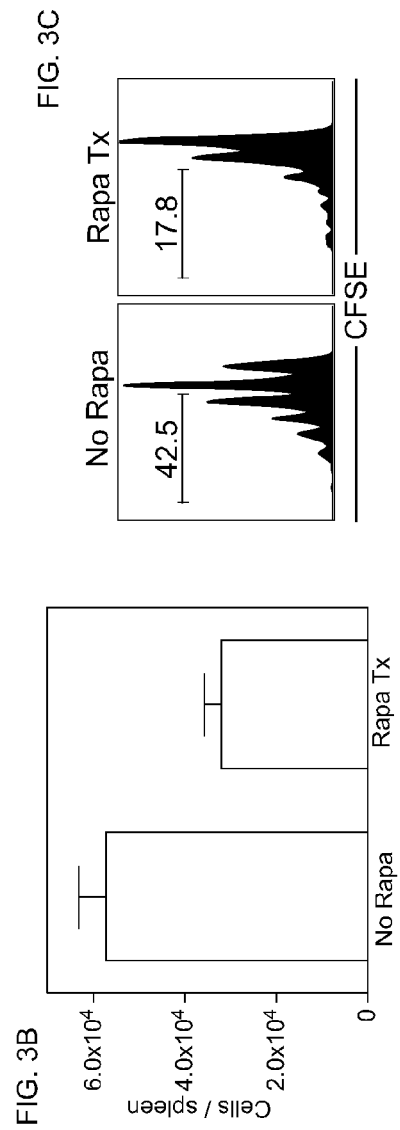

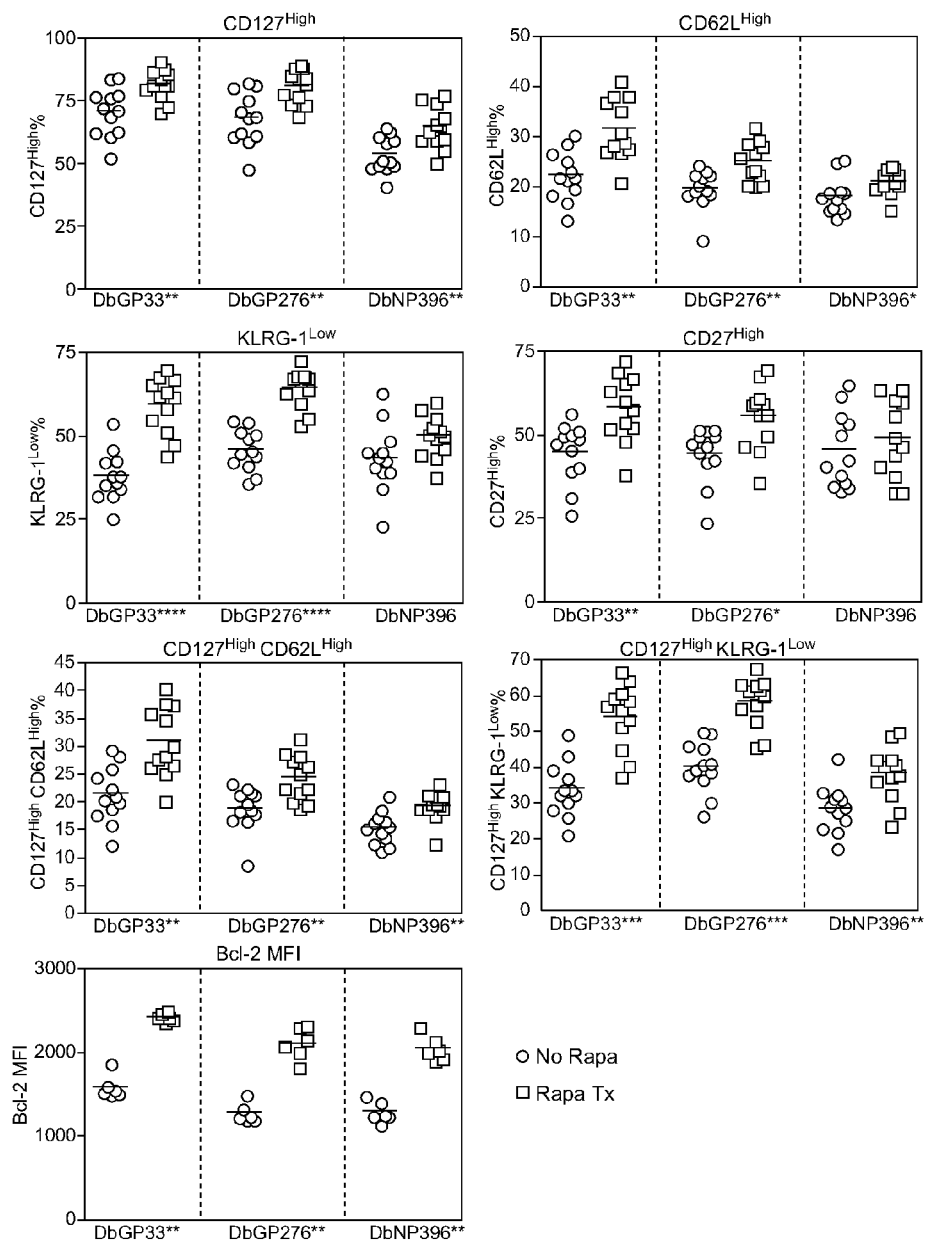

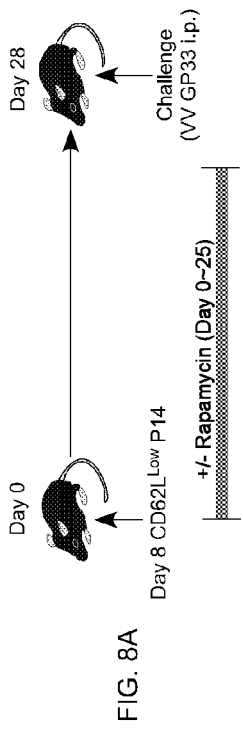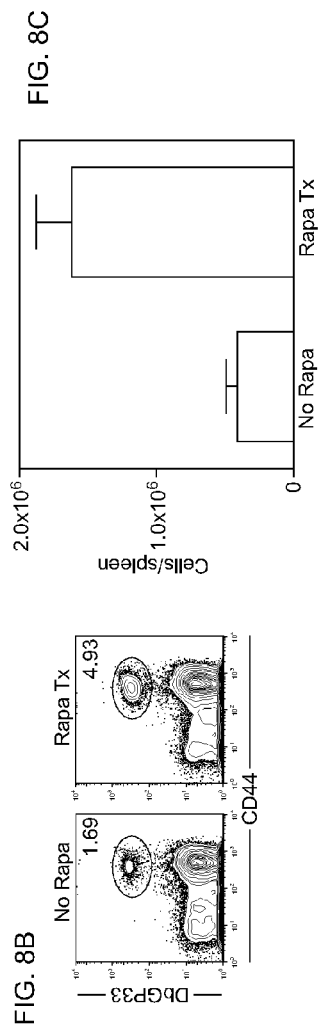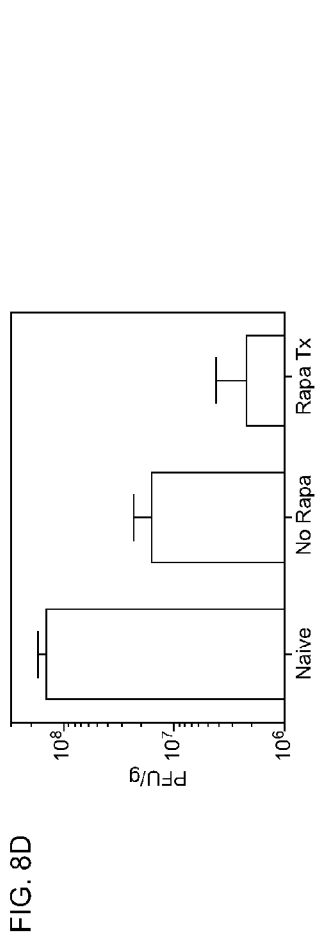

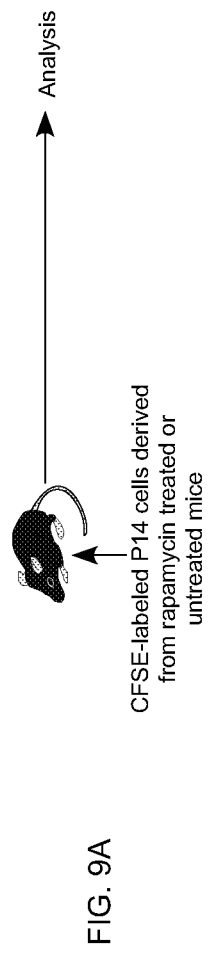
FIG. 9A
FIG. 9B
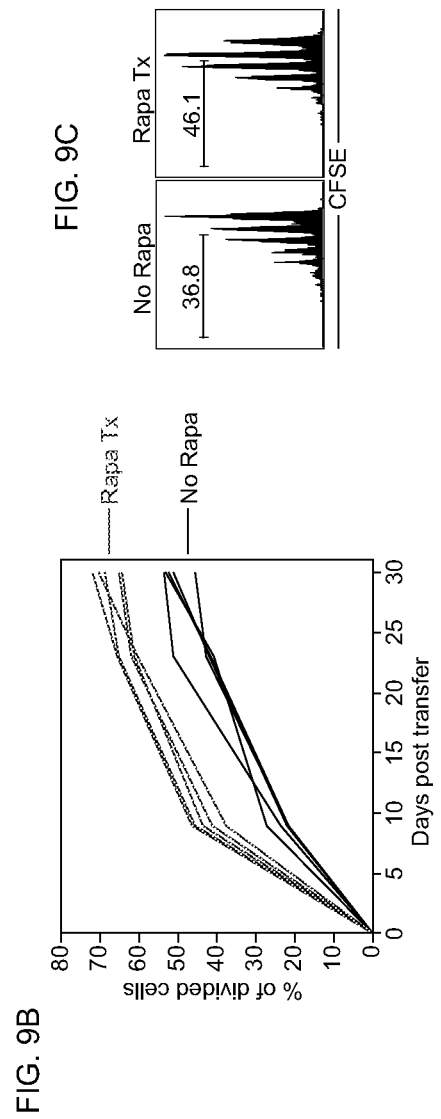
FIG. 9C

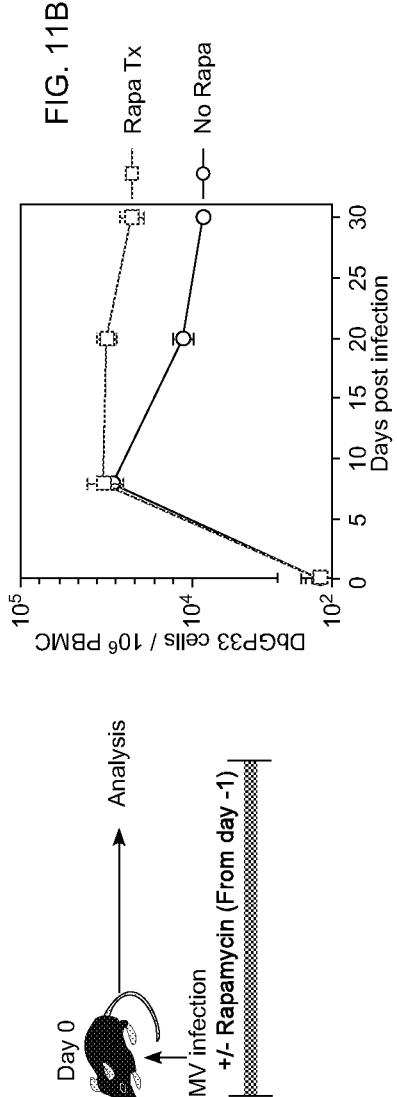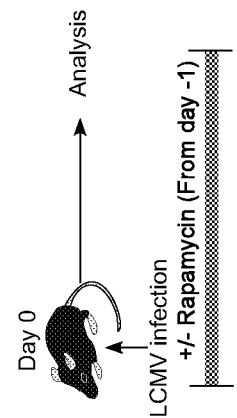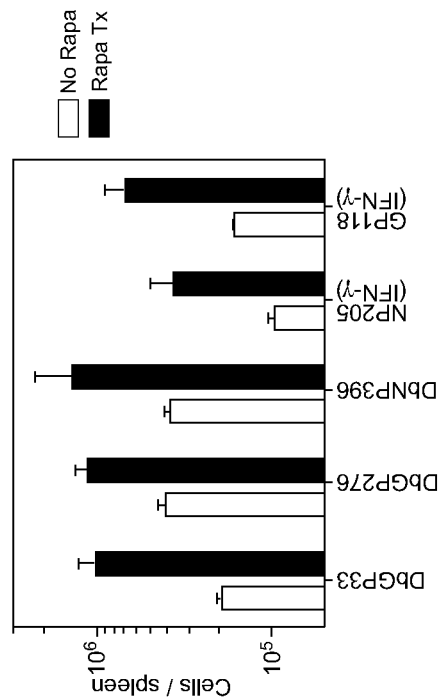
FIG. 11A
FIG. 11B
FIG. 11C

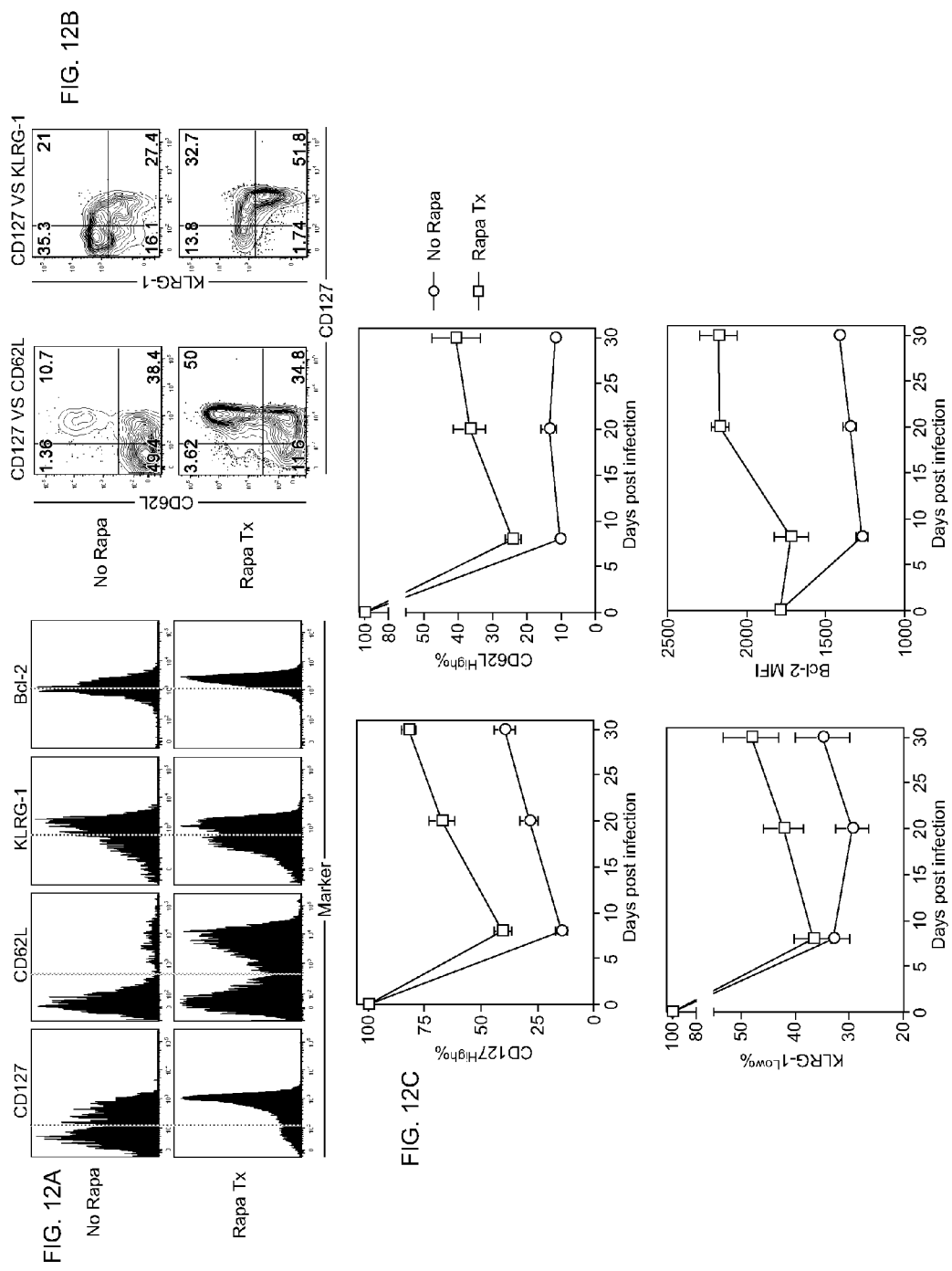

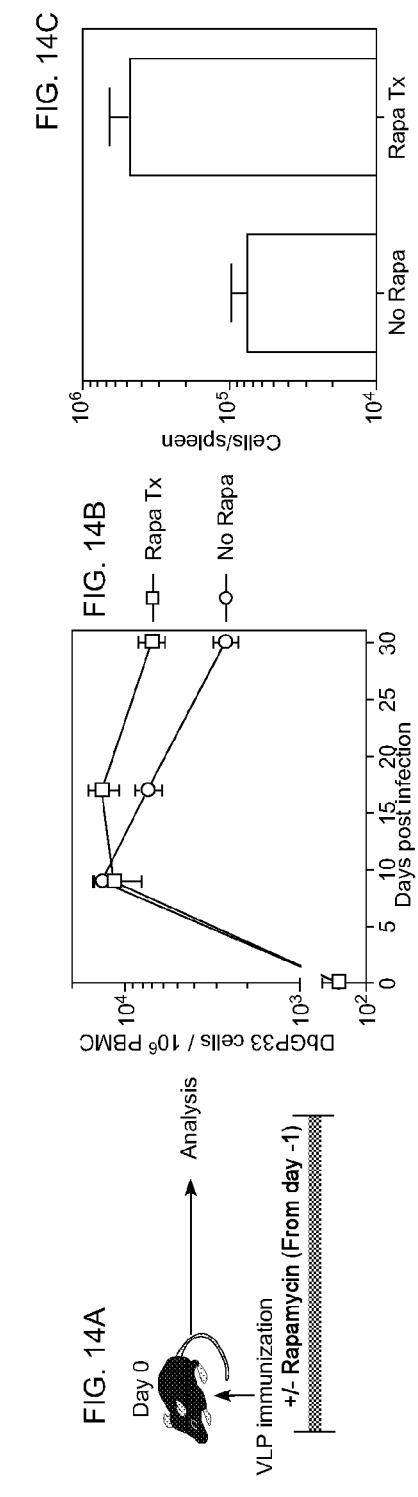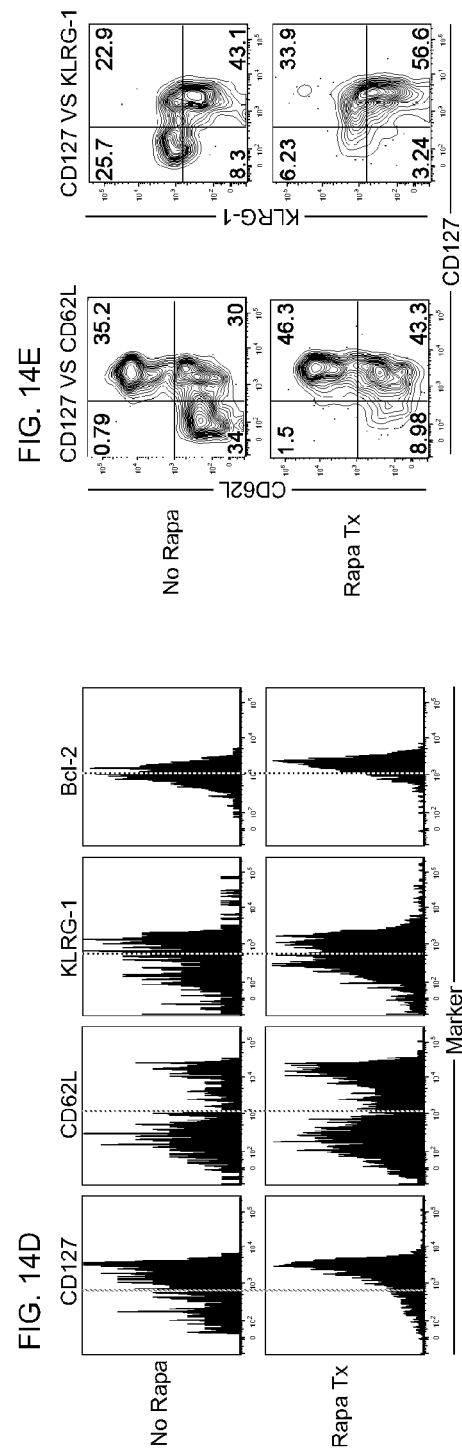

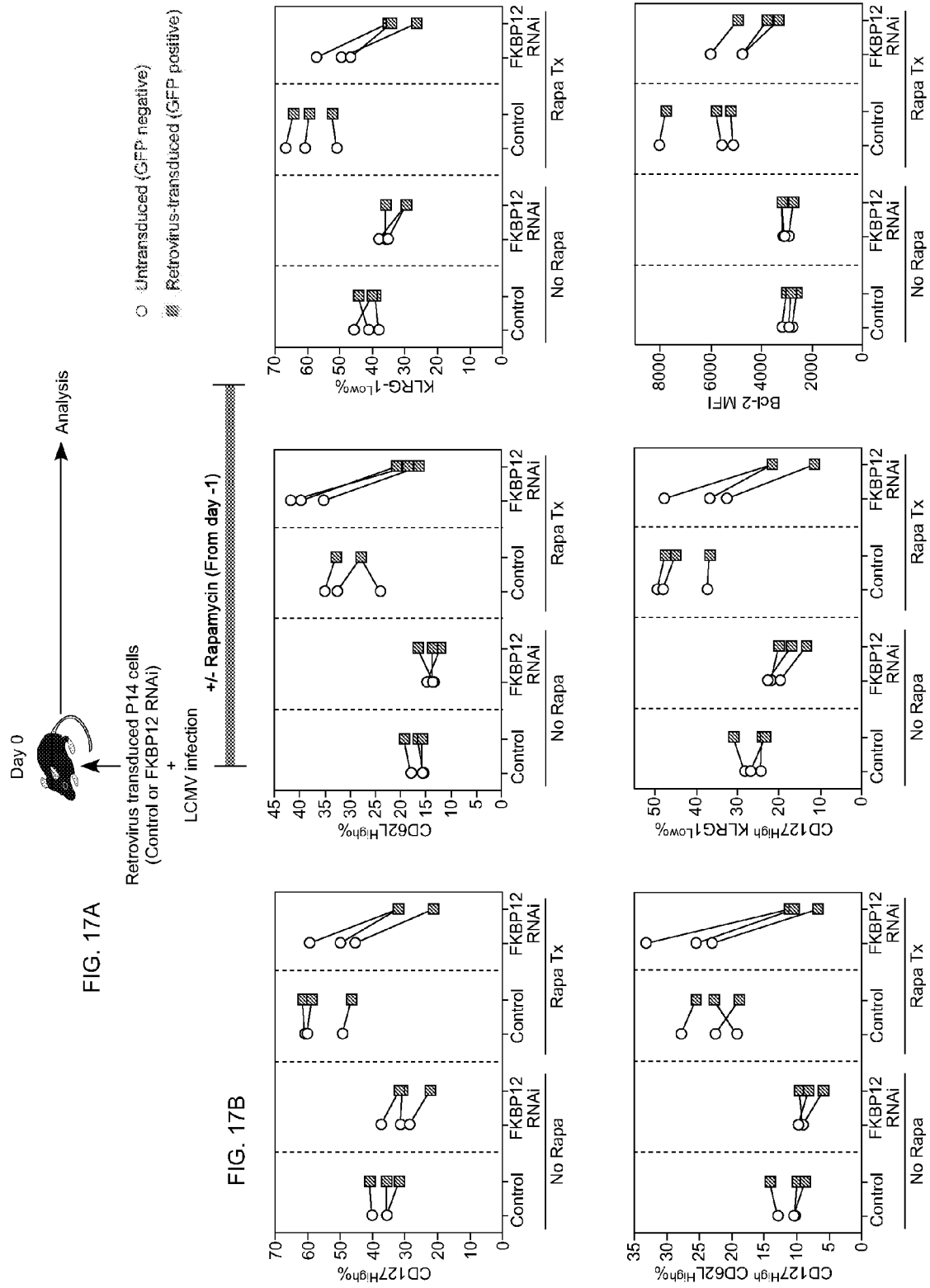

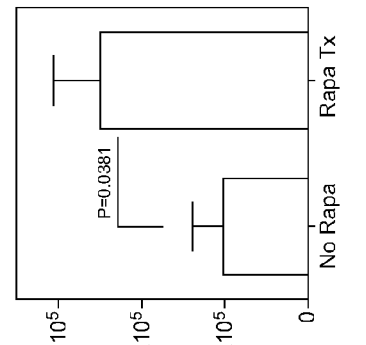
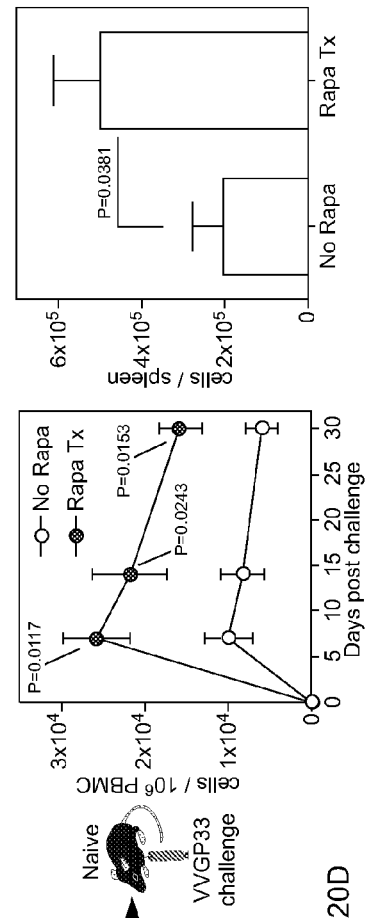
FIG. 20B
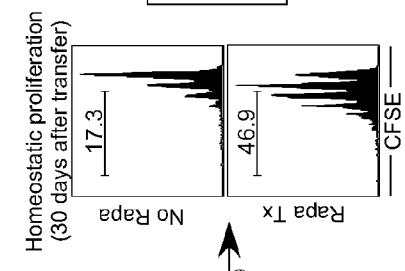
FIG. 20D
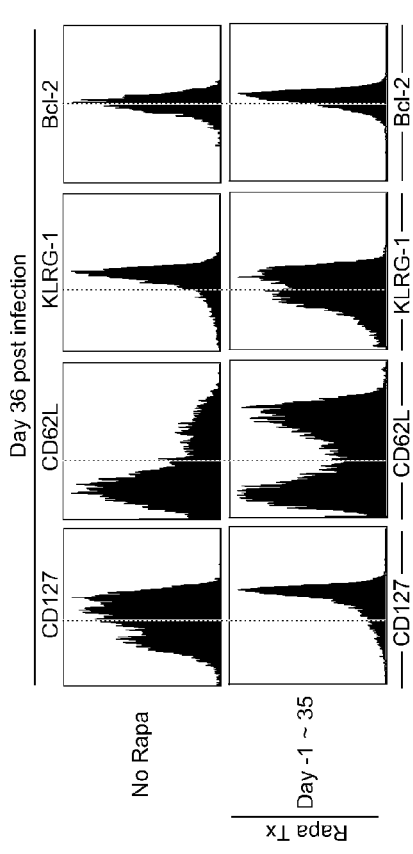
FIG. 20A
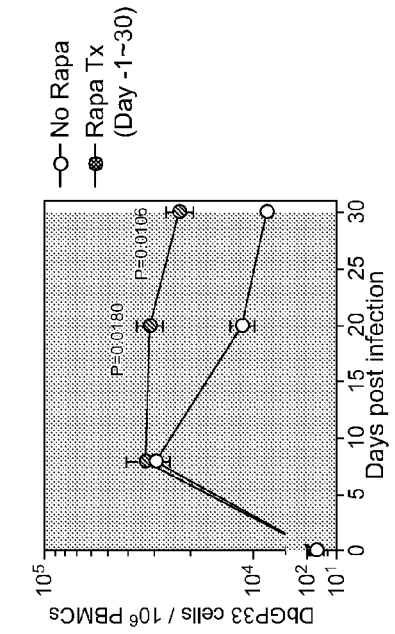
FIG. 20C

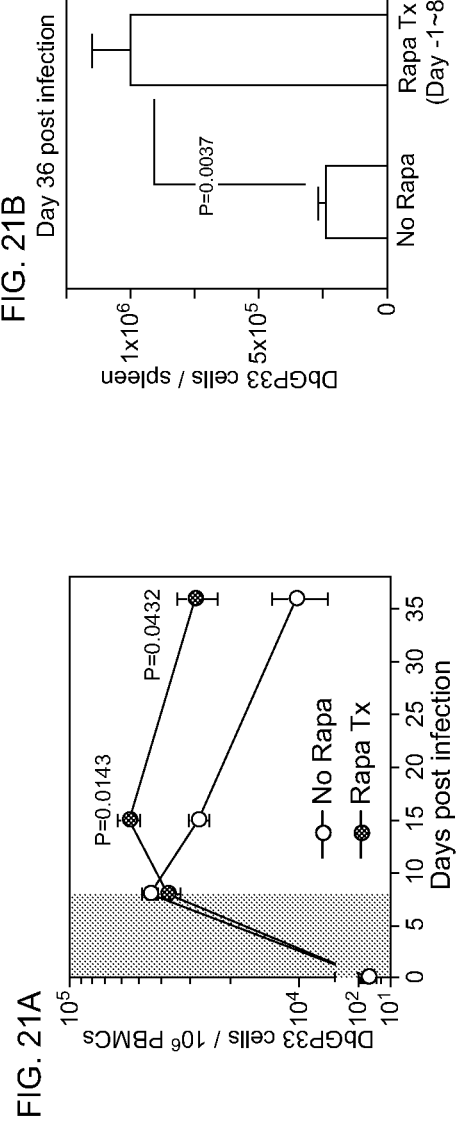
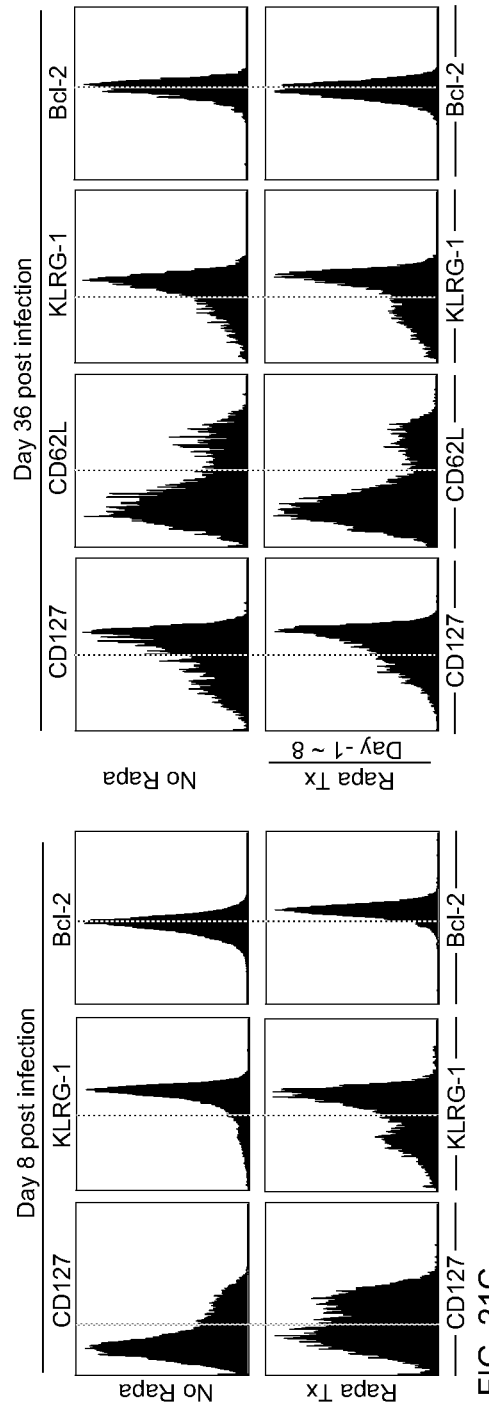

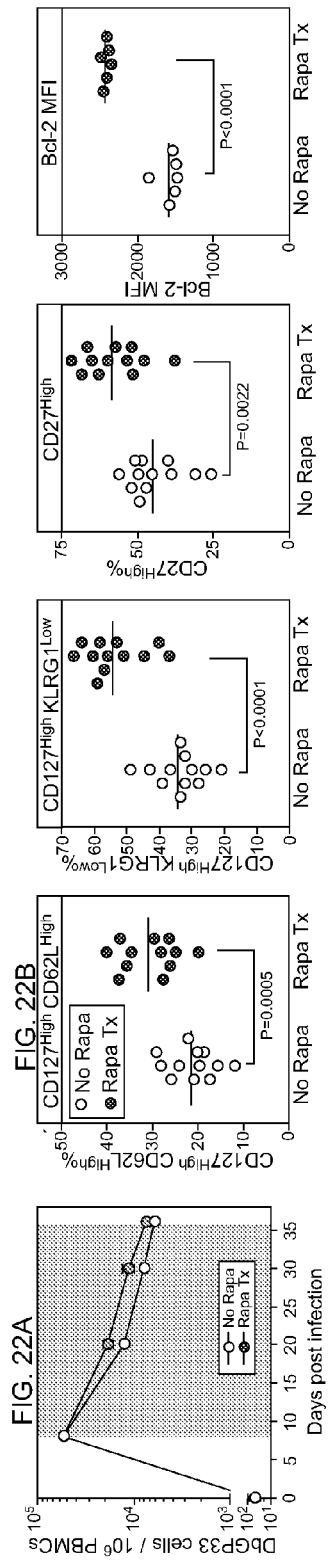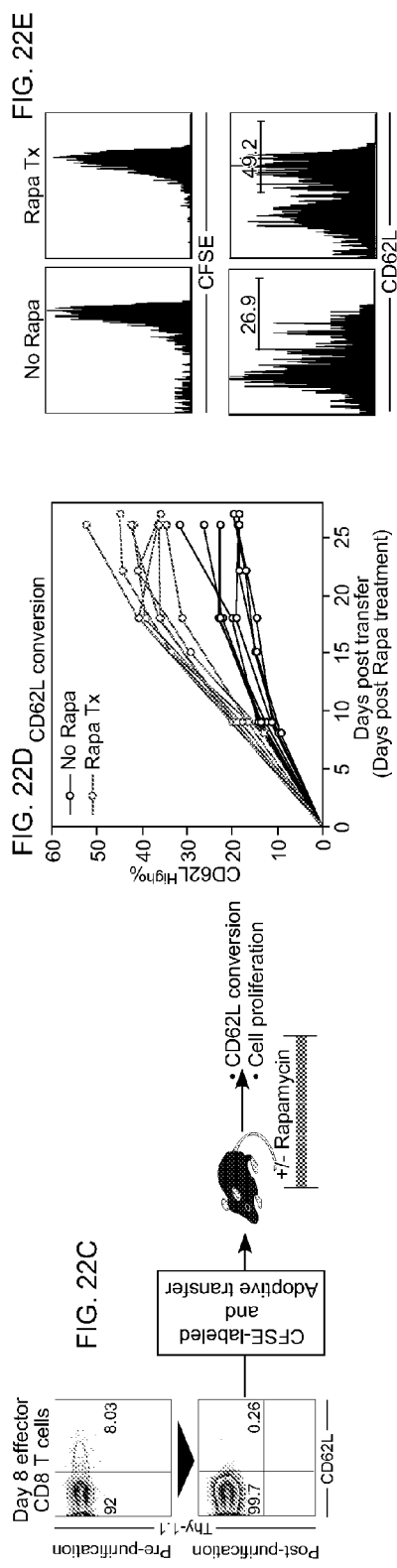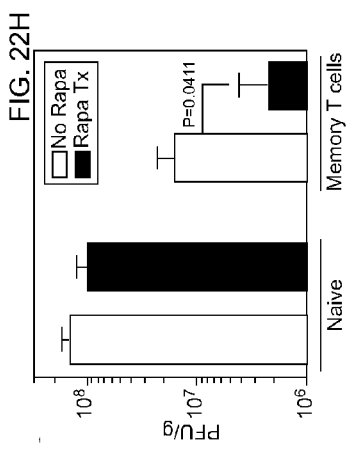

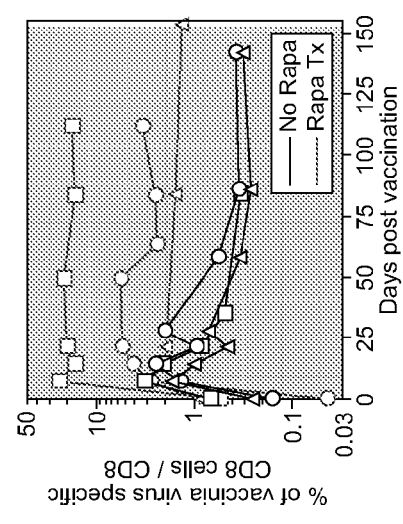
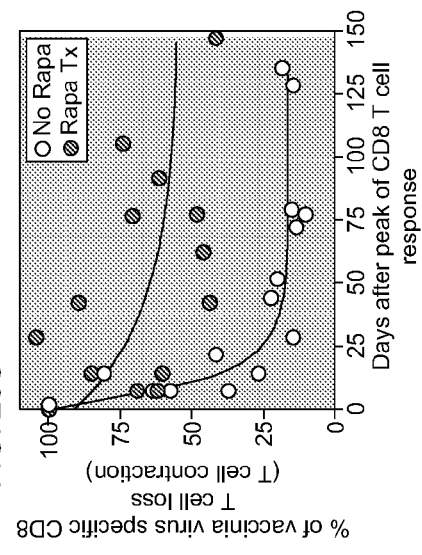
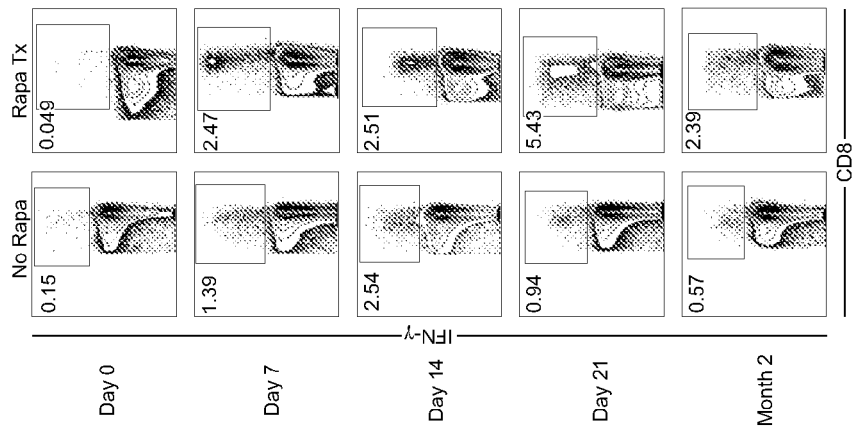
FIG. 25A
FIG. 25B
FIG. 25C

USE OF MTOR INHIBITORS TO ENHANCE T CELL IMMUNE RESPONSES

CROSS REFERENCE TO RELATED APPLICATION

This application claims the benefit of U.S. Provisional Application No. 61/086,350, filed Aug. 5, 2008, which is herein incorporated by reference in its entirety.

STATEMENT OF GOVERNMENT SUPPORT

This invention was made with government support under grant numbers 5R37AI030048 and 5P01AI044644 awarded by the National Institutes of Health. The government has certain rights in the invention.

FIELD

This disclosure concerns the use of mammalian target of rapamycin (mTOR) inhibitors, such as rapamycin or analogs thereof, to enhance T cell immune responses.

BACKGROUND

Mammalian target of rapamycin (mTOR) is a serine/threonine protein kinase known to play a role in regulating cell growth, cell proliferation, cell motility, cell survival, protein synthesis and transcription. Dysregulation of the mTOR pathway is implicated as a contributing factor to various human diseases, particularly various types of cancer. Rapamycin is a natural product produced by the bacterium *Streptomyces hygroscopicus* that can inhibit mTOR through association with its intracellular receptor FK-506 binding protein 12 (FKBP12). The FKBP12-rapamycin complex binds directly to the FKBP12-rapamycin binding domain of mTOR.

It has been demonstrated that mTOR functions as a catalytic subunit for two distinct molecular complexes, mTOR complex 1 (mTORC1) and mTOR complex 2 (mTORC2). In addition to mTOR, mTORC1 is composed of regulatory associated protein of mTOR (Raptor) and mammalian LST8/G-protein β-subunit like protein (mLST8/GβL). This complex functions as a nutrient/energy/redox sensor and plays a role in regulating protein synthesis. The activity of mTORC1 is stimulated by insulin, growth factors, serum, phosphatidic acid, amino acids (particularly leucine) and oxidative stress (Hay and Sonenberg, *Genes Dev.* 18(16):1926-1945, 2004; Wullschleger et al., *Cell* 124(3):471-484). In contrast, mTORC1 is known to be inhibited by low nutrient levels, growth factor deprivation, reductive stress, caffeine, rapamycin, farnesylthiosalicylic acid and curcumin (Beevers et al., *Int. J. Cancer* 119(4):757-764, 2006; McMahon et al., *Mol. Endocrinol.* 19(1):175-183). The components of mTORC2 are rapamycin-insensitive companion of mTOR (Rictor), GβL, mammalian stress-activated protein kinase interacting protein 1 and mTOR. mTORC2 has been shown to function as an important regulator of the cytoskeleton through its stimulation of F-actin stress fibers, paxillin, RhoA, Rac1, Cdc42 and protein kinase C alpha (Sarbassov et al., *Curr. Biol.* 14(14): 1296-302, 2004; Sarbassov et al., *Science* 307(5712): 1098-101, 2005). Unlike mTORC1, mTORC2 is not sensitive to rapamycin.

A number of mTOR inhibitors are currently being used, or are currently being investigated in clinical trials, to treat a variety of conditions Inhibitors of mTOR, such as rapamycin, are known to exhibit immunosuppressive and anti-proliferative properties. Accordingly, mTOR inhibitors are routinely administered to transplant recipients to prevent organ or bone marrow rejection.

Vaccines are widely used to treat or prevent disease, including infectious disease and cancer. In order for a vaccine to be effective, sufficient immunological memory against the target pathogen or cancer must be elicited, which often requires more than one dose of vaccine. The ability to induce adequate immunological memory in a subject by administration of a single vaccine dose is desirable to achieve rapid vaccination, as well as to reduce cost and improve compliance. Thus, a need remains for methods of enhancing immune responses against candidate vaccines.

SUMMARY

As disclosed herein, mTOR inhibitors have surprisingly been demonstrated to enhance antigen-specific T cell immune responses, which are critical for establishing immunity. To enhance antigen-specific T cell immune responses in a subject exposed to an antigen, an mTOR inhibitor is administered during the contraction phase of a T cell response, or the inhibitor is administered at any time prior to or subsequent to antigen challenge when administered at a low dose.

Provided herein is a method of enhancing an antigen-specific T cell response in a subject by administering to the subject a therapeutically effective amount of an antigen and a therapeutically effective amount of an mTOR inhibitor, thereby enhancing an antigen-specific T cell immune response in the subject. In some embodiments, enhancing an antigen-specific T cell response in a subject includes increasing the number or quality of antigen-specific T cells in the subject. In some embodiments, the antigen is part of a vaccine. The antigen can be any antigen, including, but not limited to, an antigen from a pathogen, such as a virus, bacteria, fungus or parasite, or a tumor antigen.

Also provided is a method of increasing the proportion of antigen-specific $CD127^{High}KLRG-1^{Low}$ $CD8^+$ T cells in a subject by administering to the subject a therapeutically effective amount of an antigen and an mTOR inhibitor. Further provided is a method of increasing expression of CD127, CD62L, Bcl-2 and CD27, and decreasing expression of KLRG-1, in CD8+ T cells of a subject by administering to the subject an antigen and an mTOR inhibitor.

The foregoing and other features and advantages will become more apparent from the following detailed description of several embodiments, which proceeds with reference to the accompanying figures.

BRIEF DESCRIPTION OF THE FIGURES

FIG. 3A is a schematic of the experimental design for testing the effect of rapamycin treatment on virus-specific CD8+ T cells during the maintenance phase. Carboxyfluorescein succinimidyl ester (CFSE)-labeled GP33-epitope specific memory CD8+ T cells were adoptively transferred into mice on Day 0. Mice were treated with rapamycin every day starting one day prior to adoptive transfer (Day −1). Splenocytes from untreated and rapamycin-treated mice were analyzed on Day 42. FIG. 3B is a graph showing the number of virus-specific CD8+ T cells in the spleen of untreated and rapamycin-treated mice on Day 42. FIG. 3C shows FACS plots of CFSE-labeled virus-specific CD8+ T cells obtained from untreated and rapamycin-treated mice on Day 42 post-transfer. The percentage of adoptively transferred cells that divided more than twice is indicated.

FIG. 5B is a series of graphs that summarizes the phenotype of DbGP33, DbGP276 and DbNP396 tetramer-positive CD8+ T cells.

FIG. 8A is a schematic of the experimental design for evaluating protective immunity by rapamycin-induced memory CD8+ T cells. CD62L$^{Low}$ LCMV-specific Day 8 effector P14 cells were transferred into naïve mice on Day 0 and mice were treated with rapamycin for 25 days. Mice were challenged with vaccinia virus (VV) GP33 on Day 28. FIG. 8B shows FACS plots of splenocytes obtained from untreated and rapamycin-treated mice on Day 5 post-challenge. The percentage of DbGP33 tetramer-positive P14 cells is indicated. FIG. 8C is a graph showing the number of DbGP33 tetramer-positive P14 cells in the spleen of untreated and rapamycin-treated mice on Day 5 post-challenge. FIG. 8D is a graph showing viral titer in the ovaries (PFU/gram) of naïve, untreated and rapamycin-treated mice on Day 5 post-challenge.

FIG. 9A is a schematic of the experimental design for evaluating homeostatic proliferation of rapamycin-induced memory CD8+ T cells. CFSE-labeled P14 memory cells derived from rapamycin-treated or untreated mice were adoptively transferred into naïve mice and analyzed up to 30 days post-transfer. FIG. 9B is a graph showing the percentage of divided P14 memory cells in PBMC over time. FIG. 9C shows FACS plots of CFSE-labeled CD8+ T cells obtained from the spleen of untreated and rapamycin-treated mice on Day 30 post-transfer. The percentage of P14 cells that divided more than twice is indicated.

FIG. 11A is a schematic of the experimental design to demonstrate that low dose rapamycin treatment enhances the number of virus-specific CD8+ T cells. Rapamycin treatment was initiated one day prior to infection with LCMV. FIG. 11B is a graph showing the number of DbGP33 tetramer-positive LCMV-specific CD8+ T responses in PBMC obtained from untreated and rapamycin-treated mice up to 30 days post-infection. FIG. 11C is a graph showing the number of virus-specific CD8+ T cells in the spleen of untreated and rapamycin-treated mice at Day 35. Tetramer staining was used to detect GP33, GP276 and NP396 epitope-specific CD8+ T cells, while CD8+ T cells specific for epitopes NP205 and GP118 were detected by IFN-γ staining following peptide stimulation.

FIG. 12A is a series of FACS plots showing phenotypic changes (expression of CD127, CD62L, KLRG-1 and Bcl-2) of virus-specific CD8+ T cells obtained from the spleen of untreated and rapamycin-treated mice on Day 35 post-infection. FIG. 12B is a series of FACS plots showing the percentage of virus-specific CD8+ T cells co-expressing CD127 and either CD62L or KLRG-1. FIG. 12C is a series of graphs showing the kinetics of phenotypic changes of DbGP33 tetramer-positive LCMV-specific CD8+ T cells in PBMC obtained from untreated and rapamycin-treated mice at intervals from Day 0 to Day 30.

FIG. 14A is a schematic of the experimental design to demonstrate that low dose rapamycin treatment induces high quality memory T cells upon immunization with virus-like particles (VLPs). Rapamycin treatment was initiated one day prior to immunization with VLPs. FIG. 14B is a graph showing DbGP33 tetramer-positive CD8+ T cell responses in PBMCs obtained from untreated and rapamycin-treated mice. FIG. 14C is a graph showing the number of DbGP33 tetramer-positive CD8+ T cells obtained from the spleen of untreated and rapamycin-treated mice on Day 34 post-infection. FIGS. 14D and 14E are FACS plots showing the phenotypic analysis of DbGP33 tetramer-positive CD8+ T cells in the spleen on Day 34 post-immunization.

FIG. 17A is a schematic of the experimental design to demonstrate that LCMV-specific CD8+ T cells become rapamycin sensitive after FKBP12 knockdown. Control or FKBP12 RNAi retrovirus transduced LCMV-specific P14 cells were adoptively transferred into naïve mice and the mice were infected with LCMV. Rapamycin treatment was initiated on the day prior to LCMV infection (Day −1). FIG. 17B is a series of graphs showing the phenotypic changes of adoptively transferred P14 cells on Day 16 post-LCMV infection in PBMC. Green fluorescent protein (GFP)-positive cells are retrovirus-transduced cells.

FIG. 20A is a graph showing the kinetics of endogenous GP33 epitope-specific CD8+ T cells in PBMCs of LCMV-infected B6 mice treated with rapamycin from Day −1 to Day 30 post-infection (shaded area) (No Rapa, n=3 mice; Rapa Tx, n=6). FIG. 20B is a series of FACS plots showing phenotypic analysis of endogenous DbGP33 tetramer-positive cells in the spleen at Day 36 post infection. FIG. 20C is schematic diagram and pair of FACS plots showing GP33 epitope-specific P14 transgenic memory CD8+ T cells (Day 34 post-infection) were generated in the presence or absence of rapamycin, labeled with CFSE and then adoptively transferred into naïve mice to monitor their homeostatic proliferation. CFSE dilution of P14 cells at 30 days post transfer is shown in the FACS plots and the number represents percentage of memory cells that divided more than two times. FIG. 20D is a schematic diagram and a pair of graphs showing that memory P14 cells derived from rapamycin-treated or untreated mice were adoptively transferred and mice were challenged with vaccinia virus expressing the GP33 epitope (VVGP33). Kinetics of P14 cells in PBMCs after challenge (left graph) and the total P14 cell numbers in spleen on Day 30 post-infection (right graph) are shown (No Rapa, n=4; Rapa Tx, n=6). Error bars indicate standard error of the mean (SEM).

FIG. 21A is a graph showing kinetics of endogenous GP33 epitope-specific CD8+ T cells in PBMCs of LCMV-infected B6 mice treated with rapamycin from Day −1 to Day 8 post-infection (shaded area) (n=3-6 for each time point). FIG. 21B is a graph showing the average number of DbGP33 tetramer-positive cells on Day 36 post-infection in spleens of LCMV-infected mice treated with rapamycin (No Rapa, n=9; Rapa Tx Day −1 to Day 8, n=3). FIG. 21C is a series of FACS plots showing CD127, KLRG-1, and Bcl-2 expression on endogenous DbGP33 tetramer-positive cells in PBMCs at 8 days post-LCMV infection in B6 mice. Rapamycin was administered from Day −1 to Day 8 post-infection. FIG. 21D is a series of FACS plots showing phenotypic analysis of DbGP33 tetramer-positive cells in spleens of LCMV-infected mice (rapamycin treatment from Day −1 to Day 8 post-infection). Error bars indicate SEM.

FIG. 22A is a graph showing kinetics of endogenous GP33 epitope-specific CD8+ T cells in PBMCs of LCMV-infected B6 mice treated with rapamycin from Day 8 to Day 36 post-infection (shaded area) (No Rapa, n=9 mice; Rapa Tx, n=9). FIG. 22B is a series of graphs showing phenotypic changes in endogenous DbGP33 tetramer-positive CD8+ T cells in the spleen on Day 36 post-LCMV infection (n=12 for each group). B6 Mice were treated with rapamycin during the effector to memory T cell transition period (Days 8-35 post-infection). FIG. 22C is a pair of FACS plots and a schematic diagram showing CD62L-negative Day 8 P14 transgenic effector CD8+ T cells were purified, labeled with CFSE, and then adoptively transferred into naïve mice. Half of these mice were treated with rapamycin after transfer and CD62L conversion in the antigen-specific CD8+ T cells was analyzed longitudinally in the blood (FIG. 22D). FIG. 22E is a series of FACS plots showing CFSE profile and CD62L expression on antigen-specific memory CD8+ T cells in the spleen at Day 27 after transfer of CD62L-negative effector T cells. FIG. 22F is a schematic diagram showing CD62L-negative Day 8 P14 transgenic effector CD8+ T cells were adoptively transferred into naïve mice. These mice were treated with rapamycin for 25 days, and were challenged with VVGP33 on Day 28 post-transfer. At 5 days after challenge, P14 expansion in spleen (FIG. 22G) and viral titers in ovary (FIG. 22H) were analyzed (n=4-6 for each group). Flow data were gated on CD8+ T cells. Error bars indicate SEM.

FIGS. 23A and 23B are a series of graphs showing changes in expression of phenotypic markers following mTOR (A) or raptor (B) RNAi treatment. Each line shows expression of the indicated phenotypic markers on transduced and non-transduced antigen-specific CD8+ T cells in individual animals. The same control data are shown in A and B. FIG. 23C is a series of graphs showing changes in expression of phenotypic markers following FKBP12 RNAi treatment. FKBP12 RNAi expressing retrovirus- or control retrovirus-transduced P14 transgenic CD8+ T cells (marked by GFP expression) were adoptively transferred into naïve mice, followed by LCMV infection. Half of the mice were treated with rapamycin throughout infection. Phenotypic analysis of retrovirus-transduced cells (GFP+) and non-transduced (GFP−) P14 cells in the PBMCs was performed on Days 14-16 post-infection.

FIGS. 25A-25C demonstrate that mTOR regulates memory CD8+ T cell responses in non-human primates. Rhesus macaques were vaccinated with MVA (booster immunization) in the presence or absence of rapamycin (n=3 for each group). PBMCs from vaccinated macaques were stimulated with vaccinia virus and analyzed for IFN-γ production. FIG. 25A is a series of FACS plots analyzing IFN-γ production from representative macaques (gated on CD3+CD8+ cells). FIG. 25B is a graph showing kinetics of IFN-γ producing vaccinia virus-specific CD8+ T cells in individual animals. The shaded area shows rapamycin treatment. FIG. 25C is a graph showing IFN-γ producing vaccinia virus-specific CD8+ T cell contraction rate over time. The number of vaccinia virus-specific CD8+ T cells at the peak between days 7-21 post-vaccination was taken as 100% for individual animals, and contraction rate was calculated as a percentage of this peak response. Lines and shaded area show nonlinear regression (one phase exponential decay) and rapamycin treatment, respectively.

SEQUENCE LISTING

Figure 1:
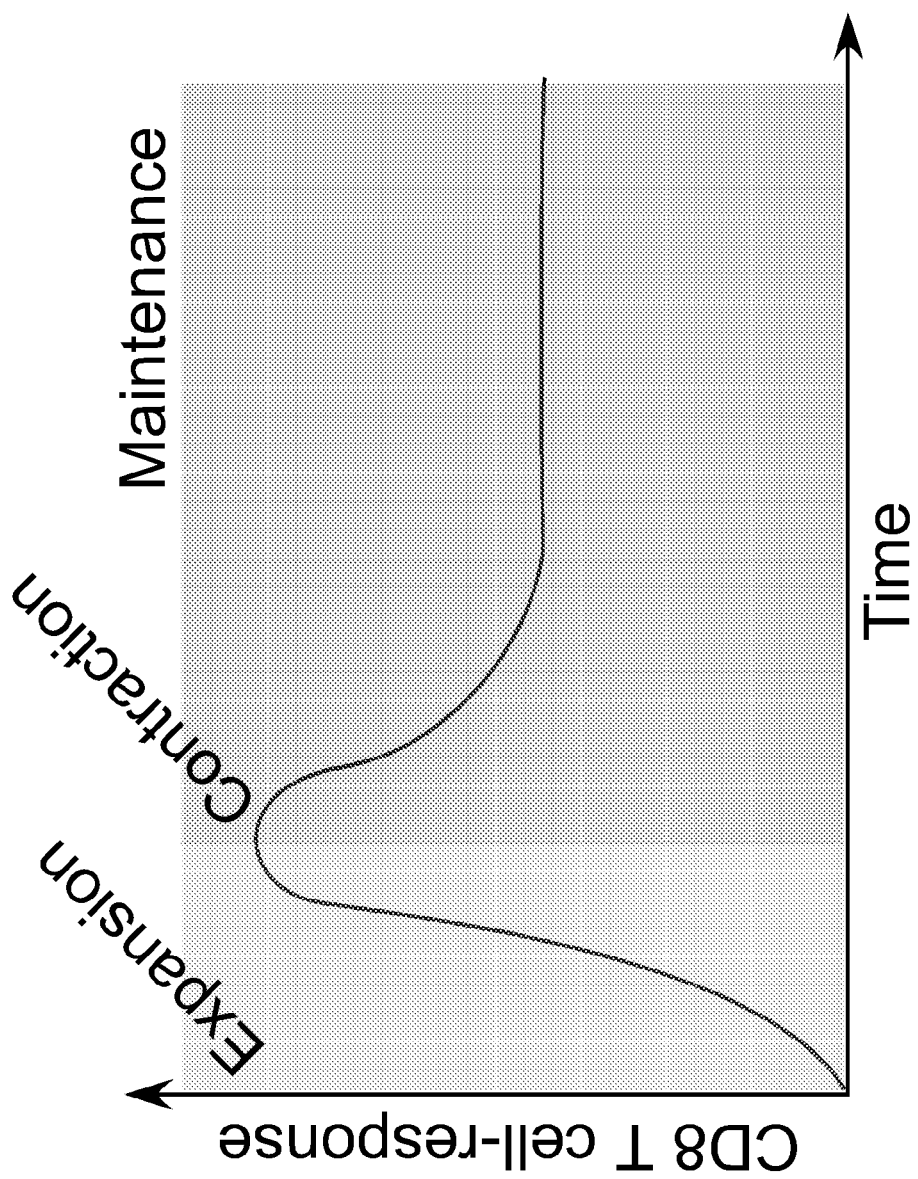
FIG. 1 is a schematic model of virus-specific $CD8^+$ T cell responses during an acute viral infection. Virus-specific $CD8^+$ T cells expand upon viral infection and become effector T cells. The expansion phase is followed by a contraction phase in which 90-95% of the effector cells die. The remaining effector cells differentiate into memory T cells during the contraction phase, and these memory cells further differentiate into high quality memory T cells during the maintenance phase.

The nucleic and amino acid sequences listed in the accompanying sequence listing are shown using standard letter abbreviations for nucleotide bases, and three letter code for amino acids, as defined in 37 C.F.R. 1.822. For double-stranded DNA sequences, only one strand of each nucleic acid sequence is shown, but the complementary strand is understood as included by any reference to the displayed strand. In the accompanying sequence listing:

SEQ ID NO: 1 is the nucleotide sequence of a shRNA specific for raptor.

SEQ ID NO: 2 is the nucleotide sequence of a shRNA specific for FKBP12.

SEQ ID NOs: 3 and 4 are the nucleotide and amino acid sequences, respectively, of human mTOR deposited under GENBANK™ Accession No. NM_004958 on Apr. 4, 2002.

SEQ ID NOs: 5 and 6 are the nucleotide and amino acid sequences, respectively, of human mTOR deposited under GENBANK™ Accession No. BC117166 on Jun. 26, 2006.

SEQ ID NOs: 7 and 8 are the nucleotide and amino acid sequences, respectively, of LCMV glycoprotein deposited under GENBANK™ Accession No. M20869 on Aug. 2, 1993.

SEQ ID NO: 9 is the amino acid sequence of the LCMV 33-41 epitope.

SEQ ID NOs: 10 and 11 are the nucleotide sequences of the sense and antisense strands, respectively, of an mTOR-specific shRNA.

SEQ ID NOs: 12 and 13 are the nucleotide sequences of the sense and antisense strands, respectively, of a raptor-specific shRNA.

SEQ ID NOs: 14 and 15 are the nucleotide sequences of the sense and antisense strands, respectively, of a FKBP12-specific shRNA.

SEQ ID NOs: 16 and 17 are the nucleotide sequences of the sense and antisense strands, respectively, of an S6K1-specific shRNA.

SEQ ID NOs: 18 and 19 are the nucleotide sequences of the sense and antisense strands, respectively, of an eIF4E-specific shRNA.

DETAILED DESCRIPTION

I. Abbreviations

Ad Adenovirus
AFP Alphafetoprotein
CD Cluster of differentiation
CEA Carcinoembryonic antigen
CFSE Carboxyfluorescein succinimidyl ester
DC Dendritic cell
FACS Fluorescence activated cell sorting
FBS Fetal bovine serum
FKBP12 FK506-binding protein 12
GβL G-protein β-subunit
GFP Green fluorescent protein
GP Glycoprotein
HBV Hepatitis B virus
HBcAg Hepatitis B core antigen
HCV Hepatitis C virus
HIV Human immunodeficiency virus
HPV Human papillomavirus
IFN Interferon
IGF Insulin growth factor
IP Intraperitoneally
KLRG Killer cell lectin-like receptor G
LCMV Lymphocytic choriomeningitis virus
LN Lymph node
MHC Major histocompatibility complex
miRNA Micro RNA
mTOR Mammalian target of rapamycin
mTORC1 mTOR complex 1
mTORC2 mTOR complex 2
MVA Modified Vaccinia Ankara
NP Nucleoprotein
ODN Oligodeoxynucleotide
PBMC Peripheral blood mononuclear cell
PFU Plaque forming unit
PRAME Preferentially expressed antigen of melanoma
PrCP Peridinin chlorophyll protein
PSA Prostate specific antigen
Raptor Regulatory associated protein of mTOR
Rictor Rapamycin-insensitive companion of mTOR
RNA Ribonucleic acid RNAi RNA interference
SEM Standard error of the mean
shRNA Short hairpin RNA
VLP Virus-like particle
VV Vaccinia virus
WT Wilms tumor II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Acute infection: An infection (such as a viral infection) having a relatively short time course.

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administration: The introduction of a composition into a subject by a chosen route. For example, if the chosen route is intravenous, the composition (for example, rapamycin) is administered by introducing the composition into a vein of the subject.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest, U.S. Department of Health and Human Services,* 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Antigen-specific T cell response: Refers to a T cell immune response that is directed against a particular antigen. Antigen-specific T cells are T cells that are capable of specifically recognizing (via T cell receptors) and responding to an antigen. As used herein, "enhancing" an antigen-specific T cell response includes, but is not limited to, increasing the number, quality and/or activity of T cells, such as CD4$^+$ and/or CD8$^+$ memory T cells. There are three phases of an antigen-specific CD8$^+$ T cell response after exposure to antigen (such as during a viral infection). First, during the expansion phase naïve antigen-specific CD8$^+$ T cells exponentially expand and become effector T cells. These effector T cells stop proliferating approximately 1 to 2 weeks after exposure and enter the contraction phase. During the contraction phase, effector CD8$^+$ T cells gradually acquire memory T cell phenotype and function. The contraction phase is also referred to as the "cell death phase" as a significant number of activated T cells (often about 90%) die during this phase. The maintenance phase, which is also referred to as the "memory phase," follows the contraction phase and is characterized by long-term survival of antigen-specific memory cells.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target mRNA, the duplex is recognized by RNase H (an enzyme that recognizes DNA:RNA duplexes), resulting in cleavage of the mRNA.

Binding affinity: Affinity of an antibody for an antigen. In one embodiment, affinity is calculated by a modification of the Scatchard method described by Frankel et al. (*Mol. Immunol.*, 16:101-106, 1979). In some cases, binding affinity is measured by an antigen/antibody dissociation rate. In another cases, a high binding affinity is measured by a competition radioimmunoassay or ELISA.

$CD8^+$ effector T cells/$CD4^+$ effector T cells: Activated T cells that express CD8 or CD4, respectively. During an immune response, effector T cells divide rapidly and secrete cytokines to modulate the immune response. T effector cells are also known as T helper cells.

$CD8^+$ memory T cells/$CD4^+$ memory T cells: Antigen-specific $CD8^+$ or $CD4^+$ T cells that persist long-term after an immune response. Upon re-exposure to the antigen, memory T cells expand and become T effector cells.

Chronic infection: An infection (such as a viral infection) that persists for a relatively long period of time. Chronic infections typically result in little to no change in symptoms over time and/or progress very slowly.

High quality T cells: As used herein, a "high quality T cell" is an antigen-specific T cell that exhibits superior properties relative to standard T cells, such as increased proliferation in response to antigen or increased viral clearance. High quality T cells can be identified by detecting the expression level of specific cell-surface markers. In some embodiments, a high quality T cell is a T cell expressing one or more of $CD127^{high}$, $CD62L^{high}$, $KLRG-1^{low}$, $CD27^{high}$ and $Bcl-2^{high}$. In some embodiments, high quality T cells are $CD127^{high}$, $CD27^{high}$ and $Bcl-2^{high}$. In some embodiments, high quality T cells are $KLRG-1^{low}$, $CD27^{high}$ and $Bcl-2^{high}$. In some embodiments, high quality T cells are $CD127^{high}$, $CD62L^{high}$, $KLRG-1^{low}$ and $Bcl-2^{high}$. In some embodiments, high quality T cells are $CD127^{high}$, $CD62L^{high}$ and $KLRG-1^{low}$. Similarly, "enhancing the quality of a T cell" refers to increasing functional activity of a T cell, such as increased proliferation in response to antigen or increased viral clearance. In some embodiments, enhancing the quality of a T cell includes increasing expression of one or more of CD127, CD62L, CD27 and Bcl-2, and/or decreasing expression of KLRG-1. In some embodiments, the increase or decrease in expression is about 1.5-fold, about 2-fold, about 3-fold, about 5-fold or about 10-fold. High quality T cells can be identified according to standard methods known in the art, such as by FACS.

Immune response: A response of a cell of the immune system, such as a B cell or T cell, to a stimulus. In some embodiments, the response is specific for a particular antigen (an "antigen-specific response"). In some embodiments, an immune response is a T cell response, such as a $CD8^+$ response. In another embodiment, the response is a B cell response, and results in the production of antigen-specific antibodies. As used herein, "stimulating an immune response" refers to promoting or enhancing the response of the cells of the immune system to a stimulus, such as an antigen.

Immunogen: A compound, composition, or substance which is capable, under appropriate conditions, of stimulating an immune response, such as the production of antibodies or a T-cell response in an animal, including compositions that are injected or absorbed into an animal.

Increasing the proportion of $CD127^{High}KLRG-1^{Low}$ $CD8^+$ T cells: As used herein, "increasing the proportion of $CD127^{High}KLRG-1^{Low}$ $CD8^+$ T cells" refers to increasing the ratio of $CD127^{High}KLRG-1^{Low}$ to $CD127^{Low}KLRG-1^{High}$ $CD8^+$ T cells in the subject exposed to an antigen (such as an infectious agent, tumor or vaccine). As described herein, day 8 (the end of the T cell expansion phase) effector $CD8^+$ T cell populations are characterized by two subsets: (1) terminal effector T cells ($CD127^{Low}KLRG-1^{High}$), a large percentage of which die over the following 2-4 weeks; and (2) memory precursor cells ($CD127^{High}KLRG-1^{Low}$), which survive and differentiate to produce long-lived memory T cells. As disclosed herein, treatment of a subject exposed to an antigen with an mTOR inhibitor increases the proportion of antigen-specific $CD127^{High}KLRG-1^{Low}$ $CD8^+$ T cells in the subject. T cells expressing CD127 and KLRG-1, and their relative expression levels, can be identified according to standard methods known in the art, such as by FACS.

Inhibit expression or activity: As used herein, a compound that inhibits expression or activity of mTOR is a compound that reduces the level of mTOR mRNA or protein in a cell or tissue, or reduces (including eliminates) one or more activities of mTOR. For example, an antisense compound targeting mTOR inhibits expression of mTOR by promoting the degradation of mTOR mRNA, thereby reducing the level of mTOR protein. In some embodiments, mTOR expression is inhibited at least 10%, at least 25%, at least 50%, at least 75%, at least 90%, or at least 95% relative to a control, such as untreated control cells. As another example, an antibody or small molecule that specifically binds or targets mTOR may inhibit activity of mTOR by directly inhibiting its kinase activity or by preventing mTOR protein from interacting with another protein. In some embodiments, mTOR activity is inhibited at least 10%, at least 25%, at least 50%, at least 75%, at least 90%, or at least 95% relative to an untreated control.

Isolated: An "isolated" biological component, such as a nucleic acid, protein (including antibodies) or organelle that has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Low dose rapamycin: Refers to a dose of rapamycin that does not suppress antigen-specific T cell immune responses when administered during the expansion, contraction or maintenance phases of a T cell response. Generally, a low dose of rapamycin is about 0.01 to about 0.15 mg/kg, such as about 0.05 to about 0.1, or a dose that results in a blood concentration of approximately 5 to 20 ng/ml. In some examples a low dose of rapamycin is about 0.01, about 0.02, about 0.03, about 0.04, about 0.05, about 0.06, about 0.07, about 0.08, about 0.09, about 0.10, about 0.11, about 0.12, about 0.13, about 0.14 or about 0.15 mg/kg. In this context, "about" refers to a value within 0.005 mg/kg.

MicroRNA (miRNA): Single-stranded RNA molecules that regulate gene expression. miRNAs are generally 21-23 nucleotides in length. miRNAs are processed from primary transcripts known as pri-miRNA to short stem-loop structures called pre-miRNA and finally to functional miRNA. Mature miRNA molecules are partially complementary to one or more messenger RNA molecules, and their primary function is to down-regulate gene expression. MicroRNAs regulate gene expression through the RNAi pathway.

mTOR: A serine/threonine kinase that regulates the expression of proteins involved in cell growth and proliferation via phosphorylation of specific substrates. As such, mTOR plays an integral role in the response to numerous hormones and growth factors. Synonyms for mTOR include FRAP1, FKBP12-rapamycin complex-associated protein, FK506-binding protein 12-rapamycin complex-associated protein 1, rapamycin target protein and RAPT1. Nucleotide and amino acid sequences of mTOR are known in the art (for example, GENBANK™ Accession No. NM_004958, deposited on Apr. 4, 2002 (SEQ ID NOs: 3 and 4), and GENBANK™ Accession No. BC117166, deposited on Jun. 26, 2006 (SEQ ID NOs: 5 and 6)).

mTOR inhibitor: A molecule that inhibits expression or activity of mTOR. mTOR inhibitors include, but are not limited to small molecule, antibody, peptide and nucleic acid inhibitors. For example, an mTOR inhibitor can be a molecule that inhibits the kinase activity of mTOR or inhibits binding of mTOR to a ligand. Inhibitors of mTOR also include molecules that down-regulate expression of mTOR, such as an antisense compound. A number of mTOR inhibitors are known in the art and are discussed below. In some embodiments, the mTOR inhibitor is rapamycin or a rapamycin analog.

Pathogen: A biological agent that causes disease or illness to its host. Pathogens include, for example, bacteria, viruses, fungi, protozoa and parasites. Pathogens are also referred to as infectious agents or infectious microorganisms.

Examples of pathogenic viruses include, but are not limited to those in the following virus families: Retroviridae (for example, human immunodeficiency virus (HIV), human T-cell leukemia viruses; Picornaviridae (for example, polio virus, hepatitis A virus, hepatitis C virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus), rubella viruses); Flaviridae (for example, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses, including avian flu and swine flu); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxyiridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus).

Examples of bacterial pathogens include, but are not limited to: *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelii*.

Examples of fungal pathogens include, but are not limited to: *Cryptococcus neoformans, Histoplasma capsulatum, Coccidioides immitis, Blastomyces dermatitidis, Chlamydia trachomatis, Candida albicans*.

Other pathogens (such as parasitic pathogens) include, but are not limited to: *Plasmodium falciparum, Plasmodium vivax, Trypanosoma cruzi* and *Toxoplasma gondii*.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some circumstances, variations in the cDNA sequence that result in amino acid changes, whether conservative or not, are minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity can be found at the National Center for Biotechnology Information website.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term purified does not require absolute purity; rather, it is intended as a relative term. Thus, for example, a purified antigen is one in which the specified antigen is more enriched than it is in its generative environment, for instance within a cell extract. Preferably, a preparation of a specified antigen is purified such that the antigen represents at least 75% of the total content of the preparation. In some embodiments, a purified preparation contains at least 80%, at least 85%, at least 90%, at least 95%, at least 99% or more of the specified antigen. As used herein, "purified" antigens include recombinantly produced antigens.

Rapamycin: A small molecule with known immunosuppressive and anti-proliferative properties. Rapamycin, also known as sirolimus, is a macrolide that was first discovered as a product of the bacterium *Streptomyces hygroscopicus*. Rapamycin binds and inhibits the activity of mTOR. The chemical formula of rapamycin is $C_{51}H_{79}NO_{13}$ and the International Union of Pure and Applied Chemistry (IUPAC) name is (3S,6R,7E,9R,10R,12R,14S,15E,17E,19E,21S,23S, 26R,27R,34aS)-9,10,12,13,14,21,22,23,24,25,26,27,32,33, 34,34a-hexadecahydro-9,27-dihydroxy-3-[(1R)-2-[(1S,3R, 4R)-4-hydroxy-3-methoxycyclohexyl]-1-methylethyl]-10, 21-dimethoxy-6,8,12,14,20,26-hexamethyl-23,27-epoxy-3H-pyrido[2,1-c][1,4]-oxaazacyclohentriacontine-1,5,11, 28,29(4H,6H,31H)-pentone.

Ribozyme: A catalytic RNA molecule. In some cases, ribozymes can bind to specific sites on other RNA molecules and catalyze the hydrolysis of phosphodiester bonds in the RNA molecules.

RNA interference (RNAi): Refers to a cellular process that inhibits expression of genes, including cellular and viral genes. RNAi is a form of antisense-mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs.

Sample: As used herein, a "sample" obtained from a subject refers to a cell, fluid or tissue sample. Bodily fluids include, but are not limited to, blood, serum, urine, saliva and spinal fluid. Cell samples include, for example, PBMCs, white blood cells, lymphocytes, or other cells of the immune system.

Short hairpin RNA (shRNA): A sequence of RNA that makes a tight hairpin turn and can be used to silence gene expression via the RNAi pathway. The shRNA hairpin structure is cleaved by the cellular machinery into siRNA.

Small interfering RNA (siRNA): A double-stranded nucleic acid molecule that modulates gene expression through the RNAi pathway. siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs."

Small molecule inhibitor: A molecule, typically with a molecular weight less than about 1000 Daltons, or in some embodiments, less than about 500 Daltons, wherein the molecule is capable of inhibiting, to some measurable extent, an activity of a target molecule.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount of an mTOR inhibitor necessary to enhance a T cell response.

Tumor antigen: A tumor antigen is an antigen produced by tumor cells that can stimulate tumor-specific T-cell immune responses. Exemplary tumor antigens include, but are not limited to, RAGE-1, tyrosinase, MAGE-1, MAGE-2, NY-ESO-1, Melan-A/MART-1, glycoprotein (gp) 75, gp100, beta-catenin, preferentially expressed antigen of melanoma (PRAME), MUM-1, Wilms tumor (WT)-1, carcinoembryonic antigen (CEA), and PR-1. Additional tumor antigens are known in the art (for example see Novellino et al., *Cancer Immunol. Immunother.* 54(3):187-207, 2005) and are described below. Tumor antigens are also referred to as "cancer antigens."

Tumor, cancer, neoplasia or malignancy: The result of abnormal and uncontrolled growth of cells. Neoplasia, malignancy, cancer and tumor are often used interchangeably and refer to abnormal growth of a tissue or cells that results from excessive cell division. Hematological cancers are cancers of the blood or bone marrow. Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas and are named for the type of cells that form them. Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Vaccine: A preparation of immunogenic material capable of stimulating an immune response, administered for the prevention, amelioration, or treatment of infectious or other types of disease, such as cancer. The immunogenic material may include live-attenuated or killed microorganisms (such as bacteria or viruses), or antigenic proteins, peptides or DNA derived from them. In some cases, the vaccine is a subunit vaccine, which is an immunizing agent that has been treated to remove traces of nucleic acid (such as viral nucleic acid) so that only protein subunits remain. The subunits have less risk of causing adverse reactions. The vaccine can also be a live vaccine, which is a vaccine prepared from living attenuated organisms or from viruses that have been attenuated but can still replicate in the cells of the host organism.

The immunogenic material for a cancer vaccine may include, for example, a protein or peptide expressed by a tumor or cancer cell. Vaccines may elicit both prophylactic (preventative) and therapeutic responses. Methods of administration vary according to the vaccine, but may include inoculation, ingestion, inhalation or other forms of administration.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, GENBANK™ Accession numbers and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

There are three phases of a virus-specific CD8$^+$ T cell response after virus infection (FIG. 1). First, naïve virus-specific CD8$^+$ T cells exponentially expand and become effector T cells. These effector T cells stop proliferating approximately 1 to 2 weeks after infection and enter the contraction phase. During the contraction phase, effector CD8$^+$ T cells gradually acquire memory T cell phenotype and function.

Disclosed herein is the surprising finding that treatment with an mTOR inhibitor enhances T cell immune responses. To enhance antigen-specific T cell immune responses in a subject, an mTOR inhibitor is administered during the contraction phase of a T cell response, or is administered at any time prior to or subsequent to antigen challenge when administered at a low dose. Thus, provided herein is a method of enhancing an antigen-specific T cell response in a subject exposed to an antigen by administering to the subject a therapeutically effective amount of an mTOR inhibitor, thereby enhancing a T cell immune response in a subject.

The subject in need of treatment can be any subject exposed to an antigen, such as antigen from a pathogen during a viral, bacterial, fungal or parasitic infection. In some cases, the subject in need of treatment is a subject with a tumor who is exposed to a tumor antigen expressed by the tumor or cancer cells. The subject in need of treatment can also be exposed to an antigen that is a component of a vaccine, such as for prophylactic treatment of a disease (including, for example, an infectious disease or cancer).

In particular embodiments, provided herein is a method of enhancing an antigen-specific T cell response in a subject in need of treatment by administering to the subject a therapeutically effective amount of an antigen and a therapeutically effective amount of an mTOR inhibitor, thereby enhancing a T cell immune response in a subject.

In some embodiments, the T cells are CD8$^+$ T cells or CD4$^+$ T cells, or both. The CD8$^+$ or CD4$^+$ T cells can be effector T cells or memory T cells.

In some embodiments, enhancing an antigen-specific T cell response in a subject exposed to an antigen includes increasing the number of CD8$^+$ T cells, enhancing the quality of CD8$^+$ T cells, or both.

In some embodiments, the CD8$^+$ T cells are CD8$^+$ effector T cells. In some embodiments, enhancing the quality of CD8$^+$ effector T cells is characterized by an increase in the proportion of antigen-specific CD127$^{High}$KLRG-1$^{Low}$ CD8$^+$ T cells in a subject relative to a control, such as the proportion of antigen-specific CD127$^{High}$KLRG-1$^{Low}$ CD8$^+$ T cells prior to or in the absence of treatment with an mTOR inhibitor. The control can also be a historical or reference value.

In some embodiments, the CD8$^+$ T cells are CD8$^+$ memory T cells. In some embodiments, enhancing the quality of CD8$^+$ memory T cells is characterized by an increase in expression of CD127, an increase in expression of CD62L, an increase in expression of Bcl-2, an increase in expression of CD27, a decrease in expression of KLRG, or a combination thereof. In some examples, a decrease in expression of a T cell marker is a decrease of at least about 10%, at least about 20%, at least about 30%, at least about 40%, or at least about 50%. In some examples, an increase in expression of a T cell marker is an increase of at least about 10%, at least about 20%, at least about 30%, at least about 40%, or at least about 50%. The increase or decrease in expression of the T cell marker is relative to a control, such as expression level prior to or in the absence of treatment with an mTOR inhibitor. The control can also be a historical or reference value.

In some embodiments, enhancing an antigen-specific T cell response comprises increasing the number of $CD4^+$ T cells, enhancing the quality of $CD4^+$ T cells, or both. In some embodiments, the $CD4^+$ T cells are $CD4^+$ memory T cells.

In some embodiments, the antigen administered to the subject is a component of a vaccine.

The antigen can be any type of antigen against which an immune response is desired, such as an antigen from a pathogen, or a tumor antigen or antigen that is part of a vaccine. Accordingly, a subject can be exposed to an antigen, such as occurs during an infection with a pathogen or with development of cancer, or a subject can be administered the antigen, such as by prophylactic or therapeutic immunization with a vaccine. In some embodiments, the antigen is from a pathogen, such as, but not limited to a virus, bacterium, fungus or parasite. The antigen from the pathogen is any protein or other molecule capable of eliciting an immune response in a subject exposed to the antigen. In some examples, the antigen is a virus, such as human immunodeficiency virus (HIV) or hepatitis B virus (HBV). In some embodiments, the subject has an acute infection. For example, influenza viruses and rhinoviruses typically cause acute infections. In other embodiments, the subject has a chronic infection. Examples of chronic infections include, but are not limited to, hepatitis C virus infection (HCV) and HIV infection.

In some embodiments, the antigen is a tumor antigen. In one embodiment, the tumor is a hematologic cancer. In some examples, the hematologic cancer is leukemia or lymphoma, such as lymphocytic leukemia, myelogenous leukemia, myelocytic leukemia, Hodgkin's disease, non-Hodgkin's lymphoma and multiple myeloma. In another embodiment, the tumor is a solid tumor. In some examples, the solid tumor is a carcinoma, melanoma, sarcoma or central nervous system tumor. Examples of solid tumors include, but are not limited to hepatocellular carcinoma, malignant melanoma, colon cancer, pancreatic cancer, breast cancer, lung cancers, ovarian cancer, prostate cancer and retinoblastoma.

In some embodiments of the methods of enhancing a T cell response in a subject, the subject is naturally exposed to the antigen such as via an infection with a pathogen, or due to the development of a tumor. In these cases, the mTOR inhibitor is generally administered following exposure to the antigen to augment T cell immune responses in the exposed subject.

In some embodiments, the method of an enhancing a T cell response in a subject further comprises administering a vaccine to the subject. In one embodiment, the vaccine is a vaccine against a pathogen, such as a virus. In another embodiment, the vaccine is a cancer vaccine.

In some embodiments, the mTOR inhibitor is administered prior to administration of the antigen (such as by administration of a vaccine). In one embodiment, the mTOR inhibitor is administered up to three days prior to administration of the antigen. In another embodiment, the mTOR inhibitor is administered up to one day prior to administration of the antigen.

In some embodiments, the mTOR inhibitor is administered after administration of the antigen. In one embodiment, the mTOR inhibitor is administered up to 20 days following administration of the antigen. In some examples, the mTOR inhibitor is administered 7 to 20 days following administration of the antigen. In other examples, the mTOR inhibitor is administered 10 to 15 days following administration of the antigen. In some embodiments, the mTOR inhibitor is administered on the same day as the antigen, including, but not limited to, within 5 minutes, within 10 minutes, or within 15 minutes of administration of the antigen. In some examples, the mTOR inhibitor is administered simultaneously, such as within 0 to 5 minutes of administration of the vaccine. In other examples, the mTOR inhibitor is administered within 5 to 15 minutes of administration of the antigen.

In some embodiment, the mTOR inhibitor is administered in a single dose. In other embodiments, the mTOR inhibitor is administered in multiple doses. In some examples, the mTOR inhibitor is administered in 1 to 40 doses, such as 5 to 30 doses, 10 to 25 doses, or 15 to 20 doses. When administered in multiple doses, the mTOR inhibitor can be administered prior to, on the same day as, or following administration of the antigen, or a combination thereof. For example, a subject can be administered the mTOR inhibitor daily for three days prior to administration of the antigen and daily for one week following immunization. As another example, a subject can be administered the mTOR inhibitor on the same day as the antigen and then administered the mTOR inhibitor daily for up to one week. In some embodiments, the mTOR inhibitor is administered daily. In some examples, the mTOR inhibitor is administered daily for one week. In other embodiments, the mTOR inhibitor is administered weekly.

In some embodiments, the mTOR inhibitor is administered continuously, such as part of a patch or other transdermal delivery means.

In some embodiments, the mTOR inhibitor is rapamycin or a rapamycin analog. In one embodiment, the dose of rapamycin is about 0.2 to about 1.0 mg/kg, such as about 0.4 to about 0.8 mg/kg. In some examples, the dose of rapamycin is about 0.2, about 0.3, about 0.4, about 0.5, about 0.6, about 0.7, about 0.8, about 0.0 or about 1.0 mg/kg. In another embodiment, the dose of rapamycin is a low dose of rapamycin. In one embodiment, the low dose of rapamycin is about 0.01 to about 0.15 mg/kg, such as about 0.05 to about 0.1 mg/kg. In some examples, a low dose of rapamycin is about 0.01, about 0.02, about 0.03, about 0.04, about 0.05, about 0.06, about 0.07, about 0.08, about 0.09, about 0.10, about 0.11, about 0.12, about 0.13, about 0.14 or about 0.15 mg/kg. In this context, "about" refers to a value within 0.005 mg/kg.

When a low dose of rapamycin (or another mTOR inhibitor) is used, administration can occur at any time relative to exposure to or administration of the antigen. When a higher dose of inhibitor is used, it is typically effective when delivered to a subject after exposure to the antigen, such as up to about 10, up to about 15 days or up to about 20 days following exposure, which correlates with the T cell contraction phase of an immune response in humans (Miller et al., *Immunity* 28(5):710-722, 2008). In some examples, the higher dose of rapamycin is administered 7 to 20 days following exposure to or administration of antigen.

In some embodiments, the method further comprises measuring the number of antigen-specific T cells in a sample obtained from the subject. In other embodiments, the method further comprises measuring the expression of one or more of CD127, CD62L, Bcl-2, CD27 and KLRG-1 in T cells from a sample obtained from the subject.

Also provided herein is a method of increasing the proportion of antigen-specific $CD127^{High}KLRG-1^{Low}$ $CD8^+$ T cells in a subject, comprising administering to the subject a therapeutically effective amount of an antigen and an mTOR inhibitor, thereby increasing the proportion of antigen-specific CD127$^{High}$KLRG-1$^{Low}$ CD8$^+$ T cells in the subject. In some embodiments, an increase in the proportion of antigen-specific CD127$^{High}$KLRG-1$^{Low}$ CD8$^+$ T cells is relative to the proportion of CD127$^{High}$KLRG-1$^{Low}$ CD8$^+$ T cells in the absence of treatment. In some embodiments, the subject has an acute or chronic infection, or has a tumor.

In some examples, the method of increasing the proportion of antigen-specific CD127$^{High}$KLRG-1$^{Low}$ CD8$^+$ T cells in a subject exposed to an antigen, comprises (i) selecting a subject in need of treatment; (ii) administering to the subject an mTOR inhibitor; and (iii) measuring the proportion of antigen-specific CD127$^{High}$KLRG-1$^{Low}$ CD8$^+$ T cells in the subject relative to the proportion of CD127$^{High}$KLRG-1$^{Low}$ CD8$^+$ T cells in the absence of treatment.

Further provided is a method of increasing expression of CD127, CD62L, Bcl-2 and CD27, and decreasing expression of KLRG-1, in CD8+ T cells of a subject, comprising administering to the subject a therapeutically effective amount of an antigen and an mTOR inhibitor, thereby increasing expression of CD127, CD62L, Bcl-2 and CD27, and decreasing expression of KLRG-1, in CD8+ T cells of the subject. In some embodiments, the increase or decrease in expression of the T cell markers is relative to expression in the absence of treatment. In some embodiments, the subject has an acute or chronic infection, or has a tumor.

In some examples, the method of increasing expression of CD127, CD62L, Bcl-2 and CD27, and decreasing expression of KLRG-1, in CD8$^+$ T cells of a subject exposed to an antigen comprises (i) selecting a subject in need of treatment; (ii) administering to the subject an mTOR inhibitor; and (iii) measuring expression of CD127, CD62L, Bcl-2, CD27 and KLRG-1 in CD8$^+$ T cells of a subject relative to expression in the absence of treatment.

Also provided is the use of an mTOR inhibitor and a vaccine comprising an antigen in the manufacture of a medicament for enhancing an antigen-specific T cell response in a subject, wherein enhancing an antigen-specific T cell response in a subject comprises increasing the number of antigen-specific T cells or enhancing the quality of antigen-specific T cells in the subject.

Also provided herein are compositions comprising an mTOR inhibitor and an antigen and/or a vaccine. In some embodiments, the vaccine is a live vaccine. In some embodiments, the vaccine is a subunit vaccine. In some embodiments, the compositions comprise an mTOR inhibitor, purified antigen and an adjuvant. The antigen can be any antigen, such as an antigen from a pathogen, a tumor antigen or a vaccine antigen. Suitable antigens are described herein and are well known in the art. In some embodiments, the compositions provided herein further comprise a pharmaceutically acceptable carrier. Further provided is the use of such compositions in the manufacture of a medicament for enhancing an antigen-specific T cell response in a subject.

IV. Mammalian Target of Rapamycin (mTOR) Inhibitors

Inhibitors of mTOR for use with the methods claimed herein can be any type of molecule that inhibits expression or activity of mTOR. For example, mTOR inhibitors, include, but are not limited to small molecules, synthetic compounds, antibodies, peptides and nucleic acids (including, for example, antisense oligonucleotides, small interfering RNA (siRNA), short hairpin RNA, microRNA, ribozymes and the like).

A. Small Molecule Inhibitors

A number of small molecule mTOR inhibitors are known, some of which are currently being used to treat a variety of diseases. In addition, a number of mTOR inhibitors are under investigation in clinical trials for treating of diseases such as cancer. The best characterized mTOR inhibitor is rapamycin, a naturally occurring small molecule with known immunosuppressive and anti-proliferative properties. Rapamycin, also known as sirolimus, is a macrolide that was first discovered as a product of the bacterium *Streptomyces hygroscopicus*. Rapamycin binds and inhibits the activity of mTOR. Rapamycin is also marketed under the name RAPAMUNE™. Provided in Table 1 below is a list of some of the mTOR inhibitors currently being tested in clinical trials.

TABLE 1

| mTOR inhibitors under evaluation in clinical trials | | |
| --- | --- | --- |
| Compound | Company | Description |
| RAD001 | Novartis | Orally available derivative of rapamycin |
| OSI-027 | OSI Pharmaceuticals | Inhibits the kinase activity associated with both the mTORC1 and mTORC2 complexes |
| AP23573 | Ariad Pharmaceuticals | Rapamycin analog |
| AP23675 | Ariad Pharmaceuticals | Rapamycin analog |
| AP23841 | Ariad Pharmaceuticals | Rapamycin analog |
| ABI-009 | Abraxis Bioscience Inc. | mTOR inhibitor |
| MK8669 | Merck & Co. | mTOR inhibitor |
| TOP216 | Topotarget A/S | mTOR inhibitor |
| TAFA93 | Isotechnika Inc. | Prodrug of rapamycin |
| TORISEL ™ | Wyeth Pharmaceuticals | mTOR inhibitor |
| CERTICAN ™ | Novartis AG | mTOR inhibitor |

Additional mTOR inhibitors, including rapamycin derivatives and analogs have been described, such as, for example, those disclosed in PCT Publication Nos. WO 2007/135411, WO 98/02441, WO 01/14387 and WO 03/64383; and European Patent No. EP1880723.

B. Antisense Compounds

In addition to small molecule inhibitors, antisense compounds that specifically target and down-regulate expression of mTOR can be used with the methods provided herein. Generally, the principle behind antisense technology is that an antisense compound hybridizes to a target nucleic acid and effects the modulation of gene expression activity, or function, such as transcription, translation or splicing. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide. Antisense oligonucleotides can also be used to modulate gene expression, such as splicing, by occupancy-based inhibition, such as by blocking access to splice sites.

Another example of modulation of gene expression by target degradation is RNA interference (RNAi) using small interfering RNAs (siRNAs). RNAi is a form of antisense-mediated gene silencing involving the introduction of double stranded RNA-like oligonucleotides leading to the sequence-specific reduction of targeted endogenous mRNA levels. Another type of antisense compound that utilizes the RNAi pathway is a microRNA. MicroRNAs are naturally occurring RNAs involved in the regulation of gene expression. However, these compounds can be synthesized to regulate gene expression via the RNAi pathway. Similarly, short hairpin RNAs (shRNAs) are RNA molecules that form a tight hairpin turn and can be used to silence gene expression via the RNAi pathway. The shRNA hairpin structure is cleaved by the cellular machinery into siRNA.

Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a messenger RNA.

Each of the above-described antisense compounds provides sequence-specific target gene regulation. This sequence-specificity makes antisense compounds effective tools for the selective modulation of a target nucleic acid of interest, such as mTOR.

Any type of antisense compound that specifically targets and regulates expression of mTOR is contemplated for use with the disclosed methods. Such antisense compounds include single-stranded compounds, such as antisense oligonucleotides, and double-stranded compounds, including compounds with at least partial double-stranded structure, including siRNAs, miRNAs, shRNAs and ribozymes. Methods of designing, preparing and using antisense compounds that specifically target mTOR are within the abilities of one of skill in the art.

Furthermore, sequences for mTOR are publicly available. Exemplary human mTOR nucleotide sequences are provided herein as SEQ ID NO: 3 (GENBANK™ Accession No. NM_004958, deposited on Apr. 4, 2002) and SEQ ID NO: 5 (GENBANK™ Accession No. BC117166, deposited on Jun. 26, 2006). Antisense compounds specifically targeting mTOR can be prepared by designing compounds that are complementary to an mTOR nucleotide sequence, particularly the mTOR mRNA sequence. Antisense compounds targeting mTOR need not be 100% complementary to mTOR to specifically hybridize and regulate expression the target gene. For example, the antisense compound, or antisense strand of the compound If a double-stranded compound, can be at least 75%, at least 80%, at least 85%, at least 90%, at least 95%, at least 99% or 100% complementary to the selected mTOR nucleic acid sequence. Methods of screening antisense compounds for specificity are well known in the art (see, for example, U.S. Patent Application Publication No. 2003-0228689). Exemplary mTOR shRNA sequences are provided herein as SEQ ID NOs: 10 and 11.

C. Antibodies Specific for mTOR

An mTOR polypeptide or a fragment or conservative variant thereof can be used to produce antibodies which are immunoreactive or specifically bind to an epitope of an mTOR. Polyclonal antibodies, antibodies which consist essentially of pooled monoclonal antibodies with different epitopic specificities, as well as distinct monoclonal antibody preparations are included.

The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992.

The preparation of monoclonal antibodies likewise is conventional (see, for example, Kohler & Milstein, Nature 256: 495, 1975; Coligan et al., sections 2.5.1-2.6.7; and Harlow et al. in: *Antibodies: a Laboratory Manual*, page 726, Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465, 1991; and Losman et al., *Int. J. Cancer* 46:310, 1990.

Alternatively, an antibody that specifically binds an mTOR polypeptide can be derived from a humanized monoclonal antibody. Humanized monoclonal antibodies are produced by transferring complementarity determining regions from another species such as a mouse from heavy and light variable chains of the immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Natl. Acad. Sci. U.S.A.* 69:2659, 1972). Alternatively, the variable chains can be linked by an intermolecular disulfide bond or cross-linked by chemicals such as glutaraldehyde (see, for example, Sandhu, *Crit. Rev. Biotech.* 12:437, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin, thyroglobulin, bovine serum albumin, and tetanus toxoid. The coupled peptide is then used to immunize the animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

V. Antigens and Vaccines

As described herein, administration of an mTOR inhibitor in conjunction with exposure to an antigen or administration of a vaccine, enhances antigen-specific T cell immune responses. The antigen can be any type of antigen against which an immune response is desired in a subject, or any antigen to which a subject is exposed. In some cases, a subject is exposed to the antigen during an infection, such as a viral, bacterial, fungal or parasitic infection. In other cases, the subject has a tumor and is exposed to a tumor-specific antigen. Alternatively, the antigen can be administered to a subject, such as in the form of a vaccine. In some embodiments, the vaccine is a vaccine against a pathogen, or a cancer vaccine.

A. Antigens

In some embodiments, the antigen is an antigen from a pathogen, such as a virus, bacterium, fungus or parasite. Viral pathogens include, but are not limited to retroviruses, such as human immunodeficiency virus (HIV) and human T-cell leukemia viruses; picornaviruses, such as polio virus, hepatitis A virus; hepatitis C virus, enteroviruses, human coxsackie viruses, rhinoviruses, echoviruses, and foot-and-mouth disease virus; caliciviruses, such as strains that cause gastroenteritis (e.g., Norwalk virus); togaviruses, such as alphaviruses (including chikungunya virus, equine encephalitis viruses, Sindbis virus, Semliki Forest virus, and Ross River virus) and rubella virus; flaviviruses, such as dengue viruses, yellow fever viruses, West Nile virus, St. Louis encephalitis virus, Japanese encephalitis virus, Powassan virus and other encephalitis viruses; coronaviruses, including severe acute respiratory syndrome (SARS) virus; rhabdoviruses, such as vesicular stomatitis virus and rabies virus; filoviruses, such as Ebola virus and Marburg virus); paramyxoviruses, such as parainfluenza virus, mumps virus, measles virus, and respiratory syncytial virus; orthomyxoviruses, such as influenza viruses (including avian influenza viruses and swine influenza viruses); bunyaviruses, such as Hantaan virus; Sin Nombre virus, and Rift Valley fever virus, phleboviruses and Nairo viruses; arenaviruses, such as Lassa fever virus and other hemorrhagic fever viruses, Machupo virus and Junin virus; reoviruses, such as mammalian reoviruses, orbiviurses and rotaviruses; birnaviruses; hepadnaviruses, such as hepatitis B virus; parvoviruses; papovaviruses, such as papilloma viruses, polyoma viruses and BK-virus; adenoviruses; herpesviruses, such as herpes simplex virus (HSV)-1 and HSV-2, cytomegalovirus, Epstein-Barr virus, varicella zoster virus, and other herpes viruses, including HSV-6); pox viruses, such as variola viruses and vaccinia viruses; irodoviruses, such as African swine fever virus; astroviruses; and unclassified viruses (for example, the etiological agents of spongiform encephalopathies, the agent of delta hepatitis (thought to be a defective satellite of hepatitis B virus).

Bacterial pathogens include, but are not limited to *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansai* and, *M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps), *Streptococcus pneumoniae*, pathogenic *Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelii*.

Fungal pathogens include, but are not limited to *Cryptococcus neoformans, Histoplasma capsulatum, Coccidioides immitis, Blastomyces dermatitidis, Chlamydia trachomatis, Candida albicans*. Parasitic pathogens include, but are not limited to *Plasmodium falciparum, Plasmodium vivax, Trypanosoma cruzi* and *Toxoplasma gondii*.

In some cases, the antigen is a tumor-associated antigen. Tumor antigens are proteins that are produced by tumor cells that elicit an immune response, particularly T-cell mediated immune responses. The tumor antigen can be any tumor-associated antigen, which are well known in the art and include, for example, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, macrophage colony stimulating factor, prostase, prostate-specific antigen (PSA), PAP, NY-ESO-1, LAGE-1a, p53, prostein, PSMA, Her2/neu, survivin and telomerase, prostate-carcinoma tumor antigen-1, MAGE, ELF2M, neutrophil elastase, ephrinB2, CD22, insulin growth factor (IGF)-I, IGF-II, IGF-I receptor and mesothelin. A list of selected tumor antigens and their associated tumors are shown below in Table 2.

TABLE 2

Exemplary tumors and their tumor antigens

| Tumor | Tumor Associated Target Antigens |
|---|---|
| Acute myelogenous leukemia | Wilms tumor 1 (WT1), PRAME, PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | NY-ESO-1 |
| Malignant melanoma | MAGE, MART, Tyrosinase, PRAME GP100 |
| Breast cancer | WT1, herceptin, epithelial tumor antigen (ETA) |
| Lung cancer | WT1 |
| Ovarian cancer | CA-125 |
| Prostate cancer | PSA |
| Pancreatic cancer | CA19-9, RCAS1 |
| Colon cancer | CEA |
| Renal cell carcinoma (RCC) | Fibroblast growth factor 5 |
| Germ cell tumors | AFP |

In some embodiments, a subject is administered an mTOR inhibitor following diagnosis of the subject (e.g. a diagnosis of the presence of an infection or cancer). The mTOR inhibitor can be administered in a single dose or in multiple doses over time. In some examples, a subject having an infection or cancer is administered an mTOR inhibitor daily for at least one week, at least one month or at least three months.

B. Vaccines

In some embodiments, the antigen is delivered as part of a vaccine. A number of vaccines against infectious diseases are currently approved for use in the United States, examples of which are listed below in Table 3.

TABLE 3

Approved Vaccines for Immunization and Distribution in the U.S.

| Product Name | Trade Name |
|---|---|
| Anthrax Vaccine Adsorbed | BIOTHRAX |
| BCG Vaccine | TICE BCG |
| BCG Vaccine | MYCOBAX |
| Diphtheria & Tetanus Toxoids Adsorbed | None |
| Diphtheria & Tetanus Toxoids Adsorbed | None |
| Diphtheria & Tetanus Toxoids & Acellular Pertussis Vaccine Adsorbed | TRIPEDIA |
| Diphtheria & Tetanus Toxoids & Acellular Pertussis Vaccine Adsorbed | INFANRIX |

TABLE 3-continued

Approved Vaccines for Immunization and Distribution in the U.S.

| Product Name | Trade Name |
|---|---|
| Diphtheria & Tetanus Toxoids & Acellular Pertussis Vaccine Adsorbed | DAPTACEL |
| Diphtheria & Tetanus Toxoids & Acellular Pertussis Vaccine Adsorbed, Hepatitis B (recombinant) and Inactivated Poliovirus Vaccine Combined | PEDIARIX |
| Diphtheria and Tetanus Toxoids and Acellular Pertussis Adsorbed and Inactivated Poliovirus Vaccine | KINRIX |
| Diphtheria and Tetanus Toxoids and Acellular Pertussis Adsorbed, Inactivated Poliovirus and Haemophilus b Conjugate (Tetanus Toxoid Conjugate) Vaccine | PENTACEL |
| Haemophilus b Conjugate Vaccine (Diphtheria CRM197 Protein Conjugate) | HIBTITER |
| Haemophilus b Conjugate Vaccine (Meningococcal Protein Conjugate) | PEDVAXHIB |
| Haemophilus b Conjugate Vaccine (Tetanus Toxoid Conjugate) | ACTHIB |
| Haemophilus b Conjugate Vaccine (Meningococcal Protein Conjugate) & Hepatitis B Vaccine (Recombinant) | COMVAX |
| Hepatitis A Vaccine, Inactivated | HAVRIX |
| Hepatitis A Vaccine, Inactivated | VAQTA |
| Hepatitis A Inactivated and Hepatitis B (Recombinant) Vaccine | TWINRIX |
| Hepatitis B Vaccine (Recombinant) | RECOMBIVAX HB |
| Hepatitis B Vaccine (Recombinant) | ENGERIX-B |
| Human Papillomavirus (Types 6, 11, 16, 18) Recombinant Vaccine | GARDASIL |
| Influenza Virus Vaccine | AFLURIA |
| Influenza Virus Vaccine, H5N1 | None |
| Influenza Virus Vaccine, Trivalent, Types A and B | FLULAVAL |
| Influenza Virus Vaccine, Live, Intranasal | FLUMIST |
| Influenza Virus Vaccine, Trivalent, Types A and B | FLUARIX |
| Influenza Virus Vaccine, Trivalent, Types A and B | FLUVIRIN |
| Influenza Virus Vaccine, Trivalent, Types A and B | FLUZONE |
| Japanese Encephalitis Virus Vaccine Inactivated | JE-VAX |
| Measles Virus Vaccine, Live | ATTENUVAX |
| Measles and Mumps Virus Vaccine, Live | M-M-Vax |
| Measles, Mumps, and Rubella Virus Vaccine, Live | M-M-R II |
| Measles, Mumps, Rubella and Varicella Virus Vaccine, Live | PROQUAD |
| Meningococcal Polysaccharide (Serogroups A, C, Y and W-135) Diphtheria Toxoid Conjugate Vaccine | MENACTRA |
| Meningococcal Polysaccharide Vaccine, Groups A, C, Y and W-135 Combined | MENOMUNE-A/C/Y/W-135 |
| Mumps Virus Vaccine Live | MUMPSVAX |
| Plague Vaccine | None |
| Pneumococcal Vaccine, Polyvalent | PNEUMOVAX 23 |
| Pneumococcal 7-valent Conjugate Vaccine (Diphtheria CRM197 Protein) | PREVNAR |
| Poliovirus Vaccine Inactivated (Human Diploid Cell) | POLIOVAX |
| Poliovirus Vaccine Inactivated (Monkey Kidney Cell) | IPOL |
| Rabies Vaccine | IMOVAX |
| Rabies Vaccine | RABAVERT |
| Rabies Vaccine Adsorbed | No Trade Name |
| Rotavirus Vaccine, Live, Oral | ROTARIX |
| Rotavirus Vaccine, Live, Oral, Pentavalent | ROTATEQ |
| Rubella Virus Vaccine Live | MERUVAX II |
| Smallpox (Vaccinia) Vaccine, Live | ACAM2000 |
| Smallpox Vaccine, Dried, Calf Lymph Type | DRYVAX |
| Tetanus & Diphtheria Toxoids Adsorbed for Adult Use | None |
| Tetanus & Diphtheria Toxoids Adsorbed for Adult Use | DECAVAC |
| Tetanus & Diphtheria Toxoids Adsorbed for Adult Use | TENIVAC |
| Tetanus Toxoid | None |
| Tetanus Toxoid Adsorbed | None |
| Tetanus Toxoid Adsorbed | None |
| Tetanus Toxoid, Reduced Diphtheria Toxoid and Acellular Pertussis Vaccine, Adsorbed | ADACEL |
| Tetanus Toxoid, Reduced Diphtheria Toxoid and Acellular Pertussis Vaccine, Adsorbed | BOOSTRIX |
| Typhoid Vaccine Live Oral Ty21a | VIVOTIF |
| Typhoid Vi Polysaccharide Vaccine | TYPHIM VI |
| Varicella Virus Vaccine Live | VARIVAX |
| Yellow Fever Vaccine | YF-VAX |
| Zoster Vaccine, Live | ZOSTAVAX |

With the exception of the HPV and HBV vaccines that prevent cervical cancer and liver cancer, respectively, as a result of inhibiting virus infection, there are currently no cancer vaccines approved for clinical use. However, a number of vaccine candidates are being evaluated for a wide variety of different types of cancer. For example, candidate tumor vaccines include, but are not limited to, antigen/adjuvant vaccines (cancer-specific antigenic protein fragments in combination with an adjuvant); whole-cell tumor vaccines (tumor cells taken from a subject's own tumor or the tumor of another patient); dendritic cell (DC) vaccines (DCs are isolated from a patient, stimulated ex vivo with the patient's cancer antigens and re-injected in the patient); DNA vaccines (nucleic acids encoding the sequence of a tumor antigen); and idiotype vaccines (antibodies specifically produced by a cancer cell). Accordingly, mTOR inhibitors can be used in conjunction with any such vaccine developed for eliciting immune responses against cancer.

A subject to be vaccinated can be administered an mTOR inhibitor prior to vaccination, at the same time as vaccination, following vaccination, or a combination thereof. An mTOR inhibitor can be administered in a single dose or multiple doses. Administration of mTOR inhibitors is discussed in detail below.

VI. Administration of mTOR Inhibitors

Administration of an mTOR inhibitor in accordance with the methods described herein can occur prior to, at the same time as, or following exposure to or delivery of an antigen or vaccine. The timing of administration depends in part on the dose of mTOR inhibitor administered. Low doses of mTOR inhibitor, such as rapamycin or a rapamycin analog, can be administered at any time relative to exposure of an antigen. Higher doses of mTOR inhibitor are more effective when delivered following exposure to an antigen or delivery of a vaccine, such as up to about 10 days, up to about 15 days, or up to about 20 days following exposure/delivery, which correlates with the T cell contraction phase of an immune response (Miller et al., *Immunity* 28(5):710-722, 2008).

In some embodiments, the mTOR inhibitor is administered up to three days prior to administration of a vaccine or exposure to an antigen. In some embodiments, the mTOR inhibitor is administered up to one day prior to administration of a vaccine or exposure to an antigen.

In some embodiments, the mTOR inhibitor is administered on the same day as the vaccine. As used herein, "on the same day" refers to administration that occurs within 24 hours (either before or after) administration of the vaccine. In some examples, the mTOR inhibitor is administered at the same time as the vaccine, such as within 0 to 5 minutes, within 5 to 10 minutes or within 10 to 15 minutes of administration of the vaccine. In some examples, the mTOR inhibitor is administered within about 15 minutes to 1 hour of administration of the vaccine. In other examples, the mTOR inhibitor is administered within about 30 minutes to about 2 hours of administration of the vaccine.

In some embodiments, the mTOR inhibitor is administered following vaccination or exposure to an antigen. In some embodiments, the mTOR inhibitor is administered up to 10 days, up to 15 days or up to 20 days after vaccination or exposure to an antigen. In some examples, the mTOR inhibitor is administered 7 to 20 days, or 10 to 15 days, following vaccination or exposure to antigen.

As described above, administration of an mTOR inhibitor can be accomplished by single or multiple doses. The dose administered to a subject should be sufficient to induce a beneficial therapeutic response (i.e. to establish sufficient immunological memory) in a subject over time, such as preventing or inhibiting infection by a pathogen, or inhibiting development or spread of a tumor. A therapeutically effective dose can also be determined by measuring the immune response, such as by detecting the number and quality of antigen-specific T cells, such as $CD8^+$ or $CD4^+$ memory T cells. As used herein, "multiple doses" means two or more doses, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more doses. In some examples, the mTOR inhibitor is administered in 1 to 40 doses, such as about 5 to 30 doses, about 10 to 25 doses or about 15 to 20 doses.

The dose required will vary from subject to subject depending on the species, age, weight and general condition of the subject, the severity of the disease or disorder being treated, the particular composition being used and its mode of administration. In some embodiments, the mTOR inhibitor is rapamycin and the dose is about 0.01 to about 0.15 mg/kg, such as about 0.05 to about 0.1 mg/kg when rapamycin is administered prior to or concomitant with the antigen or vaccine. In some examples, the dose of rapamycin is about 0.01, 0.02, 0.03, 0.04, 0.05, 0.06, 0.07, 0.08, 0.09, 0.10, 0.11, 0.12, 0.13, 0.14 or 0.15 mg/kg. In this context, "about" refers to a value within 0.005 mg/kg. A dose of about 0.01 to about 0.15 mg/kg typically results in a blood concentration of approximately 5 to 20 ng/ml. When the mTOR inhibitor is administered prior to or concomitant with the antigen at this relatively low dose, the inhibitor can also be administered for any period of time after administration of the antigen or vaccine. In other embodiments, the mTOR inhibitor is rapamycin and the dose is about 0.2 to about 1.0 mg/kg, such as about 0.4 to about 0.8 mg/kg, when rapamycin is administered after administration of the antigen or vaccine, such as during the T cell contraction phase of an immune response. In some examples, the dose of rapamycin is about 0.2, 0.3, 0.4, 0.5, 0.6, 0.7, 0.8, 0.9 or 1.0 mg/kg. In this context, "about" refers to a value within 0.05 mg/kg. A dose of about 0.2 to about 1.0 mg/kg typically results in a blood concentration of approximately 40 to 100 ng/ml. An appropriate dose can be determined by one of ordinary skill in the art using only routine experimentation.

When administered in multiple doses, the dosing schedule of the mTOR inhibitor can vary. In some embodiments, the mTOR inhibitor is administered twice a day, daily, weekly or monthly. In some embodiments, the mTOR inhibitor is administered daily for about one week. In other embodiments, the mTOR inhibitor is administered daily for about one month.

In some embodiments, the mTOR inhibitor is administered continuously, such as part of a patch or other transdermal application.

The mTOR inhibitors can be administered by any suitable route. The route of administration will be determined by a variety of factors, including the type of inhibitor used, the composition of inhibitor (e.g., liquid or solid form), and the immune response desired. Methods of administration include, but are not limited to, intradermal, topical, intramuscular, transdermal, intraperitoneal, parenteral, intravenous, subcutaneous, vaginal, rectal, intranasal, inhalation, oral or mist-spray delivery to the lungs. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local. Sterile injectable solutions are prepared by incorporating the active compounds in the required amount in the appropriate solvent with any other ingredients as required, followed by filtered sterilization.

In some embodiments, the mTOR inhibitor is administered topically or transdermally, for example in a patch, pad, bandage, cream, gel, lotion, spray, foam or paste. When administered as a patch, pad, bandage or the like, the patch, pad or bandage can be replaced at regular intervals to maintain a constant dose of mTOR inhibitor. Alternatively, the patch, pad or bandage can be applied for a given time period, such as one day, two days, three days, four days, five days, six days or seven days, or until the mTOR inhibitor is depleted from the patch, pad or bandage. Patches suitable for transdermal delivery of therapeutic agents are known in the art (see, for example, U.S. Patent Application Publication Nos. 2005/0142176; 2008/0274166; 2009/0028929; and 2009/0048567).

The mTOR inhibitors are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil. The mTOR inhibitors can be formulated in a neutral or salt form.

Pharmaceutically-acceptable salts include the acid addition salts (formed with the free amino groups of the protein) which are formed with inorganic acids such as, for example, hydrochloric or phosphoric acids, or organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

Generally, dispersions are prepared by incorporating the various sterilized active ingredients into a sterile vehicle which contains the basic dispersion medium and the required components. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The compositions of the present invention may also be administered into the epidermis using the Powderject System (Chiron, Emeryville, Calif.). The Powderject delivery technique works by the acceleration of fine particles to supersonic speed within a helium gas jet and delivers pharmaceutical agents and vaccines to skin and mucosal injection sites, without the pain or the use of needles.

In some embodiments, the mTOR inhibitors are administered in combination with other therapeutic agents. For example, the mTOR inhibitors (or vaccine administered in conjunction with the mTOR inhibitor) can be administered with an adjuvant, such as Freund incomplete adjuvant or Freund's complete adjuvant. Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

The following examples are provided to illustrate certain particular features and/or embodiments. These examples should not be construed to limit the disclosure to the particular features or embodiments described.

EXAMPLES

Example 1

Rapamycin Treatment During the Contraction Phase of a CD8$^+$ T Cell Response Induces High Quality Memory T Cells This example describes the finding that rapamycin treatment (i) induces high quality memory T cells during the contraction phase of a T cell response; (ii) enhances differentiation of memory T cells during the T cell contraction phase; and (iii) enhances high quality memory T cells during the contraction phase of recall T cell responses. This example further demonstrates that memory CD8+ T cells induced in rapamycin treated animals are high quality memory T cells.

There are three phases of a virus-specific CD8+ T cell response after virus infection (FIG. 1). First, naïve virus-specific CD8+ T cells exponentially expand and become effector T cells. These effector T cells stop proliferating approximately 1 to 2 weeks after infection and enter the contraction phase. During the contraction phase, effector CD8+ T cells gradually acquire memory T cell phenotype and function.

Figure 2A:
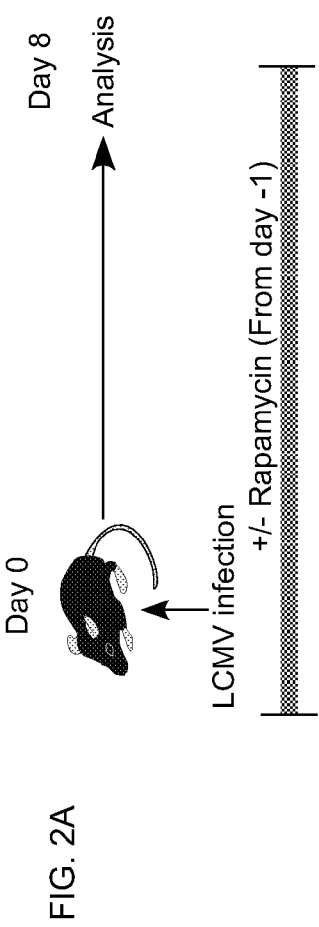
FIG. 2A is a schematic of the experimental design for testing the effect of rapamycin treatment on virus-specific $CD8^+$ T cells during the expansion phase. Mice were infected with lymphocytic choriomeningitis virus (LCMV) on Day 0 and treated with rapamycin every day starting one day prior to infection (Day −1). Peripheral blood mononuclear cells (PBMCs) from untreated (No Rapa) and rapamycin-treated (Rapa Tx) mice were analyzed on Day 8.
Figure 2B:
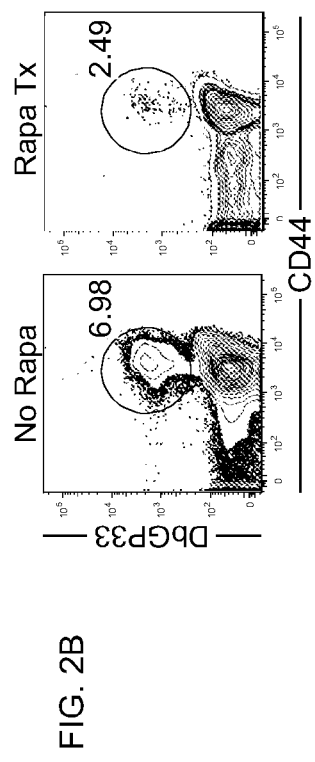
FIG. 2B shows fluorescence activated cell sorting (FACS) plots of PBMCs obtained from untreated and rapamycin-treated mice. PBMCs were stained with LCMV GP33 epitope-specific tetramer DbGP33, anti-CD8 and anti-CD44. The percentage of virus-specific CD8+ T cells is indicated.
Figure 2C:
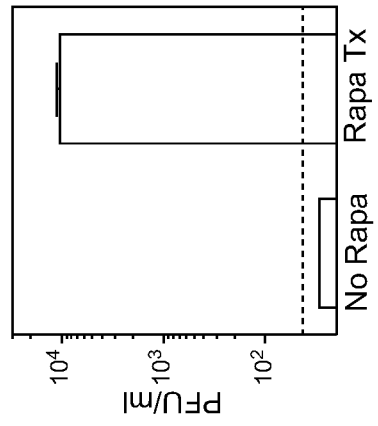
FIG. 2C is a graph showing LCMV titers in rapamycin-treated and untreated mice.

Rapamycin is a macrolide with immunosuppressive and anti-proliferative properties. The effect of rapamycin treatment on T cell responses induced by vaccination was evaluated in mice infected with lymphocytic choriomeningitis virus (LCMV). To test the effect of rapamycin treatment on the expansion phase of a T cell response, mice were injected intraperitoneally with $2\times10^5$ plaque forming units (PFU) of LCMV on Day 0 and treated with rapamycin once a day for 9 days, starting one day prior to vaccination (Day −1). Rapamycin was administered intraperitoneally at a dose of 0.6 mg/kg (resulting in blood concentration of approximately 40-100 ng/ml). On Day 8, peripheral blood mononuclear cells (PBMCs) were isolated and evaluated by FACS analysis to determine the percentage of virus-specific CD8+ T cells in rapamycin-treated and untreated mice (FIG. 2A). PBMCs were incubated with antibodies specific for CD8 and CD44 (a memory T cell marker), and a LCMV GP33 epitope-specific MHC class I tetramer (DbGP33; Murali-Krishna et al., *Immunity* 8(2):177-87, 1998). The anti-CD8 antibody was conjugated with the fluorochrome peridinin chlorophyll protein (PerCP) (BD Biosciences) and the anti-CD44 antibody was conjugated with the fluorophore Pacific Blue® (eBioscience, San Diego, Calif.). As shown in FIG. 2B, mice treated with rapamycin during the T cell expansion phase had a smaller percentage of virus-specific CD8+ T cells (2.49%) relative to untreated mice (6.98%), suggesting that rapamycin inhibited antigen-driven T cell proliferation. In addition, LCMV titer in rapamycin-treated mice was significantly increased relative to untreated mice (FIG. 2C), demonstrating the immunosuppressive effect of rapamycin when administered during the T cell expansion phase.

To determine the effect of rapamycin treatment during the T cell maintenance phase, mice were adoptively transferred with carboxyfluorescein succinimidyl ester (CFSE)-labeled GP33 epitope-specific memory CD8+ T cells (TCR-transgenic P14 cells; Pircher et al., *Nature* 342:559-561, 1989). CFSE-labeled cells were transferred intravenously via tail vein injection. Mice were either untreated or treated with rapamycin daily for 43 days at a dose of 0.6 mg/kg, beginning one day prior to adoptive transfer (Day −1) (FIG. 3A). On Day 42, the number of transferred virus-specific CD8+ T cells in the spleen of treated and untreated mice was determined. To isolate spleen lymphocytes, spleens were homogenized and red blood cells were lysed with 0.83% ammonium chloride. Isolated splenocytes were then evaluated by FACS. As shown in FIG. 3B, rapamycin treatment decreased the number of virus-specific CD8+ T cells in the spleen. Proliferation of virus-specific CD8+ T cells was also evaluated on Day 42 by detecting fluorescence intensity of CFSE-labeled T cells by FACS. As shown in FIG. 3C, rapamycin treatment reduced the percentage of virus-specific CD8+ T cells that divided more than twice (17.8%), relative to untreated mice (42.5%).

Figure 4A:
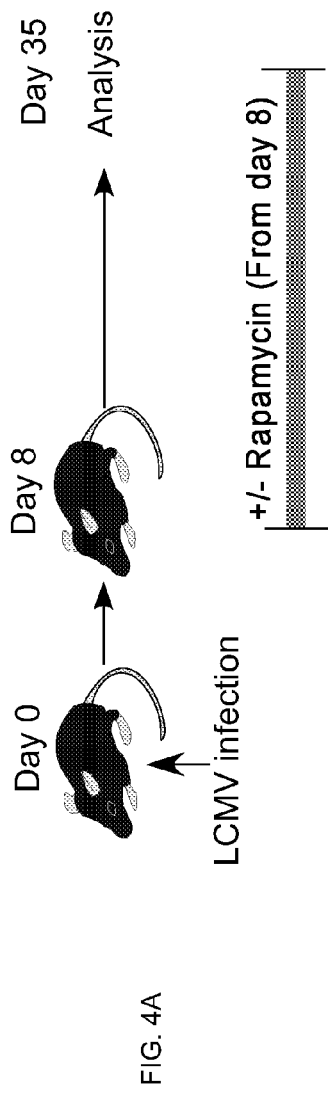
FIG. 4A is a schematic of the experimental design for testing the effect of rapamycin treatment on virus-specific CD8+ T cells during the contraction phase. Mice were infected with LCMV on Day 0 and treated with rapamycin starting on Day 8 after infection. Splenocytes from untreated and rapamycin-treated mice were analyzed on Day 35.
Figure 4B:
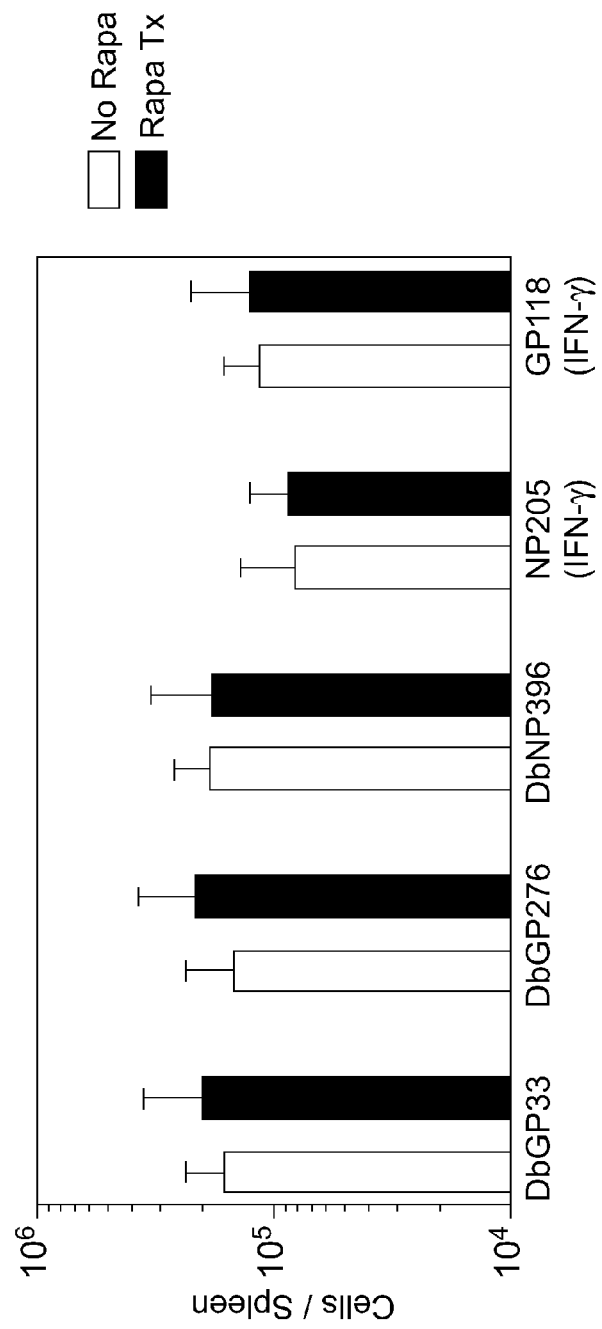
FIG. 4B is a graph showing the number of virus-specific CD8+ T cells obtained from the spleen of untreated and rapamycin-treated mice. Tetramer staining was used to detect GP33, GP276 and NP396 epitope-specific CD8+ T cells, while CD8+ T cells specific for epitopes NP205 and GP118 were detected by IFN-γ staining following peptide stimulation.

To determine the effect of rapamycin treatment during the T cell contraction phase, mice were injected intraperitoneally with $2\times10^5$ PFU of LCMV on Day 0 and administered 0.6 mg/kg of rapamycin daily beginning on Day 8 (FIG. 4A). On Day 35 post-infection, the number of virus-specific CD8+ T cells in the spleen of rapamycin-treated and untreated mice was determined by FACS using anti-CD8 antibody, anti-CD44 antibody and tetramer staining Tetramer staining was used to detect GP33, GP276 and NP396 epitope-specific CD8+ T cells. To detect NP205 and GP118 epitope-specific CD8+ T cells, interferon (IFN)-γ positive cells were measured by intracellular staining after peptide stimulation. As shown in FIG. 4B, rapamycin treatment during the T cell contraction phase did not reduce the number of virus-specific CD8+ T cells.

Thus, in accordance with the known immunosuppressive properties of rapamycin, treatment with rapamycin exhibited an immunosuppressive effect during the T cell expansion (FIG. 2) and maintenance (FIG. 3) phases. However, rapamycin treatment did not alter the number of virus-specific CD8+ T cells during the contraction phase (FIG. 4).

Figure 5A:
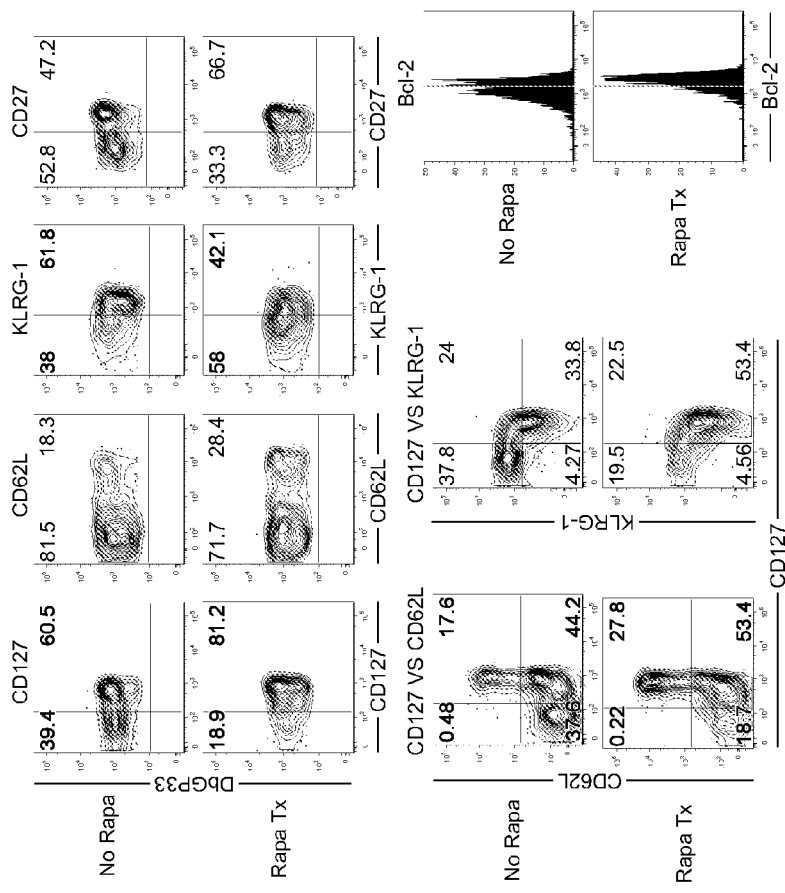
FIG. 5A shows a series of FACS plots evaluating expression of T cell markers (CD127, CD62L, KLRG-1, CD27 and Bcl-2) on splenocytes obtained from untreated and rapamycin-treated mice according to the procedure shown in FIG. 4A.
Figure 6:
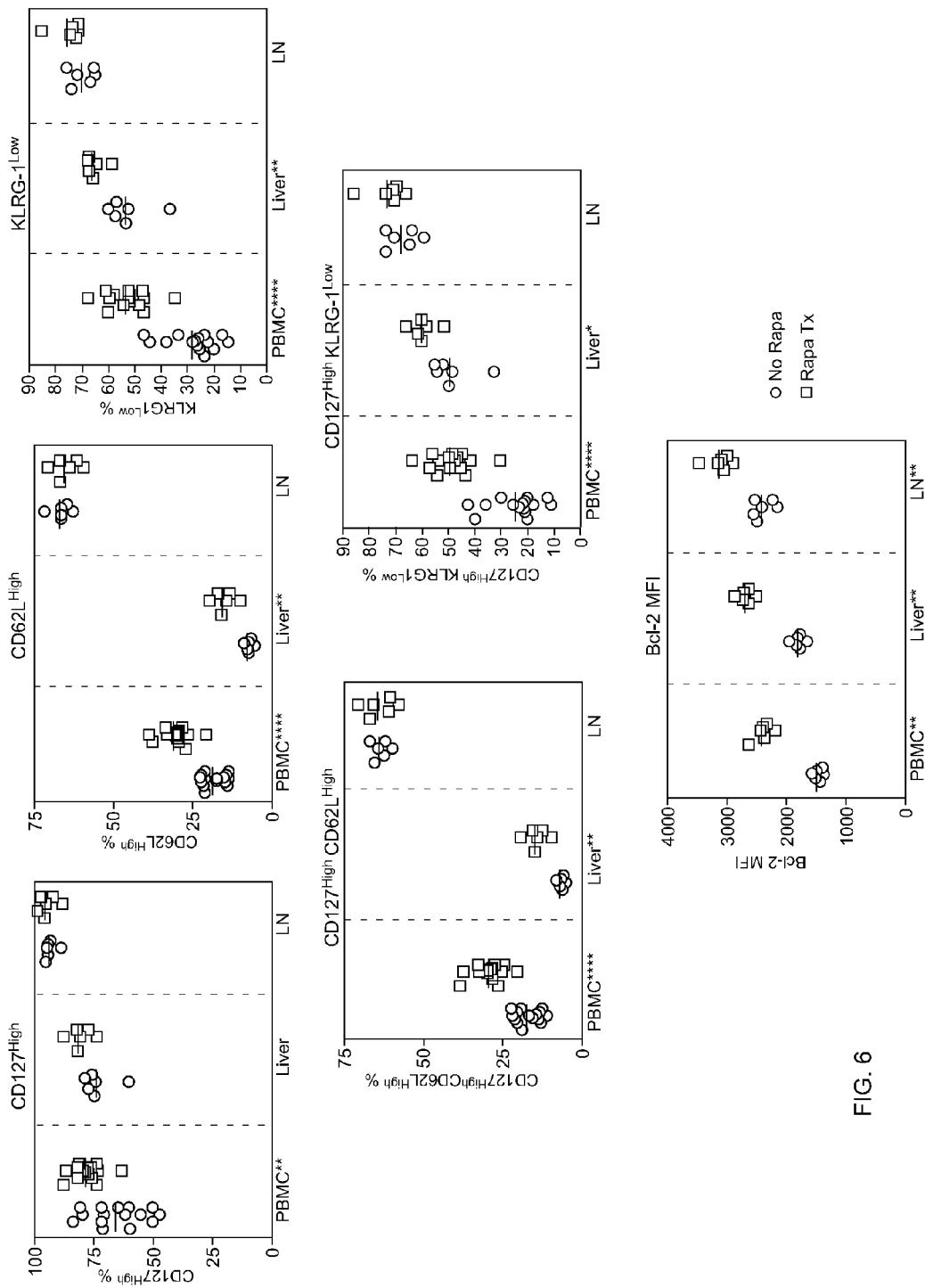
FIG. 6 is a series of graphs showing that rapamycin treatment induces high quality memory T cells during the contraction phase in PBMCs, liver and lymph nodes (LN).

To examine whether rapamycin treatment effects the quality of virus-specific CD8+ T cells during the contraction phase, phenotypic analysis of virus-specific CD8+ T cells in spleen, PBMCs and liver was performed by evaluating markers for high quality memory T cells (including $CD127^{High}$, $CD62L^{High}$, $KLRG-1^{Low}$, $CD27^{High}$ and $Bcl-2^{High}$) by FACS. As shown in FIG. 5, a number of significant differences were identified between control and rapamycin-treated animals. In rapamycin-treated animals, GP33, GP276 and NP396 epitope-specific CD8+ T cells phenotypically showed high quality memory T cells ($CD127^{High}$, $CD62L^{High}$, $KLRG-1^{Low}$, $CD27^{High}$, $Bcl-2^{High}$) compared to untreated animals. In addition to spleen, a similar phenotypic trend of virus-specific CD8+ T cells was identified in PBMCs and liver (FIG. 6). In lymph node, no significant change in cell surface markers was observed between untreated and rapamycin-treated animals (FIG. 6). These results were expected because virus-specific CD8+ T cells in lymph node typically exhibit a high quality phenotype compared to other tissues. However, in rapamycin-treated animals, Bcl-2 expression was higher than control even in lymph node. Taken together, rapamycin treatment during contraction phase enhanced generation of high quality memory T cells.

Figure 7A:
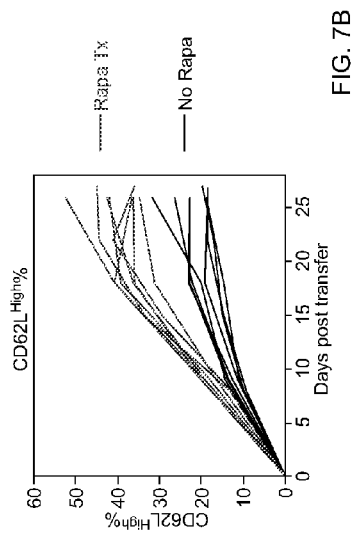
FIG. 7A is a schematic of the experimental design for demonstrating that rapamycin treatment enhances CD62L re-expression during the T cell contraction phase. LCMV-specific transgenic (P14) effector CD8+ T cells (Thy-1.1+) were isolated on Day 8 post-infection. CD62L$^{high}$ cells were depleted from the isolated effector P14 cells and the remaining CD62L$^{low}$ effector CD8+ T cells were transferred into Thy-1.2+ naïve mice. Mice were then treated with rapamycin daily.
Figure 7B:
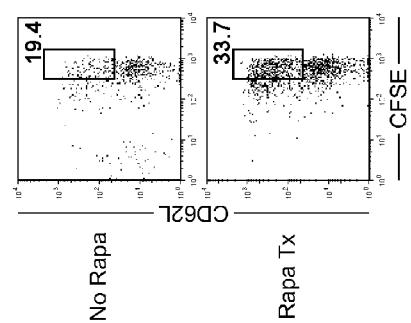
FIG. 7B is a graph showing conversion of CD62L expression from low to high in PBMC from Day 0 to Day 26 post-transfer.
Figure 7C:
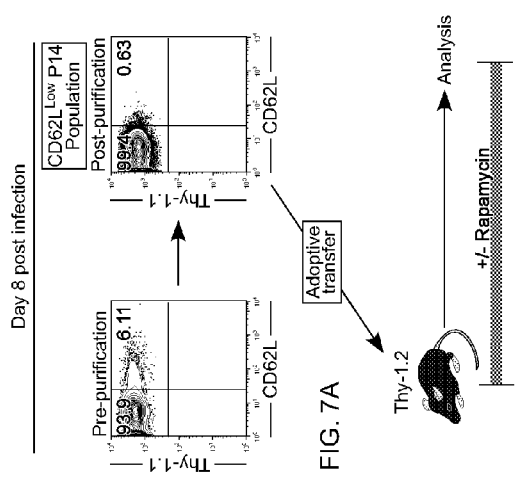
FIG. 7C is a graph showing the number of CD62L$^{high}$ P14 cells in the spleen of untreated and rapamycin-treated mice on Day 26 post-transfer.
Figure 7D:
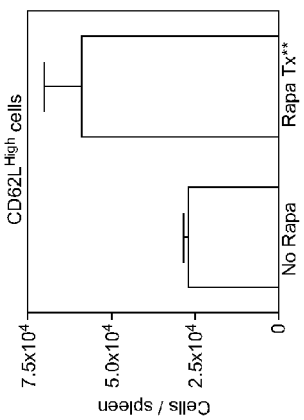
FIG. 7D shows FACS plots of CD62L expression of Thy-1.1+ P14 cells on Day 26 post-transfer. The percentage of cells that are CFSE-$^{high}$ (cells that have not divided) and CD62L$^{high}$ is indicated.

The results described above indicate that rapamycin treatment induces high quality memory T cells during the T cell contraction phase. To investigate how rapamycin accumulates high quality memory T cells, CD62L-negative virus-specific effector T cells were transferred into naïve mice as described below and illustrated in FIG. 7A. LCMV-specific transgenic (P14) effector CD8+ T cells (Thy-1.1+) were isolated from transgenic P14 mice (fully backcrossed with C57BL/6 mice) on Day 8 after LCMV infection. $CD62L^{high}$ cells were depleted from the isolated effector P14 cells using microbeads (Miltenyi Biotec, Auburn, Calif.) (Wherry et al., *Nat. Immunol.* 4(3):225-234, 2003). The remaining $CD62L^{low}$ effector CD8+ T cells were transferred into Thy-1.2+ naïve mice. Mice were then left untreated or treated with 0.6 mg/kg rapamycin daily for 26 days. In some experiments, Day 8 effector P14 cells were labeled with CFSE. Virus-specific CD8+ T cells in rapamycin-treated mice quickly re-expressed CD62L compared with control mice (FIG. 7B), and the absolute number of $CD62L^{High}$ virus-specific CD8+ T cells was greater in rapamycin-treated mice (FIG. 7C). In addition, CD62L re-expression occurred with no or minimal cell division. Therefore, when CFSE-labeled CD62L negative effector T cells were transferred, most cells still retained CFSE 26 days post transfer (FIG. 7D). These results demonstrate that rapamycin treatment enhances CD62L re-expression without cell division during the contraction phase. Furthermore, these data suggest that rapamycin treatment improves differentiation of memory T cells during the contraction phase.

Next, studies were undertaken to determine whether rapamycin-induced memory T cells are effective for rapidly controlling virus infection. To address this issue, the following experiments were designed. CD62L-negative LCMV-specific effector CD8$^+$ T cells (Day 8 effector P14 cells) were transferred into naïve mice. These mice were either left untreated or treated with rapamycin for 25 days, then challenged with vaccinia virus (VV) that expresses the GP33 epitope (VVgp33; Wherry et al., *Nat. Immunol.* 4(3):225-234, 2003) on Day 28 (FIG. 8A). VVgp33 was administered intraperitoneally at a dose of 5×10$^6$ PFU. To evaluate the T cell recall response, the percentage of virus-specific CD8$^+$ T cells in the spleen was determined by FACS on Day 5 after VV challenge. As shown in FIG. 8B, a greater percentage of virus-specific CD8$^+$ T cells (DbGP33 tetramer-positive P14 cells) was detected in rapamycin treated mice (4.93%) relative to untreated mice (1.69%). In addition, the absolute number of DbGP33 tetramer-positive P14 cells was greater in rapamycin-treated mice than in untreated mice (FIG. 8C), suggesting that rapamycin-induced memory T cells expanded rapidly compared with control.

To evaluate the effect of rapamycin treatment on virus infection, viral titers were determined in the ovaries of naïve mice, untreated mice and rapamycin-treated mice on Day 5 post-challenge. As shown in FIG. 8D, rapamycin treatment led to a reduction in viral titer relative to untreated and naïve mice. These results suggest that rapamycin-induced memory CD8$^+$ T cells are high quality memory T cells capable of effectively inhibiting virus infection.

In addition to better viral control, homeostatic proliferation is another characteristic of high quality memory T cells. To investigate the ability of rapamycin induced memory T cells to undergo homeostatic proliferation, CFSE-labeled memory T cells derived from rapamycin-treated or untreated mice were adoptively transferred into naïve mice (FIG. 9A). As shown in FIG. 9B, the percentage of divided memory T cells in PBMC was increased with rapamycin treatment. Cell division of P14 memory cells was also evaluated in the spleen 30 days post-transfer. As shown in FIG. 9C, rapamycin treatment increased the percentage of cells that divided more than twice (46.1%), relative to the control (36.8%). These data demonstrate that rapamycin-treated memory T cells exhibit better homeostatic proliferation in both PBMC and spleen, suggesting that rapamycin induces effective memory T cells. Taken together, rapamycin-induced memory CD8$^+$ T cells are bona fide high quality memory T cells.

Figure 10A:
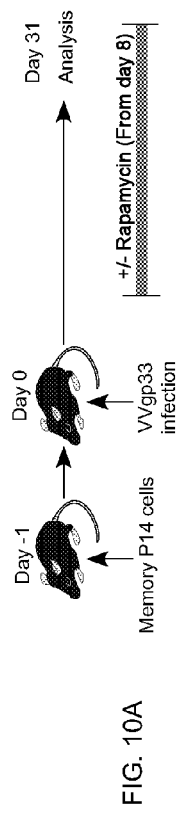
FIG. 10A is a schematic of the experimental design to demonstrate that rapamycin treatment enhances high quality memory T cells during the contraction phase of recall responses. LCMV-specific memory P14 cells were transferred into naïve mice on Day −1. The next day, mice were infected with VVgp33 and either untreated or treated with rapamycin daily from Day 8 post-infection.
Figure 10B:
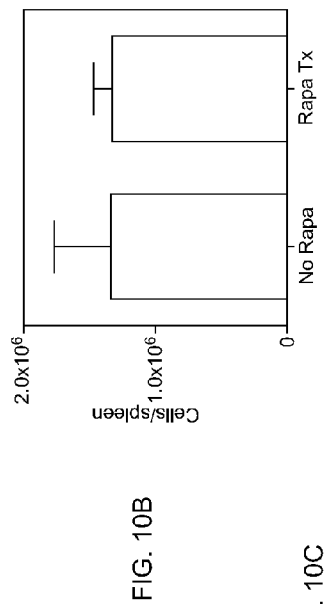
FIG. 10B is a graph showing the number of P14 cells in the spleen of untreated and rapamycin-treated mice on Day 31.
Figure 10C:
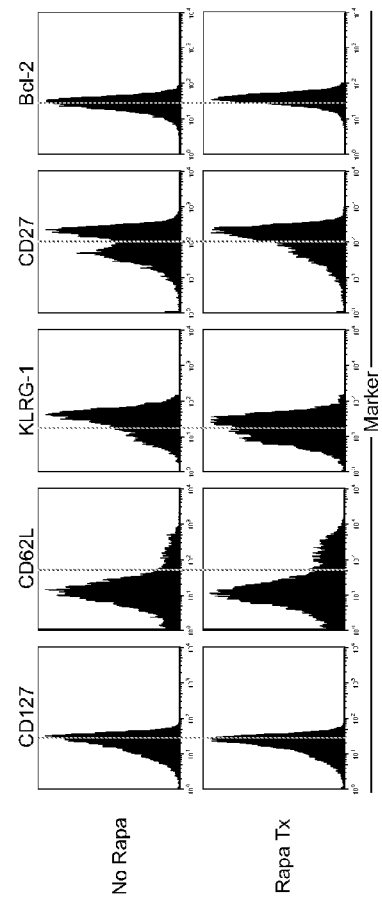
FIG. 10C is a series of FACS plots showing the phenotypic differences of P14 cells on Day 31 post-infection in the spleen, as measured by expression of high quality T cell markers CD127, CD62L, KLRG-1, CD27 and Bcl-2.

Next, experiments were performed to determine whether rapamycin has any effect on virus-specific CD8$^+$ T cells after a recall response. To investigate this, mice were treated with 0.6 mg/kg rapamycin during the contraction phase of a recall response. LCMV-specific memory P14 cells were transferred into naïve mice on Day −1. On Day 0, mice were infected with 5×10$^6$ PFU VV 33. Mice were either untreated or treated with rapamycin each day starting on Day 8 after VV infection (FIG. 10A). The number of P14 cells in the spleen of untreated and rapamycin-treated mice was determined on Day 31 post-infection by FACS. As shown in FIG. 10B and FIG. 10C, the number of virus-specific CD8$^+$ T cells was similar between control and rapamycin-treated animals and there was no significant difference in CD127 and CD62L expression. However, expression of KLRG-1 was lower and expression of CD27 and Bcl-2 was higher on virus-specific CD8$^+$ T cells from rapamycin-treated mice, relative to control mice (FIG. 10C). These results suggest that rapamycin enhances high quality memory T cells during the contraction phase of T cell recall responses.

Example 2

Low Dose Rapamycin Treatment Enhances the Number of Antigen-Specific CD8$^+$ T Cells and Induces High Quality Memory T Cells As described above, rapamycin treatment during the T cell expansion phase inhibits antigen-driven T cell proliferation. This example describes the effect of a lower dose of rapamycin on T cell responses. In particular, this example demonstrates that low dose rapamycin treatment (i) enhances the number of virus-specific CD8$^+$ T cells; (ii) induces high quality memory T cells during a primary T cell response; (iii) induces high quality memory T cells during a recall response; and (iv) induces high quality memory T cells upon immunization with a non-infectious immunogen.

Mice were injected intraperitoneally with 2×10$^6$ PFU LCMV on Day 0 and treated daily with a low dose of rapamycin (0.075 mg/kg, which results in a blood concentration of approximately 5-20 ng/ml) beginning one day prior to infection (Day −1) (FIG. 11A). To evaluate the number of virus-specific CD8$^+$ T cells in untreated and rapamycin-treated mice, PBMCs were isolated and subjected to FACS analysis. As shown in FIG. 11B, a similar number of GP33 epitope-specific CD8$^+$ T cells was detected in PBMCs from treated and untreated mice isolated on Day 8 post-infection. However, mice treated with low dose rapamycin maintained a higher number of GP33 epitope-specific CD8$^+$ T cells compared to untreated animals from Day 8 until the conclusion of the 30-day evaluation period. Also examined was the number of virus-specific CD8$^+$ T cells in the spleen of untreated and rapamycin-treated mice 35 days post-infection. Tetramer staining was used to detect GP33, GP276 and NP396 epitope-specific CD8$^+$ T cells. For NP205 and GP118 epitope-specific CD8$^+$ T cells, IFN-γ positive cells were measured by intracellular staining after peptide stimulation. As shown in FIG. 11C, rapamycin treatment enhanced the number of all epitope-specific CD8$^+$ T cells examined.

To investigate the quality of virus-specific CD8$^+$ T cells in low dose rapamycin-treated mice, phenotypic analysis of T cells was performed by FACS as described above. As shown in FIG. 12, there were significant differences between control and rapamycin-treated animals. In treated animals, virus-specific CD8$^+$ T cells exhibited a CD127$^{High}$ CD62L$^{High}$ KLRG-1$^{Low}$ Bcl-2$^{High}$ phenotype compared to untreated mice (FIG. 12A and FIG. 12B). These differences were detected by Day 8 post-infection (FIG. 12C). These data suggest that rapamycin regulates phenotypic changes during T cell differentiation. In addition, these results suggest that low dose rapamycin treatment induces high quality memory T cells.

Figure 13A:
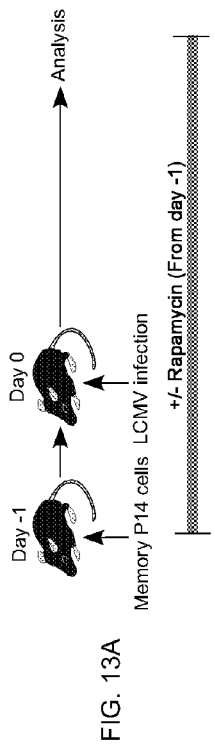
FIG. 13A is a schematic of the experimental design to demonstrate that low dose rapamycin treatment induces high quality memory T cells during recall responses. Thy-1.1+ P14 memory T cells were adoptively transferred into Thy-1.2+ recipient mice and low dose rapamycin treatment was initiated on the same day (Day −1). The following day (Day 0), recipient mice were infected with LCMV.
Figure 13B:
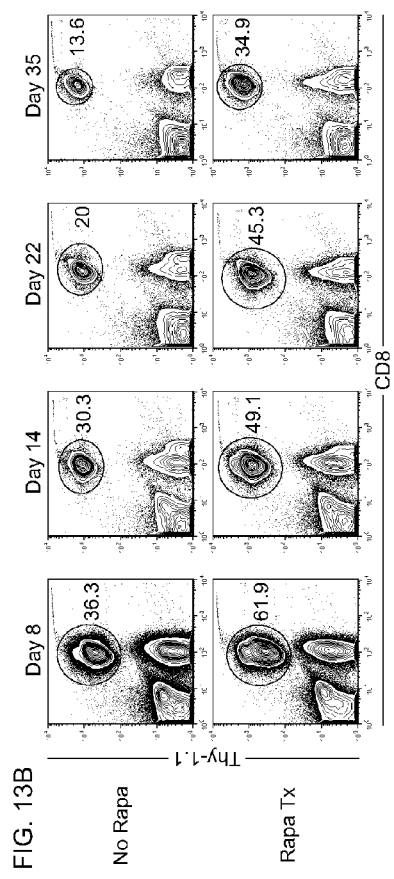
FIG. 13B is a series of FACS plots showing LCMV-specific CD8+ T cell responses after infection. Shown is the percentage of Thy- 1.1+ P14 cells in PBMCs obtained from untreated and rapamycin-treated mice on Days 8, 14, 22 and 35 post-infection.
Figure 13C:
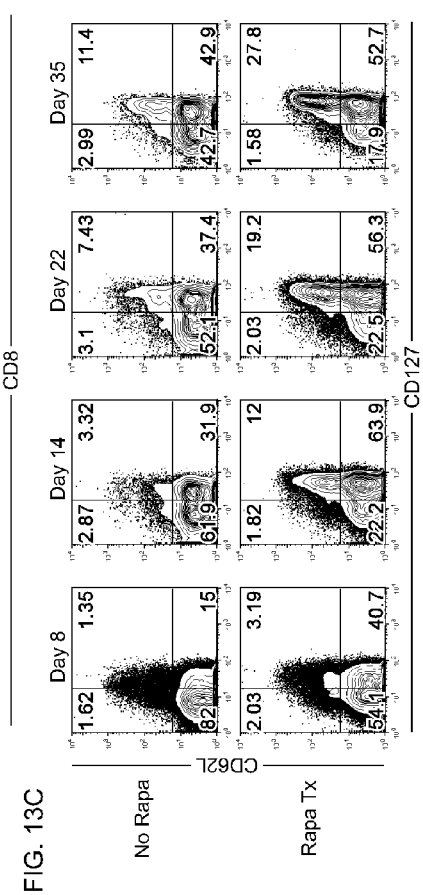
FIG. 13C is a series of FACS plots showing the percentage of LCMV-specific CD8+ T cells expressing CD62L and CD127 on Days 8, 14, 22 and 35 post-infection.

Next, the effect of low dose rapamycin treatment on virus-specific CD8$^+$ T cells after a recall response was evaluated. To investigate this, mice were treated with a low dose of rapamycin (0.075 mg/kg) during recall responses. Thy-1.1$^+$ P14 memory cells were adoptively transferred into Thy-1.2$^+$ recipient mice and rapamycin treatment was initiated on the same day (Day −1). The next day (Day 0), recipient mice were injected intraperitoneally with 2×10$^6$ PFU LCMV (FIG. 13A). The percentage of LCMV-specific CD8$^+$ T cells in PBMCs isolated from treated and untreated mice on Days 8, 14, 22 and 35 was evaluated by FACS. As shown in FIG. 13B, the percentage of virus-specific CD8⁺ T cells was greater in rapamycin treated animals than in control mice at each day tested. Moreover, rapamycin treatment enhanced expression of CD127 and CD62L (FIG. 13C). These results indicate that low dose rapamycin induces high quality memory T cells during recall responses as well as primary responses.

To determine whether low dose rapamycin treatment has an effect on T cell responses against noninfectious immunogens, virus-like particles (VLPs) that present GP33 epitope were used to immunize mice (Storni et al., *J. Immunol.* 168 (6):2880-2886, 2002; Storni et al., *J. Immunol.* 171(2):795-801, 2003). Mice were immunized with 50 μg of VLPs by subcutaneous injection, and mice were either untreated or treated with rapamycin beginning one day prior to immunization (Day −1) (FIG. 14A). After VLP immunization, GP33 epitope-specific CD8⁺ T cells expanded similarly in the rapamycin-treated and control groups (FIG. 14B). However, rapamycin-treated mice maintained a higher number of antigen-specific CD8⁺ T cells compared to control in PBMC (FIG. 14B) and spleen (FIG. 14C). In addition, the phenotype of antigen-specific CD8⁺ T cells isolated from the spleen of rapamycin-treated mice 34 days post-infection exhibited markers of high quality memory T cells ($CD127^{High}$, $CD62L^{High}$, $KLRG-1^{Low}$, $Bcl-2^{High}$) (FIG. 14D and FIG. 14E). These results suggest that low dose rapamycin induces high quality memory T cells not only upon infection, but also upon immunization with non-infectious immunogen.

Example 3

Figure 15:
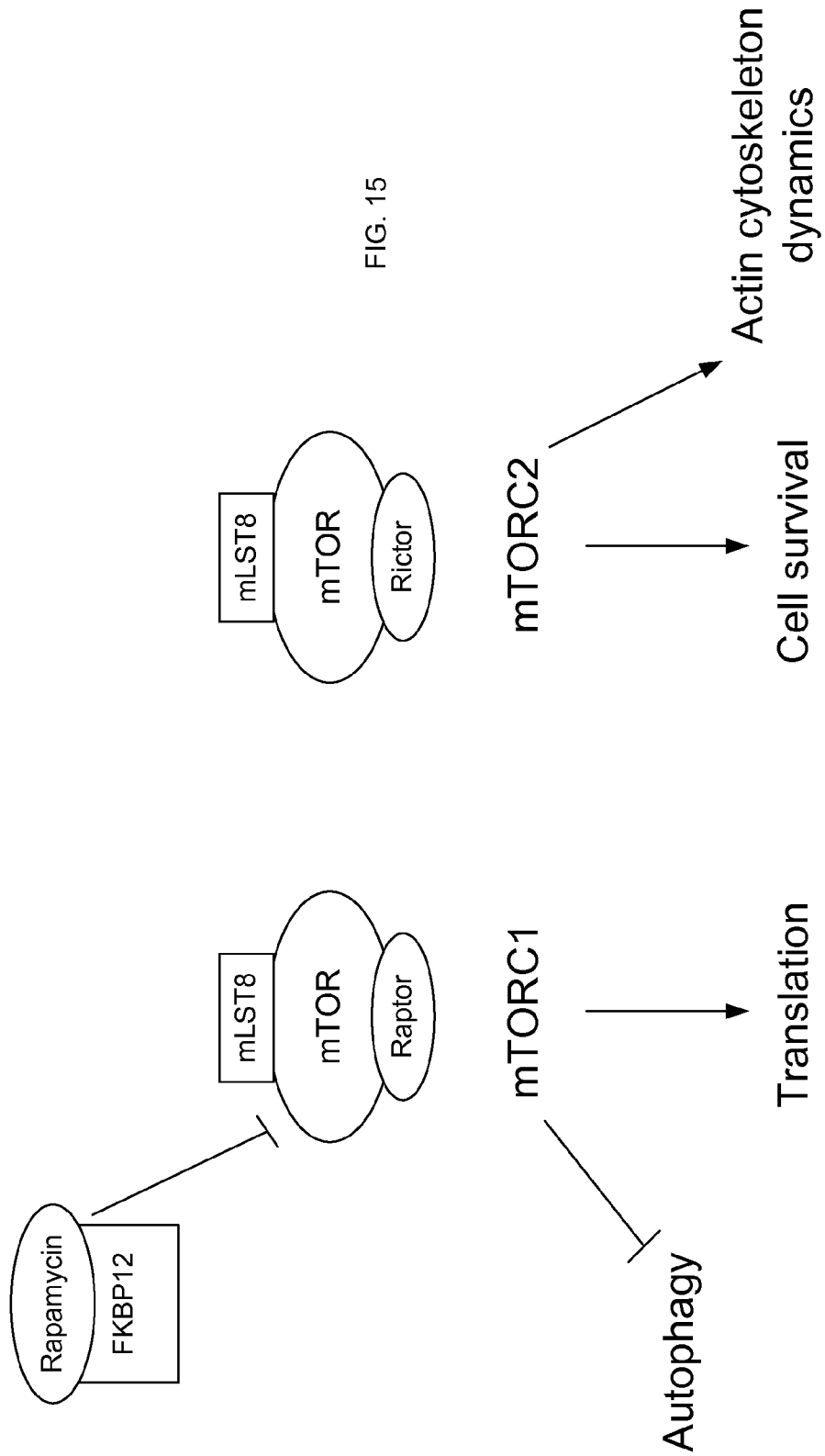
FIG. 15 is a schematic depiction of the mammalian target of rapamycin (mTOR) pathway. mTOR is part of two distinct complexes, mTOR complex 1 (mTORC1) and complex 2 (mTORC2). mTORC1 is sensitive to rapamycin.
Figures 16A, 16B:
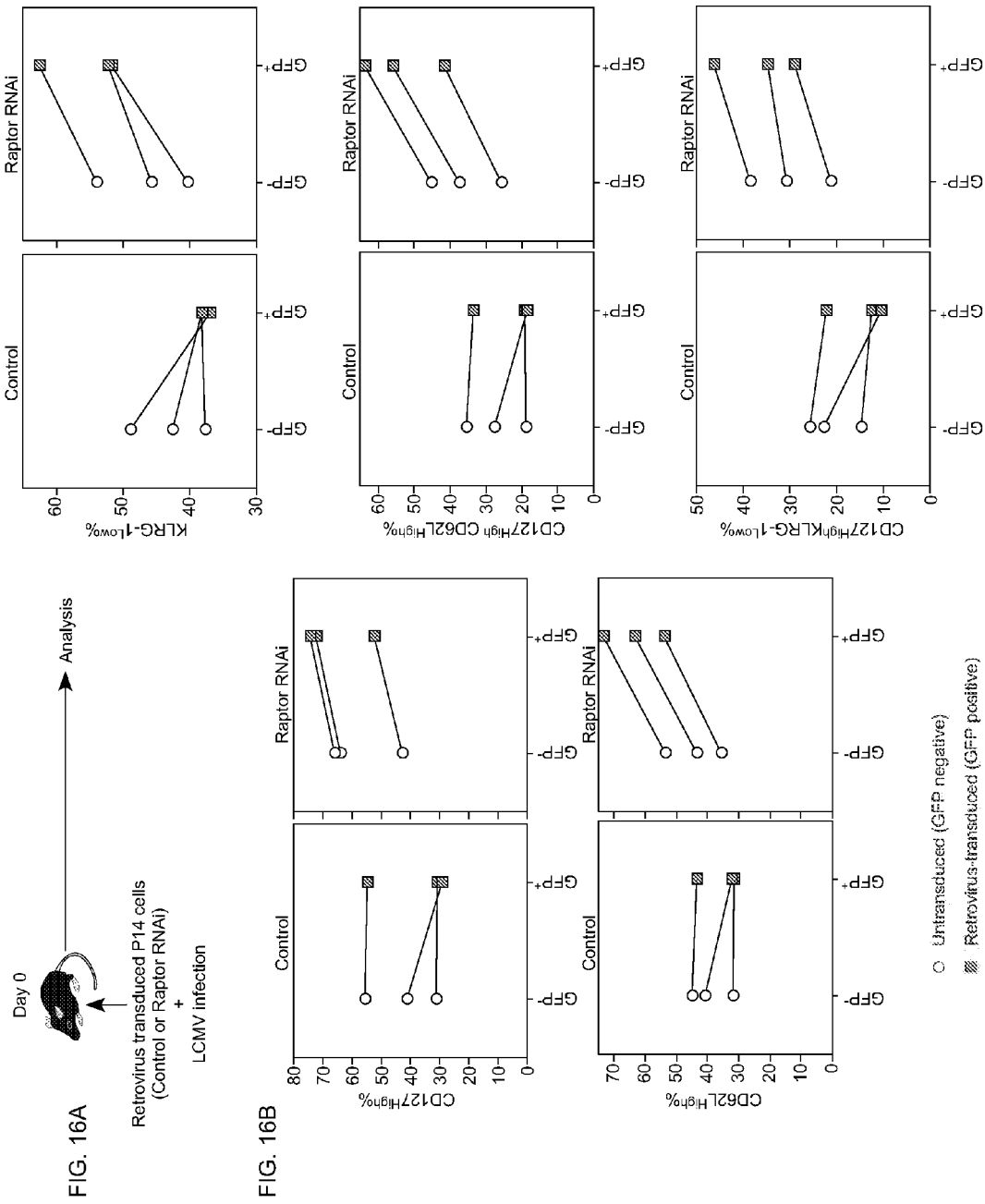
FIG. 16A is a schematic of the experimental design for raptor knockdown in virus-specific CD8+ T cells. Retrovirus encoding a control or raptor-specific short hairpin RNA (shRNA) (RNAi) was constructed and used to transduce LCMV-specific P14 cells. Transduced P14 cells were adoptively transferred into naïve mice, and the mice were then infected with LCMV.
FIG. 16B is a series of graphs showing the phenotypic changes of adoptively transferred P14 cells obtained from the spleen on Day 35 after LCMV infection. GFP-positive cells are retrovirus-transduced cells.

Rapamycin Intrinsically Affects Virus-Specific CD8⁺ T Cells for Generation of High Quality Memory T Cells and Enhances the Number of Virus-Specific Memory CD4⁺ T Cells It is known in the art that rapamycin inhibits mTOR, which is ubiquitously expressed and plays a role in a number of cellular processes, including translation, cell survival, autophagy and actin cytoskeleton dynamics. Therefore, it is possible that rapamycin not only affects T cells, but also non-T cells in vivo. How rapamycin induces high quality memory T cells in vivo was previously unknown. To test whether generation of high quality memory T cells by rapamycin is a CD8-intrinsic effect, knockdown of rapamycin-related molecules was performed using a retrovirus-based RNA interference (RNAi) system. mTOR is part of two distinct complexes, mTOR complex 1 (mTORC1) and mTOR complex 2 (mTORC2) (FIG. 15). Recent studies suggest that mTORC1 is sensitive to rapamycin. Therefore, to inhibit the mTORC1 pathway, experiments were performed to inhibit expression of raptor, which is part of mTORC1 (FIG. 16A).

Retrovirus encoding a control or raptor shRNA (GCCCGAGTCTGTGAATGTAAT; SEQ ID NO: 1) was constructed by cloning the shRNA into the pMKO.1-GFP retrovirus vector (Addgene, Cambridge, Mass.). Retrovirus was generated by co-transfection of pMKO.1-GFP-raptor (or pMKO.1-GFP-control) and pCL-Eco (packaging vector) plasmid into HEK-293T cells. For transduction, P14 transgenic mice were infected with 1×10⁶ PFU LCMV intravenously. One day later, activated splenocytes were spin-transduced with freshly made retroviral supernatants from HEK-293T cells (90 minutes at 37° C., 3000 rpm). After transduction, transduced splenocytes were adoptively transferred intravenously to naïve recipient mice that were subsequently infected intraperitoneally with LCMV at a dose of 2×10⁵ PFU. Virus-specific memory T cell phenotype in mouse spleen was evaluated in control and raptor RNAi-treated animals 35 days post-infection by FACS. Raptor knockdown resulted in a high quality memory T cell phenotype ($CD127^{High}$, $CD62L^{High}$ $KLRG-1^{Low}$) in LCMV-infected mice (FIG. 16B).

A FKBP12 knockdown-retrovirus vector was also constructed by cloning the FKBP12 shRNA (GCCAAACTGATAATCTCCTCA; SEQ ID NO: 2) into the pMKO.1-GFP retrovirus vector (Addgene). FKBP12 forms a complex with rapamycin, and this complex inhibits mTORC1 (FIG. 15). Thus, virus-specific CD8⁺ T cells with FKBP12 knockdown should be rapamycin insensitive. To test this hypothesis, retrovirus-transduced LCMV-specific P14 cells were adoptively transferred into naïve mice and mice were then infected with LCMV at a dose of 2×10⁵ PFU. Rapamycin treatment (0.075 mg/kg) was initiated one day prior to infection (FIG. 17A). The phenotypic changes of adoptively transferred P14 cells were evaluated by FACS on Day 16 post-infection in PBMC. As shown in FIG. 17B, the effect of rapamycin treatment was diminished by FKBP12 knockdown. Taken together, these results demonstrate that rapamycin intrinsically affects virus-specific CD8⁺ T cells for generation of high quality memory T cells.

Figure 18:
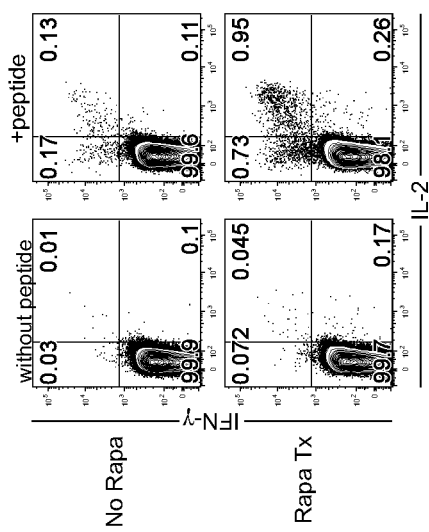
FIG. 18 shows FACS plots demonstrating that low dose rapamycin treatment enhances the number of virus-specific memory CD4+ T cells. Rapamycin treatment was initiated one day prior to infection with LCMV. Spleen cells were stimulated with LCMV GP61 peptide specific for CD4+ T cells and intracellular cytokine staining was performed. The percentage of CD4+ T cells expressing IL-2 and/or IFN-γ in the presence and absence of peptide stimulation is indicated.

In addition to CD8⁺ T cells, low dose rapamycin treatment enhanced the number of virus-specific memory CD4⁺ T cells (FIG. 18). Mice were infected with 2×10⁵ PFU LCMV on Day 0 and were either untreated or treated with rapamycin beginning one day prior to infection (Day −1). Spleen cells were isolated on Day 35 and stimulated with LCMV GP61 peptide specific for CD4⁺ T cells. Intracellular cytokine (IL-2 and IFN-γ) staining was performed and the cells were subjected to FACS. As shown in FIG. 18, rapamycin treatment resulted in a higher number of IFN-γ⁺ cells upon peptide stimulation relative to cells from untreated mice.

Example 4

Low Dose Rapamycin Treatment Improves Quantity and Quality of Memory T Cells This example describes the finding that low dose rapamycin treatment improves the quantity and quality of memory T cells generated by recombinant adenovirus serotype 5 (rAd5) that expresses LCMV glycoprotein (rAd5-LCMV-GP). The nucleotide and amino acid sequences of LCMV GP, deposited under GENBANK™ Accession No. M20869 on Aug. 2, 1993, are set forth herein as SEQ ID NOs: 7 and 8, respectively.

Figure 19A:
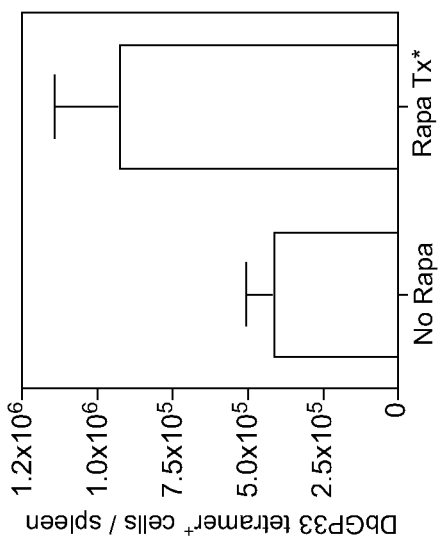
FIG. 19A is a schematic of the experimental design to demonstrate that low dose rapamycin treatment improves the quantity and quality of memory T cells induced by recombinant adenovirus serotype 5 (rAd5) that expresses LCMV glycoprotein (rAd5-LCMV-GP). Rapamycin treatment was initiated one day prior to vaccination with rAd5-LCMV-GP.
Figure 19B:
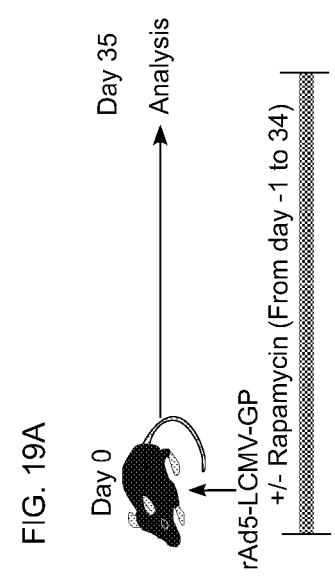
FIG. 19B is a graph showing the number of DbGP33 tetramer-positive CD8+ T cells in the spleen on Day 35 post-vaccination.
Figure 19C:
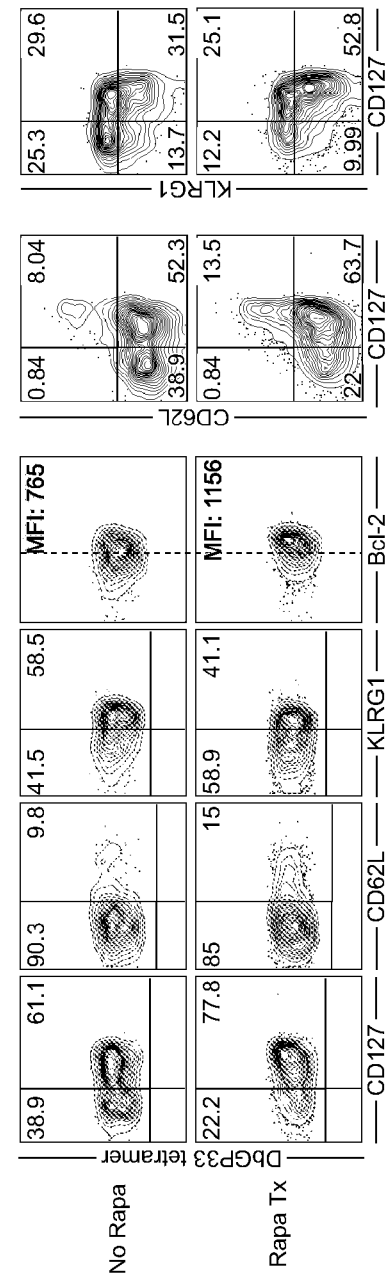
FIG. 19C is a series of FACS plots showing phenotypic analysis of DbGP33 tetramer-positive CD8+ T cells in the spleen on Day 35 post-vaccination.

Mice were vaccinated with rAd5-LCMV-GP (1×10¹⁰ viral particles) by intramuscular injection on Day 0 and either left untreated or treated with rapamycin at a dose of 0.075 mg/kg from Day −1 to Day 34 (FIG. 19A). The number of DbGP33 tetramer-positive CD8⁺ T cells in the spleen of treated and untreated mice was determined by FACS on Day 35 post-vaccination. As shown in FIG. 19B, rapamycin treatment significantly increased the number of virus-specific CD8⁺ T cells. The phenotype of virus-specific CD8⁺ T cells was also evaluated by FACS (FIG. 19C). In accordance with data described above, CD8⁺ T cells from rapamycin-treated mice exhibited markers of high quality memory T cells ($CD127^{High}$, $CD62L^{High}$, $KLRG-1^{Low}$, $Bcl-2^{High}$).

Example 5 mTOR Regulates Memory CD8⁺ T Cell Differentiation

Rapamycin is a commonly used immunosuppressive drug in transplant recipients and specifically inhibits the intracellular kinase mTOR (Wullschleger et al., Cell 124:471-484, 2006). Several recent studies have shown that rapamycin has various effects on the immune system such as inhibiting type I interferon production by plasmacytoid dendritic cells (Cao et al., Nat Immunol 9(10):1157-1164, 2008), modulating T cell trafficking (Sinclair et al., Nat Immunol 9(5):513-521, 2008), and regulating Foxp3 expression in regulatory T cells (Sauer et al., Proc Natl Acad Sci USA 105:7797-7802, 2008; Haxhinasto et al., J Exp Med 205:565-574, 2008). However, the role of the mTOR pathway in regulating $CD8^+$ T cell responses is not known. To address this issue, the following experiments were performed.

Materials and Methods

Mice, viral infection, VLP, and virus titrations. Twelve- to sixteen-week old C57BL/6j mice were purchased from The Jackson Laboratory (Bar Harbor, Me.). Thy-1.1 P14 transgenic mice bearing the DbGP33-specific TCR were fully backcrossed to C57BL/6 mice in the animal colony. LCMV Armstrong ($2 \times 10^5$ PFU, IP) and recombinant vaccinia virus GP33 (VVGP33, $5 \times 10^6$ PFU, IP), which expresses the LCMV GP33 epitope, were used for infection. VVGP33 titers were determined in the ovary by plaque assay as described previously (Wherry et al., Nat Immunol 4, 225-234, 2003). For VLP immunization, mice were subcutaneously administered 50 µg of VLP, which was derived from the hepatitis B core antigen (HBcAg) genetically fused to the LCMV 33-41 epitope (KAVYNFATM; SEQ ID NO: 9) and packaged with CpG-ODN.

Administration of rapamycin in mice. Rapamycin (Wyeth, Madison, N.J.) was administered to mice IP daily during the treatment period. Three different treatment periods were used: 1) throughout LCMV infection (Day −1 to the memory phase, Day 35 post-infection); 2) the T cell expansion phase (Day −1 to Day 8 post-infection); or 3) T cell contraction phase (Day 8 to the memory phase, Day 35 post-infection). The daily dose of rapamycin was 75 µg/kg (blood levels approximately 5-20 ng/ml) for treatments 1) and 2) and 600 µg/kg (blood levels approximately 40-100 ng/ml) for treatment 3) (the contraction phase treatment) because the higher dose inhibits T cell responses during the expansion phase of the $CD8^+$ T cell response (as evidenced by a decrease in antigen-specific $CD8^+$ T cells). Control mice received sham treatment during the same time periods described above (daily injection of the buffer without rapamycin).

Rhesus macaques and vaccination. Six colony-bred, SPF Rhesus macaques (Macaca mulatta) were inoculated with DRYVAX™ (Wyeth, Madison, N.J.) by scarification. Briefly, a bifurcated needle was immersed in the vaccine suspension and used to poke the skin 15 consecutive times. At 105 days post DRYVAX™ vaccination, animals were vaccinated with $10^8$ PFU Modified Vaccinia Ankara (MVA) vaccine intramuscularly.

Administration of rapamycin in rhesus macaques. Daily administration of rapamycin (approximately 10-50 µg/kg/day) was given intramuscularly to three of the six DRYVAX™ immunized rhesus macaques approximately 5 days before MVA vaccination. Blood levels of rapamycin were maintained within a range of about 5-15 ng/ml. The other three macaques were left untreated as controls.

Generation and isolation of effector and memory T cell subsets. To generate LCMV-specific P14 effector T cells, mice adoptively transferred with $1 \times 10^5$ P14 naïve T cells were infected with LCMV. On Day 8 post-infection, effector P14 cells were isolated from the spleen, and CD62L-negative $CD8^+$ T cells were purified using anti-CD62L magnetic beads and a $CD8^+$ T cell isolation kit (Miltenyi Biotec, Auburn, Calif.). These cells were then used for a CD62L conversion experiment and a protective immune response experiment. For the CD62L conversion experiment, CFSE-labeled CD62L-negative P14 effector cells (about $7-10 \times 10^6$ cells) were adoptively transferred into naïve mice. For the protective immune response experiment, $3 \times 10^5$ CD62L-negative P14 effector cells were adoptively transferred into naïve mice, and rapamycin was administered for 25 days. On Day 28 post-transfer, mice were challenged with VVGP33 to examine protective immune responses.

To obtain memory P14 cells generated in rapamycin treated mice, B6 mice adoptively transferred with $1 \times 10^5$ P14 naïve T cells were infected with LCMV, and these mice were then treated with rapamycin from Day −1 to Day 33 post-infection. On Day 34 post-infection, memory P14 T cells generated in the presence of rapamycin were isolated from the spleen. Control memory P14 cells were obtained using the same method without the rapamycin treatment. For the homeostatic experiment, CFSE-labeled memory P14 cells ($1 \times 10^6$ cells) obtained from either rapamycin-treated or untreated mice were adoptively transferred into separate naïve recipients. For the recall response experiment, $1 \times 10^4$ P14 memory T cells derived from either rapamycin-treated or untreated mice were adoptively transferred into separate naïve mice, and the day after transfer these mice were infected with VVGP33. To investigate effects of rapamycin during secondary T cell responses, $2.5 \times 10^4$ P14 memory T cells (>60 days post infection) were adoptively transferred into naïve mice, and rapamycin treatment was started. The day after transfer, these mice were infected LCMV.

Flow cytometry. MHC class I tetramers were made as described previously (Murali-Krishna et al., Immunity 8, 177-187, 1998). All antibodies for flow cytometry were purchased from BD Biosciences except for CD127, KLRG-1, and CD27. Antibodies to CD127 and CD27 were purchased from eBiosciences (San Diego, Calif.) and anti-KLRG-1 was purchased from Southern Biotech (Birmingham, Ala.). Single cell suspensions of spleen cells, lymph nodes, livers, or PBMCs from mice were prepared and direct ex-vivo staining was carried out as described previously (Wherry et al., Nat Immunol 4, 225-234, 2003). For in vivo BrdU incorporation, LCMV-infected mice were fed 0.8 mg/ml BrdU in their drinking water every day. BrdU in virus-specific $CD8^+$ T cells was measured using the BrdU flow kit (BD Biosciences), according to the manufacturer's instructions. To detect vaccinia virus-specific $CD8^+$ T cells generated in rhesus macaques, $1.5 \times 10^6$ PBMCs isolated by density gradient centrifugation were incubated at 37° C. for 15 hours with vaccinia virus at a multiplicity of infection of 1 in a volume of 300 µl RPMI containing 10% heat inactivated FBS. Brefeldin A (5 µg/mL) was added for the final 5 hours of incubation. IFN-γ producing vaccinia virus-specific $CD8^+$ T cells were detected by intracellular cytokine staining Retrovirus based RNAi. The pMKO.1 GFP retroviral vector (Addgene plasmid 10676, Cambridge, Mass.) was used for these experiments. Double stranded oligonucleotides for short hairpin RNA (shRNA) against mTOR, raptor, and FKBP 12 were cloned into pMKO.1 GFP between the AgeI and EcoRI restriction sites. The sequences for mTOR, raptor, FKBP12, S6K1 and eIF4E shRNAs are shown in Table 4.

TABLE 4 shRNAs specific for mTOR, raptor, FKBP12, S6K1 and eIF4E

| Target | Sense/Antisense | Sequence | SEQ ID NO: |
|---|---|---|---|
| mTOR | Sense | CCGGGCCAGAATCCATCCAT TCATTCTCGAGAATGAATGG ATGGATTCTGGCTTTTTG | 10 |

TABLE 4-continued shRNAs specific for mTOR, raptor, FKBP12, S6K1 and eIF4E

| Target | Sense/Antisense | Sequence | SEQ ID NO: |
|---|---|---|---|
| mTOR | Antisense | AATTCAAAAAGCCAGAATCC ATCCATTCATTCTCGAGAAT GAATGGATGGATTCTGGC | 11 |
| Raptor | Sense | CCGGGCCCGAGTCTGTGAAT GTAATCTCGAGATTACATTC ACAGACTCGGGCTTTTTG | 12 |
| Raptor | Antisense | AATTCAAAAAGCCCGAGTCT GTGAATGTAATCTCGAGATT ACATTCACAGACTCGGGC | 13 |
| FKBP12 | Sense | CCGGGCCAAACTGATAATCT CCTCACTCGAGTGAGGAGAT TATCAGTTTGGCTTTTTG | 14 |
| FKBP12 | Antisense | AATTCAAAAAGCCAAACTGA TAATCTCCTCACTCGAGTGA GGAGATTATCAGTTTGGC | 15 |
| S6K1 | Sense | CCGGGCATGGAACATTGTGA GAAATCTCGAGATTTCTCAC AATGTTCCATGCTTTTTG | 16 |
| S6K1 | Antisense | AATTCAAAAAGCATGGAACA TTGTGAGAAATCTCGAGATT TCTCACAATGTTCCATGC | 17 |
| eIF4E | Sense | CCGGCCGAAGATAGTGATTG GTTATCTCGAGATAACCAAT CACTATCTTCGGTTTTTG | 18 |
| eIF4E | Antisense | AATTCAAAAACCGAAGATAG TGATTGGTTATCTCGAGATA ACCAATCACTATCTTCGG | 19 |

Recombinant retrovirus was made by co-transfection with pMKO.1 GFP and pCL-Eco (Imgenex, San Diego, Calif.) in 293T cells using TransIT-293 (Mirus, Madison, Wis.). Forty-eight hours after transfection, culture supernatants were collected. To transduce P14 cells with the recombinant retrovirus, P14 transgenic mice were infected with 1×10$^6$ PFU of LCMV intravenously. After 24 hours, P14 transgenic spleen cells were isolated and then spin-transduced at 37° C. for 90 minutes with freshly collected retrovirus containing 8 μg/ml of polybrene (Sigma, St. Louis, Mo.). Retroviral transduced P14 spleen cells (5×10$^5$) were adoptively transferred into naïve mice, followed by LCMV infection (2×10$^5$ PFU, IP). The GFP$^+$ P14 CD8$^+$ T cells were purified by FACS on Day 7 or 8 post-infection, and protein expression levels were analyzed by western blotting. Expression of mTOR, raptor, FKBP12, S6K1 and eIF4E was significantly reduced in cells transduced with retrovirus containing the respective shRNAs.

Results

The role of the mTOR pathway in regulating CD8$^+$ T cell responses is not well understood. To address this issue, B6 mice were treated with rapamycin during the course of an acute LCMV infection and the virus-specific CD8$^+$ T cell response was monitored (FIG. 20A). It was observed that rapamycin enhanced the LCMV-specific CD8$^+$ T cell response. Increased numbers of antigen-specific CD8$^+$ T cells were seen in both lymphoid and non-lymphoid tissues, including in PBMCs (FIG. 20A), spleen, lymph nodes and liver. The striking thing about this result was the decreased contraction of the T cell response in the rapamycin treated group. Similar frequencies of virus-specific effector CD8$^+$ T cells were observed in both groups of mice at the peak of the T cell response on Day 8 post-infection, but there was minimal contraction of the T cells in the rapamycin-treated group (FIG. 20A). To determine whether the decreased T cell contraction seen between about Days 8-30 post-infection in the rapamycin-treated group was due to increased cell proliferation and/or reduced cell death, mice were infected with LCMV in the presence or absence of rapamycin and then given BrdU during the T cell contraction phase from approximately Days 10-22. It was found that there was minimal incorporation of BrdU by antigen-specific CD8$^+$ T cells in either group of mice, indicating that the decreased contraction of T cells in the presence of rapamycin was not due to increased cell proliferation. Thus, it appears that the major effect of rapamycin is to enhance the survival of antigen-specific CD8$^+$ T cells.

Next, the phenotype of the memory CD8$^+$ T cells present in the two groups of mice at Day 36 post-infection was examined (FIG. 20B). To investigate this, phenotypic analysis of virus-specific memory CD8$^+$ T cells was performed using four markers that are useful in defining memory CD8$^+$ T cells: CD127 (IL-7 receptor α and essential for memory T cell maintenance; Kaech et al., Nat Immunol 4:1191-1198, 2003; Huster et al., Proc Natl Acad Sci USA 101:5610-5615, 2004; Schluns et al., Nat Immunol 1:426-432, 2000; Tan et al., J Exp Med 195:1523-32, 2002); CD62L (lymph node homing receptor and associated with high proliferative capacity; Wherry et al., Nat Immunol 4, 225-234, 2003); KLRG-1 (inversely-correlated with long lived memory cells; Sarkar et al., J Exp Med 205(3):625-40, 2008; Joshi et al., Immunity 27: 281-295, 2007); and Bcl-2 (anti-apoptotic and expressed at high levels in memory T cells; Schluns et al., Nat Immunol 1:426-432, 2000). Memory CD8$^+$ T cells generated in the presence of rapamycin expressed higher levels of CD127, CD62L, and Bcl-2, and had a higher frequency of KLRG-1$^{Low}$ cells compared to control mice (FIG. 20B). These data strongly suggest that inhibition of the mTOR pathway using rapamycin not only increases the magnitude of the virus-specific CD8$^+$ T cell response (FIG. 20A), but also improves the functional qualities of the memory CD8$^+$ T cells since memory cells with the CD127$^{High}$ CD62L$^{High}$Bcl-2$^{High}$ and KLRG-1$^{Low}$ phenotype are associated with long-lived protective immunity (Wherry et al., Nat Immunol 4, 225-234, 2003; Sarkar et al., J Exp Med 205(3):625-40, 2008; Joshi et al., Immunity 27: 281-295, 2007). To directly test this, the ability of these memory CD8$^+$ T cells to undergo homeostatic proliferation, a property essential for long-term memory maintenance, and to make recall responses upon re-exposure to antigen, was examined. As shown in FIG. 20C and FIG. 20D, virus-specific memory CD8$^+$ T cells generated in mice treated with rapamycin were superior to memory cells generated in untreated mice in both of these hallmark memory properties.

In the experiment shown in FIG. 20, mice were continuously treated with rapamycin during the entire course of the T cell response (Day −1 to 35 post-infection). It was next examined how rapamycin would affect the CD8$^+$ T cell response if it was only given during the T cell expansion phase (Days −1 to 8 post-infection). These results (FIGS. 21A and 21B) were strikingly similar to what was observed earlier (FIG. 20A); even if the rapamycin treatment was discontinued during the contraction phase (about Days 8-30) there was only minimal death of the effector CD8$^+$ T cells generated in the presence of the drug. Previous studies have shown that the Day 8 effector CD8$^+$ T cell population consists of two subsets, the terminal effector T cells (CD127$^{Low}$, KLRG-1$^{High}$) that mostly die over the ensuing 2-4 weeks, and the memory precursor cells (CD127$^{High}$, KLRG-1$^{Low}$) that mostly survive and further differentiate to give rise to the pool of long-lived memory cells (Kaech et al., *Nat Immunol* 4:1191-1198, 2003; Sarkar et al., *J Exp Med* 205(3):625-40, 2008; Joshi et al., *Immunity* 27: 281-295, 2007). These results suggested that rapamycin enhances the formation of these memory precursor cells. This was indeed the case and Day 8 virus-specific effector CD8+ T cells generated in rapamycin-treated mice contained a higher proportion of CD127$^{High}$ KLRG-1$^{Low}$ cells and these cells also expressed higher levels of Bcl-2 (FIG. 21C). However, it was observed that the phenotype of memory CD8+ T cells at Day 36 post-infection was similar in the drug-treated and control mice (FIG. 21D). This was different from the results obtained upon continuous rapamycin treatment (compare FIG. 20B versus FIG. 21D). Taken together, these results clearly show that rapamycin enhances the formation of memory precursors during the naïve to effector T cell differentiation phase, but that rapamycin may also regulate the effector to memory transition phase.

To test this hypothesis, mice were treated with rapamycin only during the T cell contraction phase (approximately Days 8-35) following acute LCMV infection (FIG. 22). It was found that the number of memory cells generated were not affected by the drug (FIG. 22A), but the phenotype of these memory CD8+ T cells was strikingly different (FIG. 22B). Thus, rapamycin treatment during the effector to memory transition phase enhanced the memory differentiation program resulting in a significantly higher number of virus-specific CD8+ T cells with the phenotype characteristic of highly functional memory cells (p value; <0.0001-0.0022) (FIG. 22B).

It was important to determine if this represented cell proliferation and outgrowth of a subset of effector CD8+ T cells already expressing these memory markers or if rapamycin truly increased the expression of these markers in the surviving effector T cells during this effector to memory differentiation phase. To address this issue, highly purified (>99.7%) and CFSE-labeled population of Day 8 CD62L$^{Low}$ antigen-specific effector CD8+ T cells were transferred into naïve mice and both cell division and memory differentiation of these transferred effector cells was monitored in the presence or absence of rapamycin (FIG. 22C). It was found that there was no cell division during this effector to memory transition phase (approximately Days 1-25 post-transfer), but that the memory T cells that differentiated in the presence of rapamycin re-expressed CD62L much faster (FIG. 22D and FIG. 22E). More importantly, these memory CD8+ T cells were functionally superior and exhibited better recall responses and protective immunity (viral control) following challenge with vaccinia virus expressing the LCMV GP33 epitope (FIGS. 22F-22H). Thus, inhibiting mTOR during the effector to memory transition phase improves the functional qualities of memory T cells.

The results described above demonstrate that rapamycin can enhance both the magnitude and quality of the CD8+ T cell response following a primary viral infection. It was next examined whether similar effects would be seen during a secondary response. As shown in FIG. 24, rapamycin also enhanced recall responses when drug treatment was only done during secondary LCMV infection. Thus, rapamycin regulates both primary and secondary T cell responses, which has important implications in designing strategies for improving memory T cell qualities during prime-boost vaccine regimens.

To determine if these findings from the mouse model of LCMV infection could be generalized to other systems, the effect of rapamycin treatment following immunization of mice with a non-replicating vaccine was examined. In these experiments, mice were vaccinated with VLPs (virus-like particles) derived from hepatitis B core antigen genetically fused to the LCMV GP33 epitope (Storni et al., *J Immunol* 172:1777-1785, 2004). Rapamycin again enhanced both the magnitude and the quality of the VLP-induced memory CD8+ T cells. It should be noted that the effects of rapamycin treatment were very long-lasting; memory T cell numbers remained 10-fold higher even 165 days after stopping the drug treatment.

The applicability of this approach was also tested in a non-human primate model. Rhesus macaques previously immunized with vaccinia virus were boosted with MVA in the presence or absence of rapamycin and antigen-specific CD8+ T cell responses were analyzed by intracellular IFN-γ staining Clear differences were found in frequencies of antigen-specific CD8+ T cells between rapamycin-treated and untreated monkeys. In the presence of rapamycin, maintenance of a higher number of memory CD8+ T cells was observed (FIG. 25A and FIG. 25B) and slower T cell contraction was evident compared to control animals (FIG. 25C). These results demonstrate that rapamycin enhances T cell immunity in both mice and non-human primates following vaccination with either live or inactivated vaccines.

These results clearly establish that mTOR is a major regulator of memory CD8+ T cell differentiation. However, one unanswered question is whether mTOR is acting intrinsically in antigen-specific CD8+ T cells to regulate memory differentiation or if the observed effects of rapamycin on memory formation are mediated by some other cells of the immune system. It is important to resolve this issue since mTOR is ubiquitously expressed by many cells and several recent studies have shown that rapamycin can modulate the functional properties of several other cells of the immune system (Cao et al., *Nat Immunol* 9(10):1157-1164, 2008; Sauer et al., *Proc Natl Acad Sci USA* 105:7797-7802, 2008; Haxhinasto et al., *J Exp Med* 205:565-574, 2008; Ohtani et al., *Blood* 112:635-643, 2008; Weichhart et al., *Immunity* 29(4):565-577, 2008).

To address this question, a retrovirus-based RNA interference (RNAi) system was used to specifically knock-down various genes of the mTOR pathway (mTOR, raptor, S6K1, eIF4E, and FKBP12) in antigen-specific CD8+ T cells. Retroviruses marked by GFP and expressing RNAi for a particular gene or a control retrovirus were used to infect LCMV-specific transgenic CD8+ T cells (P14 cells) and these transduced cells were then adoptively transferred into naïve mice, followed by LCMV infection. This system allowed for comparison of the phenotypic changes that occur during memory T cell differentiation in GFP-positive retrovirus-transduced versus GFP-negative non-transduced antigen-specific CD8+ T cells in the same environment (i.e., the same mouse). Thus, any differences in memory differentiation that are seen between these two cell populations can be ascribed to the intrinsic effects of that particular gene in antigen-specific T cells.

Figures 23A, 23B, 23C:
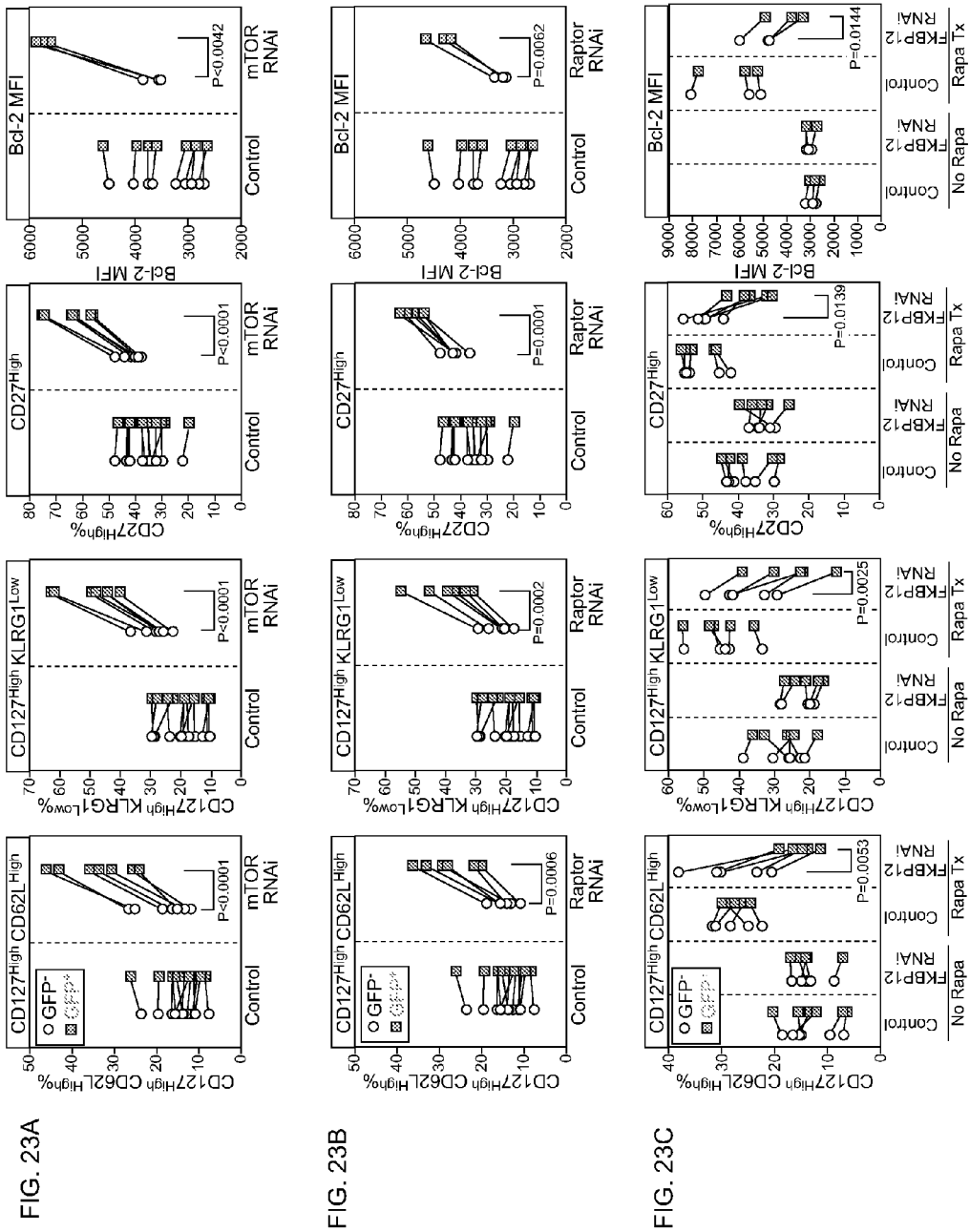
FIGS. 23A-23C are graphs showing knockdown of specific genes using a retrovirus based RNAi system. Retrovirus-transduced LCMV-specific P14 transgenic CD8+ T cells (marked by GFP expression) were adoptively transferred into naïve mice, followed by LCMV infection. Phenotypic analysis of retrovirus transduced cells (GFP+) and non-transduced (GFP−) P14 cells in PBMCs was performed on Days 14-16 post infection.
Figure 24A:
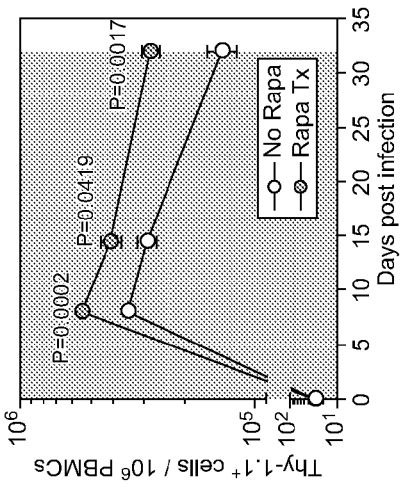
FIG. 24A is a schematic diagram showing LCMV-specific P14 transgenic memory CD8+ T cells (Thy-1.1) were adoptively transferred into Thy-1.2 naïve mice and these mice were infected with LCMV in the presence or absence of rapamycin (Day −1 to Day 32 post-infection).
Figure 24B:
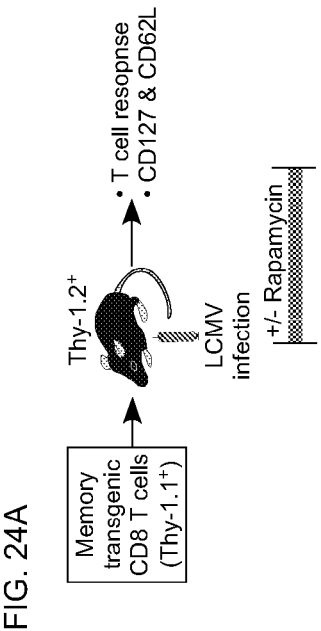
FIG. 24B is a graph showing kinetics of P14 recall responses upon infection. Flow data are gated on lymphocytes in PBMCs.
Figure 24D:
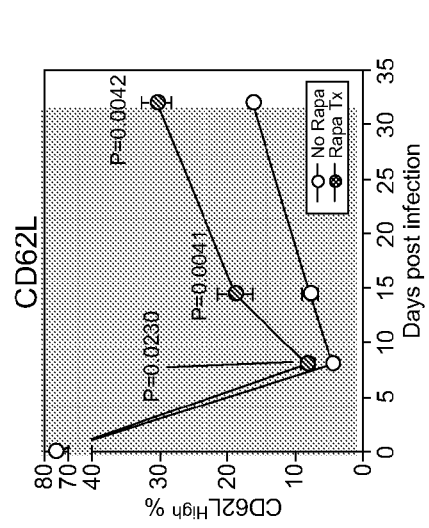
FIGS. 24C and 24D are a pair of graphs showing CD127 expression and CD62L expression, respectively, on P14 cells during recall responses. Error bars and shaded area indicate SEM and rapamycin treatment, respectively.
Figure 24C:
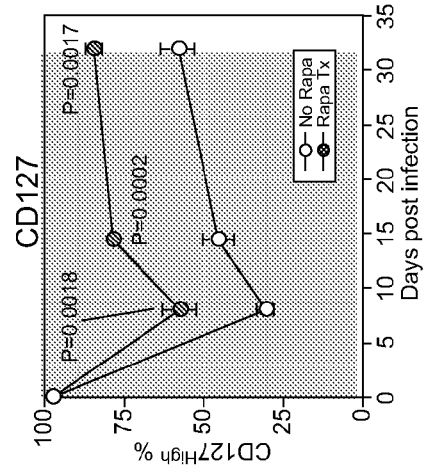

First, mTOR itself was knocked down in antigen-specific CD8+ T cells. It was found that mTOR RNAi retrovirus-transduced GFP+ P14 cells showed significantly higher expression of the canonical memory T cell markers (CD127, CD62L, Bcl-2, CD27) and lower expression of KLRG-1 compared to non-transduced or control vector-transduced P14 cells (FIG. 23A). These data show that mTOR acts intrinsically in antigen-specific CD8+ T cells to regulate memory differentiation. However, since mTOR forms two distinct complexes, the rapamycin-sensitive mTOR complex 1 (mTORC1) and the rapamycin-insensitive mTORC2 (see FIG. 15 and Wullschleger et al., *Cell* 124:471-484, 2006), mTOR knockdown does not completely mimic rapamycin treatment. To distinguish between these two pathways, the raptor gene, which is an essential component of the mTORC1 complex (Hara et al., *Cell* 110:177-189, 2002; Kim et al., *Cell* 110:163-175, 2002) was knocked down. As shown in FIG. 23B, inhibition of raptor in antigen-specific T cells gave results identical to what was observed upon knockdown of mTOR identifying the mTORC1 complex as the regulator of memory differentiation.

To gain more insight into mechanisms by which mTOR regulates memory formation, the roles of S6K1 and eIF4E were examined. It was found that knockdown of these mTORC1 downstream effectors significantly enhanced memory CD8+ T cell differentiation. Thus, these results show that mTOR is exerting its effect through these two downstream molecules.

To further explore the role of mTOR in T cell intrinsic versus external effects on memory differentiation, rapamycin-insensitive antigen-specific CD8+ T cells were generated by knockdown of the FKBP12 protein. This intracellular protein binds rapamycin and it is this FKBP12—rapamycin complex that inhibits the mTORC1 pathway. Thus, by knocking down FKBP12 in P14 CD8 cells, these cells were made insensitive to any intrinsic effects of rapamycin, but the drug could still act effectively on all the other cells in the mouse. This system allows one to examine if inhibition of mTOR in other cells can effect memory CD8+ T cell differentiation. As shown in FIG. 23C, inhibiting mTOR in other cells when the antigen-specific cells themselves were rapamycin-insensitive did not affect memory differentiation. The effect of rapamycin on memory differentiation almost disappeared upon knockdown of FKBP12 from the P14 cells and these cells did not show increased expression of the characteristic memory markers (e.g., CD127, CD62L, Bcl2) (see last column of the figures in FIG. 23C). Thus, taken together the results shown in FIGS. 23A-23C establish that mTOR not only acts intrinsically in antigen-specific CD8+ T cells, but that inhibiting mTOR in other cells has minimal to no effect on memory T cell differentiation.

During the past few years considerable progress has been made in understanding the lineage relationships between naïve, effector and memory T cells and in defining the phenotypic and functional changes that underlie memory CD8+ T cell differentiation (Williams et al., *Annu Rev Immunol* 25:171-192, 2007); Kaech et al., *Immunity* 27, 393-405, 2007). However, much less is known about the intracellular molecules and pathways that regulate the generation of memory T cells. In this example, a molecular pathway has been identified that regulates memory T cell differentiation. In addition, these findings provide a strategy for modulating the formation of memory cells. In particular, the ability to increase the functional qualities of memory T cells provides a new approach for enhancing the efficacy of vaccines against infectious diseases and cancer.

Example 6

Rapamycin Treatment with Hepatitis B Virus (HBV) Vaccination

This example describes the use of rapamycin in conjunction with the HBV vaccine to enhance immunological memory specific for HBV, thereby minimizing the need for booster immunizations. Currently, it is recommended that the HBV vaccine be administered in three doses. For infants, the first dose is typically administered at birth, followed by booster doses at 1-2 months and at 6-18 months. For adults, booster doses of the HBV vaccine are recommended 1-2 months and 4-6 months following primary immunization.

An adult subject with no prior exposure to HBV is administered a primary dose of HBV vaccine RECOMBIVAX HB™. Beginning on the day of immunization, the subject is orally administered rapamycin (in either tablet or liquid form) daily for 7 days. HBV immune responses can be evaluated in the subject following primary immunization and administration of rapamycin to determine whether a booster dose of HBV vaccine is required to establish sufficient immunological memory to prevent HBV infection.

Example 7

Rapamycin Treatment of a Subject with Chronic Hepatitis C Virus Infection

This example describes the use of rapamycin in the treatment of a subject diagnosed with chronic hepatitis C virus (HCV) infection. Patients with chronic HCV infection are at risk of developing liver inflammation, fibrosis, cirrhosis or liver cancer. Thus, it is desirable to treat HCV patients to reduce or eliminate HCV titers, replication and spread.

The subject diagnosed with chronic HCV is treated with a low dose of rapamycin (approximately 0.075 mg/kg) daily for 30 days. Rapamycin is administered orally (in either tablet or liquid form). HCV-specific immune responses, or the titer of HCV in the subject, can be evaluated after 30 days to determine if additional doses of rapamycin are required. The subject is optionally treated with anti-viral medication, such as interferon alpha or ribavirin.

Example 8

Rapamycin Treatment of a Subject Infected with Influenza Virus

This example describes the use of rapamycin in the treatment of a subject with an acute influenza virus infection. To enhance the immune responses against influenza virus, a subject with an acute infection is administered rapamycin within 15 days of exposure to the virus. The subject is administered rapamycin daily at a dose of approximately 0.6 mg/kg. Rapamycin is administered orally (in either tablet or liquid form). Rapamycin is administered daily for approximately 14 days, or until the symptoms of infection have cleared. The subject is optionally treated with anti-flu virus medication, such as oseltamivir, zanamavir, amantadine or rimantadine.

This disclosure provides a method of enhancing antigen-specific T cell immune responses in a subject. It will be apparent that the precise details of the methods described may be varied or modified without departing from the spirit of the described disclosure. We claim all such modifications and variations that fall within the scope and spirit of the claims below.

The invention claimed is:

1. A method of enhancing an antigen-specific T cell response in a subject, comprising: (1) administering to the subject a therapeutically effective amount of an antigen; and (2) administering to the subject a therapeutically effective amount of a mammalian target of rapamycin (mTOR) inhibitor during the T cell contraction phase.

2. The method of claim 1, wherein the T cells are CD8+ T cells.

3. The method of claim 2, wherein the CD8+ T cells are CD8+ memory T cells.

4. The method of claim 1, wherein the T cells are CD4+ T cells.

5. The method of claim 4, wherein the CD4+ T cells are CD4+ memory T cells.

6. The method of claim 1, wherein the antigen is from a pathogen.

7. The method of claim 6, wherein the pathogen is a virus, bacterium, fungus or parasite.

8. The method of claim 1, wherein the antigen comprises a tumor antigen.

9. The method of claim 8, wherein the tumor is a hematologic cancer or a solid tumor.

10. The method of claim 9, wherein the hematologic cancer is a leukemia or a lymphoma.

11. The method of claim 9, wherein the solid tumor is a carcinoma, melanoma, sarcoma or central nervous system tumor.

12. The method of claim 1, wherein the mTOR inhibitor is rapamycin or a rapamycin analog.

13. A method of determining the increase in the proportion of antigen-specific $CD127^{High}KLRG-1^{Low}$ CD8+ T cells in the subject, comprising: (1) administering to the subject a therapeutically effective amount of an antigen; and (2) administering to the subject a therapeutically effective amount of a mammalian target of rapamycin (mTOR) inhibitor during the T cell contraction phase; and (3) measuring the proportion of antigen-specific $CD127^{High}KLRG-1^{Low}$ CD8+ T cells in the subject relative to the proportion of $CD127^{High}KLRG-1^{Low}$ CD8+ T cells in the absence of treatment.

* * * * *

SEQUENCE LISTING

```
<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide
```

<400> SEQUENCE: 1
gcccgagtct gtgaatgtaa t                                       21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
gccaaactga taatctcctc a                                       21

<210> SEQ ID NO 3
<211> LENGTH: 8680
<212> TYPE: DNA
<213> ORGANISM: Homo sapiens
<220> FEATURE:
<221> NAME/KEY: CDS
<222> LOCATION: (80)..(7729)

<400> SEQUENCE: 3

```
acggggcctg aagcggcggt accggtgctg gcggcggcag ctgaggcctt ggccgaagcc    60
gcgcgaacct cagggcaag atg ctt gga acc gga cct gcc gcc gcc acc acc   112
                    Met Leu Gly Thr Gly Pro Ala Ala Ala Thr Thr
                     1               5                  10 gct gcc acc aca tct agc aat gtg agc gtc ctg cag cag ttt gcc agt    160
Ala Ala Thr Thr Ser Ser Asn Val Ser Val Leu Gln Gln Phe Ala Ser
             15                  20                  25 ggc cta aag agc cgg aat gag gaa acc agg gcc aaa gcc gcc aag gag    208
Gly Leu Lys Ser Arg Asn Glu Glu Thr Arg Ala Lys Ala Ala Lys Glu
         30                  35                  40 ctc cag cac tat gtc acc atg gaa ctc cga gag atg agt caa gag gag    256
Leu Gln His Tyr Val Thr Met Glu Leu Arg Glu Met Ser Gln Glu Glu
     45                  50                  55 tct act cgc ttc tat gac caa ctg aac cat cac att ttt gaa ttg gtt    304
Ser Thr Arg Phe Tyr Asp Gln Leu Asn His His Ile Phe Glu Leu Val
 60                  65                  70                  75 tcc agc tca gat gcc aat gag agg aaa ggt ggc atc ttg gcc ata gct    352
Ser Ser Ser Asp Ala Asn Glu Arg Lys Gly Gly Ile Leu Ala Ile Ala
                 80                  85                  90 agc ctc ata gga gtg gaa ggt ggg aat gcc acc cga att ggc aga ttt    400
Ser Leu Ile Gly Val Glu Gly Gly Asn Ala Thr Arg Ile Gly Arg Phe
             95                 100                 105 gcc aac tat ctt cgg aac ctc ctc ccc tcc aat gac cca gtt gtc atg    448
Ala Asn Tyr Leu Arg Asn Leu Leu Pro Ser Asn Asp Pro Val Val Met
        110                 115                 120 gaa atg gca tcc aag gcc att ggc cgt ctt gcc atg gca ggg gac act    496
Glu Met Ala Ser Lys Ala Ile Gly Arg Leu Ala Met Ala Gly Asp Thr
    125                 130                 135 ttt acc gct gag tac gtg gaa ttt gag gtg aag cga gcc ctg gaa tgg    544
Phe Thr Ala Glu Tyr Val Glu Phe Glu Val Lys Arg Ala Leu Glu Trp
140                 145                 150                 155 ctg ggt gct gac cgc aat gag ggc cgg aga cat gca gct gtc ctg gtt    592
Leu Gly Ala Asp Arg Asn Glu Gly Arg Arg His Ala Ala Val Leu Val
                160                 165                 170 ctc cgt gag ctg gcc atc agc gtc cct acc ttc ttc ttc cag caa gtg    640
Leu Arg Glu Leu Ala Ile Ser Val Pro Thr Phe Phe Phe Gln Gln Val
            175                 180                 185 caa ccc ttc ttt gac aac att ttt gtg gcc gtg tgg gac ccc aaa cag    688
Gln Pro Phe Phe Asp Asn Ile Phe Val Ala Val Trp Asp Pro Lys Gln
```

```
                190                 195                 200
gcc atc cgt gag gga gct gta gcc gcc ctt cgt gcc tgt ctg att ctc       736
Ala Ile Arg Glu Gly Ala Val Ala Ala Leu Arg Ala Cys Leu Ile Leu
    205                 210                 215 aca acc cag cgt gag ccg aag gag atg cag aag cct cag tgg tac agg       784
Thr Thr Gln Arg Glu Pro Lys Glu Met Gln Lys Pro Gln Trp Tyr Arg
220                 225                 230                 235 cac aca ttt gaa gaa gca gag aag gga ttt gat gag acc ttg gcc aaa       832
His Thr Phe Glu Glu Ala Glu Lys Gly Phe Asp Glu Thr Leu Ala Lys
                240                 245                 250 gag aag ggc atg aat cgg gat gat cgg atc cat gga gcc ttg ttg atc       880
Glu Lys Gly Met Asn Arg Asp Asp Arg Ile His Gly Ala Leu Leu Ile
            255                 260                 265 ctt aac gag ctg gtc cga atc agc agc atg gag gga gag cgt ctg aga       928
Leu Asn Glu Leu Val Arg Ile Ser Ser Met Glu Gly Glu Arg Leu Arg
        270                 275                 280 gaa gaa atg gaa gaa atc aca cag cag cag ctg gta cac gac aag tac       976
Glu Glu Met Glu Glu Ile Thr Gln Gln Gln Leu Val His Asp Lys Tyr
    285                 290                 295 tgc aaa gat ctc atg ggc ttc gga aca aaa cct cgt cac att acc ccc      1024
Cys Lys Asp Leu Met Gly Phe Gly Thr Lys Pro Arg His Ile Thr Pro
300                 305                 310                 315 ttc acc agt ttc cag gct gta cag ccc cag cag tca aat gcc ttg gtg      1072
Phe Thr Ser Phe Gln Ala Val Gln Pro Gln Gln Ser Asn Ala Leu Val
                320                 325                 330 ggg ctg ctg ggg tac agc tct cac caa ggc ctc atg gga ttt ggg acc      1120
Gly Leu Leu Gly Tyr Ser Ser His Gln Gly Leu Met Gly Phe Gly Thr
            335                 340                 345 tcc ccc agt cca gct aag tcc acc ctg gtg gag agc cgg tgt tgc aga      1168
Ser Pro Ser Pro Ala Lys Ser Thr Leu Val Glu Ser Arg Cys Cys Arg
        350                 355                 360 gac ttg atg gag gag aaa ttt gat cag gtg tgc cag tgg gtg ctg aaa      1216
Asp Leu Met Glu Glu Lys Phe Asp Gln Val Cys Gln Trp Val Leu Lys
    365                 370                 375 tgc agg aat agc aag aac tcg ctg atc caa atg aca atc ctt aat ttg      1264
Cys Arg Asn Ser Lys Asn Ser Leu Ile Gln Met Thr Ile Leu Asn Leu
380                 385                 390                 395 ttg ccc cgc ttg gct gca ttc cga cct tct gcc ttc aca gat acc cag      1312
Leu Pro Arg Leu Ala Ala Phe Arg Pro Ser Ala Phe Thr Asp Thr Gln
                400                 405                 410 tat ctc caa gat acc atg aac cat gtc cta agc tgt gtc aag aag gag      1360
Tyr Leu Gln Asp Thr Met Asn His Val Leu Ser Cys Val Lys Lys Glu
            415                 420                 425 aag gaa cgt aca gcg gcc ttc caa gcc ctg ggg cta ctt tct gtg gct      1408
Lys Glu Arg Thr Ala Ala Phe Gln Ala Leu Gly Leu Leu Ser Val Ala
        430                 435                 440 gtg agg tct gag ttt aag gtc tat ttg cct cgc gtg ctg gac atc atc      1456
Val Arg Ser Glu Phe Lys Val Tyr Leu Pro Arg Val Leu Asp Ile Ile
    445                 450                 455 cga gcg gcc ctg ccc cca aag gac ttc gcc cat aag agg cag aag gca      1504
Arg Ala Ala Leu Pro Pro Lys Asp Phe Ala His Lys Arg Gln Lys Ala
460                 465                 470                 475 atg cag gtg gat gcc aca gtc ttc act tgc atc agc atg ctg gct cga      1552
Met Gln Val Asp Ala Thr Val Phe Thr Cys Ile Ser Met Leu Ala Arg
                480                 485                 490 gca atg ggg cca ggc atc cag cag gat atc aag gag ctg ctg gag ccc      1600
Ala Met Gly Pro Gly Ile Gln Gln Asp Ile Lys Glu Leu Leu Glu Pro
            495                 500                 505 atg ctg gca gtg gga cta agc cct gcc ctc act gca gtg ctc tac gac      1648
```

```
Met Leu Ala Val Gly Leu Ser Pro Ala Leu Thr Ala Val Leu Tyr Asp
        510                 515                 520 ctg agc cgt cag att cca cag cta aag aag gac att caa gat ggg cta     1696
Leu Ser Arg Gln Ile Pro Gln Leu Lys Lys Asp Ile Gln Asp Gly Leu
525                 530                 535 ctg aaa atg ctg tcc ctg gtc ctt atg cac aaa ccc ctt cgc cac cca     1744
Leu Lys Met Leu Ser Leu Val Leu Met His Lys Pro Leu Arg His Pro
540                 545                 550                 555 ggc atg ccc aag ggc ctg gcc cat cag ctg gcc tct cct ggc ctc acg     1792
Gly Met Pro Lys Gly Leu Ala His Gln Leu Ala Ser Pro Gly Leu Thr
                560                 565                 570 acc ctc cct gag gcc agc gat gtg ggc agc atc act ctt gcc ctc cga     1840
Thr Leu Pro Glu Ala Ser Asp Val Gly Ser Ile Thr Leu Ala Leu Arg
            575                 580                 585 acg ctt ggc agc ttt gaa ttt gaa ggc cac tct ctg acc caa ttt gtt     1888
Thr Leu Gly Ser Phe Glu Phe Glu Gly His Ser Leu Thr Gln Phe Val
        590                 595                 600 cgc cac tgt gcg gat cat ttc ctg aac agt gag cac aag gag atc cgc     1936
Arg His Cys Ala Asp His Phe Leu Asn Ser Glu His Lys Glu Ile Arg
    605                 610                 615 atg gag gct gcc cgc acc tgc tcc cgc ctg ctc aca ccc tcc atc cac     1984
Met Glu Ala Ala Arg Thr Cys Ser Arg Leu Leu Thr Pro Ser Ile His
620                 625                 630                 635 ctc atc agt ggc cat gct cat gtg gtt agc cag acc gca gtg caa gtg     2032
Leu Ile Ser Gly His Ala His Val Val Ser Gln Thr Ala Val Gln Val
                640                 645                 650 gtg gca gat gtg ctt agc aaa ctg ctc gta gtt ggg ata aca gat cct     2080
Val Ala Asp Val Leu Ser Lys Leu Leu Val Val Gly Ile Thr Asp Pro
            655                 660                 665 gac cct gac att cgc tac tgt gtc ttg gcg tcc ctg gac gag cgc ttt     2128
Asp Pro Asp Ile Arg Tyr Cys Val Leu Ala Ser Leu Asp Glu Arg Phe
        670                 675                 680 gat gca cac ctg gcc cag gcg gag aac ttg cag gcc ttg ttt gtg gct     2176
Asp Ala His Leu Ala Gln Ala Glu Asn Leu Gln Ala Leu Phe Val Ala
    685                 690                 695 ctg aat gac cag gtg ttt gag atc cgg gag ctg gcc atc tgc act gtg     2224
Leu Asn Asp Gln Val Phe Glu Ile Arg Glu Leu Ala Ile Cys Thr Val
700                 705                 710                 715 ggc cga ctc agt agc atg aac cct gcc ttt gtc atg cct ttc ctg cgc     2272
Gly Arg Leu Ser Ser Met Asn Pro Ala Phe Val Met Pro Phe Leu Arg
                720                 725                 730 aag atg ctc atc cag att ttg aca gag ttg gag cac agt ggg att gga     2320
Lys Met Leu Ile Gln Ile Leu Thr Glu Leu Glu His Ser Gly Ile Gly
            735                 740                 745 aga atc aaa gag cag agt gcc cgc atg ctg ggg cac ctg gtc tcc aat     2368
Arg Ile Lys Glu Gln Ser Ala Arg Met Leu Gly His Leu Val Ser Asn
        750                 755                 760 gcc ccc cga ctc atc cgc ccc tac atg gag cct att ctg aag gca tta     2416
Ala Pro Arg Leu Ile Arg Pro Tyr Met Glu Pro Ile Leu Lys Ala Leu
    765                 770                 775 att ttg aaa ctg aaa gat cca gac cct gat cca aac cca ggt gtg atc     2464
Ile Leu Lys Leu Lys Asp Pro Asp Pro Asp Pro Asn Pro Gly Val Ile
780                 785                 790                 795 aat aat gtc ctg gca aca ata gga gaa ttg gca cag gtt agt ggc ctg     2512
Asn Asn Val Leu Ala Thr Ile Gly Glu Leu Ala Gln Val Ser Gly Leu
                800                 805                 810 gaa atg agg aaa tgg gtt gat gaa ctt ttt att atc atc atg gac atg     2560
Glu Met Arg Lys Trp Val Asp Glu Leu Phe Ile Ile Ile Met Asp Met
            815                 820                 825
```

-continued

| | |
|---|---|
| ctc cag gat tcc tct ttg ttg gcc aaa agg cag gtg gct ctg tgg acc<br>Leu Gln Asp Ser Ser Leu Leu Ala Lys Arg Gln Val Ala Leu Trp Thr<br>         830                   835                  840 | 2608 |
| ctg gga cag ttg gtg gcc agc act ggc tat gta gta gag ccc tac agg<br>Leu Gly Gln Leu Val Ala Ser Thr Gly Tyr Val Val Glu Pro Tyr Arg<br>845                   850                   855 | 2656 |
| aag tac cct act ttg ctt gag gtg cta ctg aat ttt ctg aag act gag<br>Lys Tyr Pro Thr Leu Leu Glu Val Leu Leu Asn Phe Leu Lys Thr Glu<br>860                   865                  870                  875 | 2704 |
| cag aac cag ggt aca cgc aga gag gcc atc cgt gtg tta ggg ctt tta<br>Gln Asn Gln Gly Thr Arg Arg Glu Ala Ile Arg Val Leu Gly Leu Leu<br>                 880                   885                  890 | 2752 |
| ggg gct ttg gat cct tac aag cac aaa gtg aac att ggc atg ata gac<br>Gly Ala Leu Asp Pro Tyr Lys His Lys Val Asn Ile Gly Met Ile Asp<br>         895                   900                  905 | 2800 |
| cag tcc cgg gat gcc tct gct gtc agc ctg tca gaa tcc aag tca agt<br>Gln Ser Arg Asp Ala Ser Ala Val Ser Leu Ser Glu Ser Lys Ser Ser<br>910                   915                  920 | 2848 |
| cag gat tcc tct gac tat agc act agt gaa atg ctg gtc aac atg gga<br>Gln Asp Ser Ser Asp Tyr Ser Thr Ser Glu Met Leu Val Asn Met Gly<br>925                   930                  935 | 2896 |
| aac ttg cct ctg gat gag ttc tac cca gct gtg tcc atg gtg gcc ctg<br>Asn Leu Pro Leu Asp Glu Phe Tyr Pro Ala Val Ser Met Val Ala Leu<br>940                   945                  950                  955 | 2944 |
| atg cgg atc ttc cga gac cag tca ctc tct cat cat cac acc atg gtt<br>Met Arg Ile Phe Arg Asp Gln Ser Leu Ser His His His Thr Met Val<br>                 960                   965                  970 | 2992 |
| gtc cag gcc atc acc ttc atc ttc aag tcc ctg gga ctc aaa tgt gtg<br>Val Gln Ala Ile Thr Phe Ile Phe Lys Ser Leu Gly Leu Lys Cys Val<br>         975                   980                  985 | 3040 |
| cag ttc ctg ccc cag gtc atg ccc acg ttc ctt aac gtc att cga gtc<br>Gln Phe Leu Pro Gln Val Met Pro Thr Phe Leu Asn Val Ile Arg Val<br>990                   995                  1000 | 3088 |
| tgt gat ggg gcc atc cgg gaa ttt ttg ttc cag cag ctg gga atg<br>Cys Asp Gly Ala Ile Arg Glu Phe Leu Phe Gln Gln Leu Gly Met<br>1005                 1010                 1015 | 3133 |
| ttg gtg tcc ttt gtg aag agc cac atc aga cct tat atg gat gaa<br>Leu Val Ser Phe Val Lys Ser His Ile Arg Pro Tyr Met Asp Glu<br>1020                 1025                 1030 | 3178 |
| ata gtc acc ctc atg aga gaa ttc tgg gtc atg aac acc tca att<br>Ile Val Thr Leu Met Arg Glu Phe Trp Val Met Asn Thr Ser Ile<br>1035                 1040                 1045 | 3223 |
| cag agc acg atc att ctt ctc att gag caa att gtg gta gct ctt<br>Gln Ser Thr Ile Ile Leu Leu Ile Glu Gln Ile Val Val Ala Leu<br>1050                 1055                 1060 | 3268 |
| ggg ggt gaa ttt aag ctc tac ctg ccc cag ctg atc cca cac atg<br>Gly Gly Glu Phe Lys Leu Tyr Leu Pro Gln Leu Ile Pro His Met<br>1065                 1070                 1075 | 3313 |
| ctg cgt gtc ttc atg cat gac aac agc cca ggc cgc att gtc tct<br>Leu Arg Val Phe Met His Asp Asn Ser Pro Gly Arg Ile Val Ser<br>1080                 1085                 1090 | 3358 |
| atc aag tta ctg gct gca atc cag ctg ttt ggc gcc aac ctg gat<br>Ile Lys Leu Leu Ala Ala Ile Gln Leu Phe Gly Ala Asn Leu Asp<br>1095                 1100                 1105 | 3403 |
| gac tac ctg cat tta ctg ctg cct cct att gtt aag ttg ttt gat<br>Asp Tyr Leu His Leu Leu Leu Pro Pro Ile Val Lys Leu Phe Asp<br>1110                 1115                 1120 | 3448 |
| gcc cct gaa gct cca ctg cca tct cga aag gca gcg cta gag act<br>Ala Pro Glu Ala Pro Leu Pro Ser Arg Lys Ala Ala Leu Glu Thr<br>1125                 1130                 1135 | 3493 |

```
gtg gac cgc ctg acg gag tcc ctg gat ttc act gac tat gcc tcc      3538
Val Asp Arg Leu Thr Glu Ser Leu Asp Phe Thr Asp Tyr Ala Ser
    1140                1145                1150 cgg atc att cac cct att gtt cga aca ctg gac cag agc cca gaa      3583
Arg Ile Ile His Pro Ile Val Arg Thr Leu Asp Gln Ser Pro Glu
1155                1160                1165 ctg cgc tcc aca gcc atg gac acg ctg tct tca ctt gtt ttt cag      3628
Leu Arg Ser Thr Ala Met Asp Thr Leu Ser Ser Leu Val Phe Gln
    1170                1175                1180 ctg ggg aag aag tac caa att ttc att cca atg gtg aat aaa gtt      3673
Leu Gly Lys Lys Tyr Gln Ile Phe Ile Pro Met Val Asn Lys Val
    1185                1190                1195 ctg gtg cga cac cga atc aat cat cag cgc tat gat gtg ctc atc      3718
Leu Val Arg His Arg Ile Asn His Gln Arg Tyr Asp Val Leu Ile
    1200                1205                1210 tgc aga att gtc aag gga tac aca ctt gct gat gaa gag gag gat      3763
Cys Arg Ile Val Lys Gly Tyr Thr Leu Ala Asp Glu Glu Glu Asp
    1215                1220                1225 cct ttg att tac cag cat cgg atg ctt agg agt ggc caa ggg gat      3808
Pro Leu Ile Tyr Gln His Arg Met Leu Arg Ser Gly Gln Gly Asp
    1230                1235                1240 gca ttg gct agt gga cca gtg gaa aca gga ccc atg aag aaa ctg      3853
Ala Leu Ala Ser Gly Pro Val Glu Thr Gly Pro Met Lys Lys Leu
    1245                1250                1255 cac gtc agc acc atc aac ctc caa aag gcc tgg ggc gct gcc agg      3898
His Val Ser Thr Ile Asn Leu Gln Lys Ala Trp Gly Ala Ala Arg
    1260                1265                1270 agg gtc tcc aaa gat gac tgg ctg gaa tgg ctg aga cgg ctg agc      3943
Arg Val Ser Lys Asp Asp Trp Leu Glu Trp Leu Arg Arg Leu Ser
    1275                1280                1285 ctg gag ctg ctg aag gac tca tca tcg ccc tcc ctg cgc tcc tgc      3988
Leu Glu Leu Leu Lys Asp Ser Ser Ser Pro Ser Leu Arg Ser Cys
    1290                1295                1300 tgg gcc ctg gca cag gcc tac aac ccg atg gcc agg gat ctc ttc      4033
Trp Ala Leu Ala Gln Ala Tyr Asn Pro Met Ala Arg Asp Leu Phe
    1305                1310                1315 aat gct gca ttt gtg tcc tgc tgg tct gaa ctg aat gaa gat caa      4078
Asn Ala Ala Phe Val Ser Cys Trp Ser Glu Leu Asn Glu Asp Gln
    1320                1325                1330 cag gat gag ctc atc aga agc atc gag ttg gcc ctc acc tca caa      4123
Gln Asp Glu Leu Ile Arg Ser Ile Glu Leu Ala Leu Thr Ser Gln
    1335                1340                1345 gac atc gct gaa gtc aca cag acc ctc tta aac ttg gct gaa ttc      4168
Asp Ile Ala Glu Val Thr Gln Thr Leu Leu Asn Leu Ala Glu Phe
    1350                1355                1360 atg gaa cac agt gac aag ggc ccc ctg cca ctg aga gat gac aat      4213
Met Glu His Ser Asp Lys Gly Pro Leu Pro Leu Arg Asp Asp Asn
    1365                1370                1375 ggc att gtt ctg ctg ggt gag aga gct gcc aag tgc cga gca tat      4258
Gly Ile Val Leu Leu Gly Glu Arg Ala Ala Lys Cys Arg Ala Tyr
    1380                1385                1390 gcc aaa gca cta cac tac aaa gaa ctg gag ttc cag aaa ggc ccc      4303
Ala Lys Ala Leu His Tyr Lys Glu Leu Glu Phe Gln Lys Gly Pro
    1395                1400                1405 acc cct gcc att cta gaa tct ctc atc agc att aat aat aag cta      4348
Thr Pro Ala Ile Leu Glu Ser Leu Ile Ser Ile Asn Asn Lys Leu
    1410                1415                1420 cag cag ccg gag gca gcg gcc gga gtg tta gaa tat gcc atg aaa      4393
Gln Gln Pro Glu Ala Ala Ala Gly Val Leu Glu Tyr Ala Met Lys
```

```
                  1425                     1430                     1435 cac  ttt  gga  gag  ctg  gag  atc  cag  gct  acc  tgg  tat  gag  aaa  ctg       4438
His  Phe  Gly  Glu  Leu  Glu  Ile  Gln  Ala  Thr  Trp  Tyr  Glu  Lys  Leu
     1440                     1445                     1450 cac  gag  tgg  gag  gat  gcc  ctt  gtg  gcc  tat  gac  aag  aaa  atg  gac       4483
His  Glu  Trp  Glu  Asp  Ala  Leu  Val  Ala  Tyr  Asp  Lys  Lys  Met  Asp
1455                     1460                     1465 acc  aac  aag  gac  gac  cca  gag  ctg  atg  ctg  ggc  cgc  atg  cgc  tgc       4528
Thr  Asn  Lys  Asp  Asp  Pro  Glu  Leu  Met  Leu  Gly  Arg  Met  Arg  Cys
     1470                     1475                     1480 ctc  gag  gcc  ttg  ggg  gaa  tgg  ggt  caa  ctc  cac  cag  cag  tgc  tgt       4573
Leu  Glu  Ala  Leu  Gly  Glu  Trp  Gly  Gln  Leu  His  Gln  Gln  Cys  Cys
          1485                     1490                     1495 gaa  aag  tgg  acc  ctg  gtt  aat  gat  gag  acc  caa  gcc  aag  atg  gcc       4618
Glu  Lys  Trp  Thr  Leu  Val  Asn  Asp  Glu  Thr  Gln  Ala  Lys  Met  Ala
1500                     1505                     1510 cgg  atg  gct  gct  gca  gct  gca  tgg  ggt  tta  ggt  cag  tgg  gac  agc       4663
Arg  Met  Ala  Ala  Ala  Ala  Ala  Trp  Gly  Leu  Gly  Gln  Trp  Asp  Ser
     1515                     1520                     1525 atg  gaa  gaa  tac  acc  tgt  atg  atc  cct  cgg  gac  acc  cat  gat  ggg       4708
Met  Glu  Glu  Tyr  Thr  Cys  Met  Ile  Pro  Arg  Asp  Thr  His  Asp  Gly
          1530                     1535                     1540 gca  ttt  tat  aga  gct  gtg  ctg  gca  ctg  cat  cag  gac  ctc  ttc  tcc       4753
Ala  Phe  Tyr  Arg  Ala  Val  Leu  Ala  Leu  His  Gln  Asp  Leu  Phe  Ser
1545                     1550                     1555 ttg  gca  caa  cag  tgc  att  gac  aag  gcc  agg  gac  ctg  ctg  gat  gct       4798
Leu  Ala  Gln  Gln  Cys  Ile  Asp  Lys  Ala  Arg  Asp  Leu  Leu  Asp  Ala
     1560                     1565                     1570 gaa  tta  act  gcg  atg  gca  gga  gag  agt  tac  agt  cgg  gca  tat  ggg       4843
Glu  Leu  Thr  Ala  Met  Ala  Gly  Glu  Ser  Tyr  Ser  Arg  Ala  Tyr  Gly
          1575                     1580                     1585 gcc  atg  gtt  tct  tgc  cac  atg  ctg  tcc  gag  ctg  gag  gag  gtt  atc       4888
Ala  Met  Val  Ser  Cys  His  Met  Leu  Ser  Glu  Leu  Glu  Glu  Val  Ile
1590                     1595                     1600 cag  tac  aaa  ctt  gtc  ccc  gag  cga  cga  gag  atc  atc  cgc  cag  atc       4933
Gln  Tyr  Lys  Leu  Val  Pro  Glu  Arg  Arg  Glu  Ile  Ile  Arg  Gln  Ile
     1605                     1610                     1615 tgg  tgg  gag  aga  ctg  cag  ggc  tgc  cag  cgt  atc  gta  gag  gac  tgg       4978
Trp  Trp  Glu  Arg  Leu  Gln  Gly  Cys  Gln  Arg  Ile  Val  Glu  Asp  Trp
          1620                     1625                     1630 cag  aaa  atc  ctt  atg  gtg  cgg  tcc  ctt  gtg  gtc  agc  cct  cat  gaa       5023
Gln  Lys  Ile  Leu  Met  Val  Arg  Ser  Leu  Val  Val  Ser  Pro  His  Glu
1635                     1640                     1645 gac  atg  aga  acc  tgg  ctc  aag  tat  gca  agc  ctg  tgc  ggc  aag  agt       5068
Asp  Met  Arg  Thr  Trp  Leu  Lys  Tyr  Ala  Ser  Leu  Cys  Gly  Lys  Ser
     1650                     1655                     1660 ggc  agg  ctg  gct  ctt  gct  cat  aaa  act  tta  gtg  ttg  ctc  ctg  gga       5113
Gly  Arg  Leu  Ala  Leu  Ala  His  Lys  Thr  Leu  Val  Leu  Leu  Leu  Gly
          1665                     1670                     1675 gtt  gat  ccg  tct  cgg  caa  ctt  gac  cat  cct  ctg  cca  aca  gtt  cac       5158
Val  Asp  Pro  Ser  Arg  Gln  Leu  Asp  His  Pro  Leu  Pro  Thr  Val  His
1680                     1685                     1690 cct  cag  gtg  acc  tat  gcc  tac  atg  aaa  aac  atg  tgg  aag  agt  gcc       5203
Pro  Gln  Val  Thr  Tyr  Ala  Tyr  Met  Lys  Asn  Met  Trp  Lys  Ser  Ala
     1695                     1700                     1705 cgc  aag  atc  gat  gcc  ttc  cag  cac  atg  cag  cat  ttt  gtc  cag  acc       5248
Arg  Lys  Ile  Asp  Ala  Phe  Gln  His  Met  Gln  His  Phe  Val  Gln  Thr
          1710                     1715                     1720 atg  cag  caa  cag  gcc  cag  cat  gcc  atc  gct  act  gag  gac  cag  cag       5293
```

```
                Met Gln Gln Gln Ala Gln His Ala Ile Ala Thr Glu Asp Gln Gln
                    1725                1730                1735 cat aag cag gaa ctg cac aag ctc atg gcc cga tgc ttc ctg aaa              5338
His Lys Gln Glu Leu His Lys Leu Met Ala Arg Cys Phe Leu Lys
    1740                1745                1750 ctt gga gag tgg cag ctg aat cta cag ggc atc aat gag agc aca              5383
Leu Gly Glu Trp Gln Leu Asn Leu Gln Gly Ile Asn Glu Ser Thr
    1755                1760                1765 atc ccc aaa gtg ctg cag tac tac agc gcc gcc aca gag cac gac              5428
Ile Pro Lys Val Leu Gln Tyr Tyr Ser Ala Ala Thr Glu His Asp
    1770                1775                1780 cgc agc tgg tac aag gcc tgg cat gcg tgg gca gtg atg aac ttc              5473
Arg Ser Trp Tyr Lys Ala Trp His Ala Trp Ala Val Met Asn Phe
    1785                1790                1795 gaa gct gtg cta cac tac aaa cat cag aac caa gcc cgc gat gag              5518
Glu Ala Val Leu His Tyr Lys His Gln Asn Gln Ala Arg Asp Glu
    1800                1805                1810 aag aag aaa ctg cgt cat gcc agc ggg gcc aac atc acc aac gcc              5563
Lys Lys Lys Leu Arg His Ala Ser Gly Ala Asn Ile Thr Asn Ala
    1815                1820                1825 acc act gcc gcc acc acg gcc gcc act gcc acc acc act gcc agc              5608
Thr Thr Ala Ala Thr Thr Ala Ala Thr Ala Thr Thr Thr Ala Ser
    1830                1835                1840 acc gag ggc agc aac agt gag agc gag gcc gag agc acc gag aac              5653
Thr Glu Gly Ser Asn Ser Glu Ser Glu Ala Glu Ser Thr Glu Asn
    1845                1850                1855 agc ccc acc cca tcg ccg ctg cag aag aag gtc act gag gat ctg              5698
Ser Pro Thr Pro Ser Pro Leu Gln Lys Lys Val Thr Glu Asp Leu
    1860                1865                1870 tcc aaa acc ctc ctg atg tac acg gtg cct gcc gtc cag ggc ttc              5743
Ser Lys Thr Leu Leu Met Tyr Thr Val Pro Ala Val Gln Gly Phe
    1875                1880                1885 ttc cgt tcc atc tcc ttg tca cga ggc aac aac ctc cag gat aca              5788
Phe Arg Ser Ile Ser Leu Ser Arg Gly Asn Asn Leu Gln Asp Thr
    1890                1895                1900 ctc aga gtt ctc acc tta tgg ttt gat tat ggt cac tgg cca gat              5833
Leu Arg Val Leu Thr Leu Trp Phe Asp Tyr Gly His Trp Pro Asp
    1905                1910                1915 gtc aat gag gcc tta gtg gag ggg gtg aaa gcc atc cag att gat              5878
Val Asn Glu Ala Leu Val Glu Gly Val Lys Ala Ile Gln Ile Asp
    1920                1925                1930 acc tgg cta cag gtt ata cct cag ctc att gca aga att gat acg              5923
Thr Trp Leu Gln Val Ile Pro Gln Leu Ile Ala Arg Ile Asp Thr
    1935                1940                1945 ccc aga ccc ttg gtg gga cgt ctc att cac cag ctt ctc aca gac              5968
Pro Arg Pro Leu Val Gly Arg Leu Ile His Gln Leu Leu Thr Asp
    1950                1955                1960 att ggt cgg tac cac ccc cag gcc ctc atc tac cca ctg aca gtg              6013
Ile Gly Arg Tyr His Pro Gln Ala Leu Ile Tyr Pro Leu Thr Val
    1965                1970                1975 gct tct aag tct acc acg aca gcc cgg cac aat gca gcc aac aag              6058
Ala Ser Lys Ser Thr Thr Thr Ala Arg His Asn Ala Ala Asn Lys
    1980                1985                1990 att ctg aag aac atg tgt gag cac agc aac acc ctg gtc cag cag              6103
Ile Leu Lys Asn Met Cys Glu His Ser Asn Thr Leu Val Gln Gln
    1995                2000                2005 gcc atg atg gtg agc gag gag ctg atc cga gtg gcc atc ctc tgg              6148
Ala Met Met Val Ser Glu Glu Leu Ile Arg Val Ala Ile Leu Trp
    2010                2015                2020
```

| | | | | | | | | | | |
|---|---|---|---|---|---|---|---|---|---|---|
| cat | gag | atg | tgg | cat | gaa | ggc | ctg | gaa | gag | gca | tct | cgt | ttg | tac | 6193 |
| His | Glu | Met | Trp | His | Glu | Gly | Leu | Glu | Glu | Ala | Ser | Arg | Leu | Tyr | |
| | | 2025 | | | | 2030 | | | | 2035 | | | | | |

| | | | | | | | | | | |
|---|---|---|---|---|---|---|---|---|---|---|
| ttt | ggg | gaa | agg | aac | gtg | aaa | ggc | atg | ttt | gag | gtg | ctg | gag | ccc | 6238 |
| Phe | Gly | Glu | Arg | Asn | Val | Lys | Gly | Met | Phe | Glu | Val | Leu | Glu | Pro | |
| | | 2040 | | | | 2045 | | | | 2050 | | | | | |

| | | | | | | | | | | |
|---|---|---|---|---|---|---|---|---|---|---|
| ttg | cat | gct | atg | atg | gaa | cgg | ggc | ccc | cag | act | ctg | aag | gaa | aca | 6283 |
| Leu | His | Ala | Met | Met | Glu | Arg | Gly | Pro | Gln | Thr | Leu | Lys | Glu | Thr | |
| | | 2055 | | | | 2060 | | | | 2065 | | | | | |

| | | | | | | | | | | |
|---|---|---|---|---|---|---|---|---|---|---|
| tcc | ttt | aat | cag | gcc | tat | ggt | cga | gat | tta | atg | gag | gcc | caa | gag | 6328 |
| Ser | Phe | Asn | Gln | Ala | Tyr | Gly | Arg | Asp | Leu | Met | Glu | Ala | Gln | Glu | |
| | | 2070 | | | | 2075 | | | | 2080 | | | | | |

| | | | | | | | | | | |
|---|---|---|---|---|---|---|---|---|---|---|
| tgg | tgc | agg | aag | tac | atg | aaa | tca | ggg | aat | gtc | aag | gac | ctc | acc | 6373 |
| Trp | Cys | Arg | Lys | Tyr | Met | Lys | Ser | Gly | Asn | Val | Lys | Asp | Leu | Thr | |
| | | 2085 | | | | 2090 | | | | 2095 | | | | | |

| | | | | | | | | | | |
|---|---|---|---|---|---|---|---|---|---|---|
| caa | gcc | tgg | gac | ctc | tat | tat | cat | gtg | ttc | cga | cga | atc | tca | aag | 6418 |
| Gln | Ala | Trp | Asp | Leu | Tyr | Tyr | His | Val | Phe | Arg | Arg | Ile | Ser | Lys | |
| | | 2100 | | | | 2105 | | | | 2110 | | | | | |

| | | | | | | | | | | |
|---|---|---|---|---|---|---|---|---|---|---|
| cag | ctg | cct | cag | ctc | aca | tcc | tta | gag | ctg | caa | tat | gtt | tcc | cca | 6463 |
| Gln | Leu | Pro | Gln | Leu | Thr | Ser | Leu | Glu | Leu | Gln | Tyr | Val | Ser | Pro | |
| | | 2115 | | | | 2120 | | | | 2125 | | | | | |

| | | | | | | | | | | |
|---|---|---|---|---|---|---|---|---|---|---|
| aaa | ctt | ctg | atg | tgc | cgg | gac | ctt | gaa | ttg | gct | gtg | cca | gga | aca | 6508 |
| Lys | Leu | Leu | Met | Cys | Arg | Asp | Leu | Glu | Leu | Ala | Val | Pro | Gly | Thr | |
| | | 2130 | | | | 2135 | | | | 2140 | | | | | |

| | | | | | | | | | | |
|---|---|---|---|---|---|---|---|---|---|---|
| tat | gac | ccc | aac | cag | cca | atc | att | cgc | att | cag | tcc | ata | gca | ccg | 6553 |
| Tyr | Asp | Pro | Asn | Gln | Pro | Ile | Ile | Arg | Ile | Gln | Ser | Ile | Ala | Pro | |
| | | 2145 | | | | 2150 | | | | 2155 | | | | | |

| | | | | | | | | | | |
|---|---|---|---|---|---|---|---|---|---|---|
| tct | ttg | caa | gtc | atc | aca | tcc | aag | cag | agg | ccc | cgg | aaa | ttg | aca | 6598 |
| Ser | Leu | Gln | Val | Ile | Thr | Ser | Lys | Gln | Arg | Pro | Arg | Lys | Leu | Thr | |
| | | 2160 | | | | 2165 | | | | 2170 | | | | | |

| | | | | | | | | | | |
|---|---|---|---|---|---|---|---|---|---|---|
| ctt | atg | ggc | agc | aac | gga | cat | gag | ttt | gtt | ttc | ctt | cta | aaa | ggc | 6643 |
| Leu | Met | Gly | Ser | Asn | Gly | His | Glu | Phe | Val | Phe | Leu | Leu | Lys | Gly | |
| | | 2175 | | | | 2180 | | | | 2185 | | | | | |

| | | | | | | | | | | |
|---|---|---|---|---|---|---|---|---|---|---|
| cat | gaa | gat | ctg | cgc | cag | gat | gag | cgt | gtg | atg | cag | ctc | ttc | ggc | 6688 |
| His | Glu | Asp | Leu | Arg | Gln | Asp | Glu | Arg | Val | Met | Gln | Leu | Phe | Gly | |
| | | 2190 | | | | 2195 | | | | 2200 | | | | | |

| | | | | | | | | | | |
|---|---|---|---|---|---|---|---|---|---|---|
| ctg | gtt | aac | acc | ctt | ctg | gcc | aat | gac | cca | aca | tct | ctt | cgg | aaa | 6733 |
| Leu | Val | Asn | Thr | Leu | Leu | Ala | Asn | Asp | Pro | Thr | Ser | Leu | Arg | Lys | |
| | | 2205 | | | | 2210 | | | | 2215 | | | | | |

| | | | | | | | | | | |
|---|---|---|---|---|---|---|---|---|---|---|
| aac | ctc | agc | atc | cag | aga | tac | gct | gtc | atc | cct | tta | tcg | acc | aac | 6778 |
| Asn | Leu | Ser | Ile | Gln | Arg | Tyr | Ala | Val | Ile | Pro | Leu | Ser | Thr | Asn | |
| | | 2220 | | | | 2225 | | | | 2230 | | | | | |

| | | | | | | | | | | |
|---|---|---|---|---|---|---|---|---|---|---|
| tcg | ggc | ctc | att | ggc | tgg | gtt | ccc | cac | tgt | gac | aca | ctg | cac | gcc | 6823 |
| Ser | Gly | Leu | Ile | Gly | Trp | Val | Pro | His | Cys | Asp | Thr | Leu | His | Ala | |
| | | 2235 | | | | 2240 | | | | 2245 | | | | | |

| | | | | | | | | | | |
|---|---|---|---|---|---|---|---|---|---|---|
| ctc | atc | cgg | gac | tac | agg | gag | aag | aag | aag | atc | ctt | ctc | aac | atc | 6868 |
| Leu | Ile | Arg | Asp | Tyr | Arg | Glu | Lys | Lys | Lys | Ile | Leu | Leu | Asn | Ile | |
| | | 2250 | | | | 2255 | | | | 2260 | | | | | |

| | | | | | | | | | | |
|---|---|---|---|---|---|---|---|---|---|---|
| gag | cat | cgc | atc | atg | ttg | cgg | atg | gct | ccg | gac | tat | gac | cac | ttg | 6913 |
| Glu | His | Arg | Ile | Met | Leu | Arg | Met | Ala | Pro | Asp | Tyr | Asp | His | Leu | |
| | | 2265 | | | | 2270 | | | | 2275 | | | | | |

| | | | | | | | | | | |
|---|---|---|---|---|---|---|---|---|---|---|
| act | ctg | atg | cag | aag | gtg | gag | gtg | ttt | gag | cat | gcc | gtc | aat | aat | 6958 |
| Thr | Leu | Met | Gln | Lys | Val | Glu | Val | Phe | Glu | His | Ala | Val | Asn | Asn | |
| | | 2280 | | | | 2285 | | | | 2290 | | | | | |

| | | | | | | | | | | |
|---|---|---|---|---|---|---|---|---|---|---|
| aca | gct | ggg | gac | gac | ctg | gcc | aag | ctg | ctg | tgg | ctg | aaa | agc | ccc | 7003 |
| Thr | Ala | Gly | Asp | Asp | Leu | Ala | Lys | Leu | Leu | Trp | Leu | Lys | Ser | Pro | |
| | | 2295 | | | | 2300 | | | | 2305 | | | | | |

| | | | | | | | | | | |
|---|---|---|---|---|---|---|---|---|---|---|
| agc | tcc | gag | gtg | tgg | ttt | gac | cga | aga | acc | aat | tat | acc | cgt | tct | 7048 |
| Ser | Ser | Glu | Val | Trp | Phe | Asp | Arg | Arg | Thr | Asn | Tyr | Thr | Arg | Ser | |
| | | 2310 | | | | 2315 | | | | 2320 | | | | | |

| | | | | | | | | | | |
|---|---|---|---|---|---|---|---|---|---|---|
| tta | gcg | gtc | atg | tca | atg | gtt | ggg | tat | att | tta | ggc | ctg | gga | gat | 7093 |
| Leu | Ala | Val | Met | Ser | Met | Val | Gly | Tyr | Ile | Leu | Gly | Leu | Gly | Asp | |
| | 2325 | | | | 2330 | | | | | 2335 | | | | | |
| aga | cac | cca | tcc | aac | ctg | atg | ctg | gac | cgt | ctg | agt | ggg | aag | atc | 7138 |
| Arg | His | Pro | Ser | Asn | Leu | Met | Leu | Asp | Arg | Leu | Ser | Gly | Lys | Ile | |
| | 2340 | | | | 2345 | | | | | 2350 | | | | | |
| ctg | cac | att | gac | ttt | ggg | gac | tgc | ttt | gag | gtt | gct | atg | acc | cga | 7183 |
| Leu | His | Ile | Asp | Phe | Gly | Asp | Cys | Phe | Glu | Val | Ala | Met | Thr | Arg | |
| | 2355 | | | | 2360 | | | | | 2365 | | | | | |
| gag | aag | ttt | cca | gag | aag | att | cca | ttt | aga | cta | aca | aga | atg | ttg | 7228 |
| Glu | Lys | Phe | Pro | Glu | Lys | Ile | Pro | Phe | Arg | Leu | Thr | Arg | Met | Leu | |
| | 2370 | | | | 2375 | | | | | 2380 | | | | | |
| acc | aat | gct | atg | gag | gtt | aca | ggc | ctg | gat | ggc | aac | tac | aga | atc | 7273 |
| Thr | Asn | Ala | Met | Glu | Val | Thr | Gly | Leu | Asp | Gly | Asn | Tyr | Arg | Ile | |
| | 2385 | | | | 2390 | | | | | 2395 | | | | | |
| aca | tgc | cac | aca | gtg | atg | gag | gtg | ctg | cga | gag | cac | aag | gac | agt | 7318 |
| Thr | Cys | His | Thr | Val | Met | Glu | Val | Leu | Arg | Glu | His | Lys | Asp | Ser | |
| | 2400 | | | | 2405 | | | | | 2410 | | | | | |
| gtc | atg | gcc | gtg | ctg | gaa | gcc | ttt | gtc | tat | gac | ccc | ttg | ctg | aac | 7363 |
| Val | Met | Ala | Val | Leu | Glu | Ala | Phe | Val | Tyr | Asp | Pro | Leu | Leu | Asn | |
| | 2415 | | | | 2420 | | | | | 2425 | | | | | |
| tgg | agg | ctg | atg | gac | aca | aat | acc | aaa | ggc | aac | aag | cga | tcc | cga | 7408 |
| Trp | Arg | Leu | Met | Asp | Thr | Asn | Thr | Lys | Gly | Asn | Lys | Arg | Ser | Arg | |
| | 2430 | | | | 2435 | | | | | 2440 | | | | | |
| acg | agg | acg | gat | tcc | tac | tct | gct | ggc | cag | tca | gtc | gaa | att | ttg | 7453 |
| Thr | Arg | Thr | Asp | Ser | Tyr | Ser | Ala | Gly | Gln | Ser | Val | Glu | Ile | Leu | |
| | 2445 | | | | 2450 | | | | | 2455 | | | | | |
| gac | ggt | gtg | gaa | ctt | gga | gag | cca | gcc | cat | aag | aaa | acg | ggg | acc | 7498 |
| Asp | Gly | Val | Glu | Leu | Gly | Glu | Pro | Ala | His | Lys | Lys | Thr | Gly | Thr | |
| | 2460 | | | | 2465 | | | | | 2470 | | | | | |
| aca | gtg | cca | gaa | tct | att | cat | tct | ttc | att | gga | gac | ggt | ttg | gtg | 7543 |
| Thr | Val | Pro | Glu | Ser | Ile | His | Ser | Phe | Ile | Gly | Asp | Gly | Leu | Val | |
| | 2475 | | | | 2480 | | | | | 2485 | | | | | |
| aaa | cca | gag | gcc | cta | aat | aag | aaa | gct | atc | cag | att | att | aac | agg | 7588 |
| Lys | Pro | Glu | Ala | Leu | Asn | Lys | Lys | Ala | Ile | Gln | Ile | Ile | Asn | Arg | |
| | 2490 | | | | 2495 | | | | | 2500 | | | | | |
| gtt | cga | gat | aag | ctc | act | ggt | cgg | gac | ttc | tct | cat | gat | gac | act | 7633 |
| Val | Arg | Asp | Lys | Leu | Thr | Gly | Arg | Asp | Phe | Ser | His | Asp | Asp | Thr | |
| | 2505 | | | | 2510 | | | | | 2515 | | | | | |
| ttg | gat | gtt | cca | acg | caa | gtt | gag | ctg | ctc | atc | aaa | caa | gcg | aca | 7678 |
| Leu | Asp | Val | Pro | Thr | Gln | Val | Glu | Leu | Leu | Ile | Lys | Gln | Ala | Thr | |
| | 2520 | | | | 2525 | | | | | 2530 | | | | | |
| tcc | cat | gaa | aac | ctc | tgc | cag | tgc | tat | att | ggc | tgg | tgc | cct | ttc | 7723 |
| Ser | His | Glu | Asn | Leu | Cys | Gln | Cys | Tyr | Ile | Gly | Trp | Cys | Pro | Phe | |
| | 2535 | | | | 2540 | | | | | 2545 | | | | | |

| | |
|---|---|
| tgg taa ctggaggccc agatgtgccc atcacgtttt ttctgaggct tttgtacttt | 7779 |
| Trp | |
| agtaaatgct tccactaaac tgaaaccatg gtgagaaagt ttgactttgt taaatatttt | 7839 |
| gaaatgtaaa tgaaagaac tactgtatat taaaagttgg tttgaaccaa cttttctagct | 7899 |
| gctgttgaag aatatattgt cagaaacaca aggcttgatt tggttcccag dacagtgaaa | 7959 |
| caatagtaat accacgtaaa tcaagccatt cattttgggg aacagaagat ccataacttt | 8019 |
| agaaatacgg gttttgactt aactcacaag agaactcatc ataagtactt gctgatggaa | 8079 |
| gaatgaccta gttgctcctc tcaacatggg tacagcaaac tcagcacagc caagaagcct | 8139 |
| caggtcgtgg agaacatgga ttaggatcct agactgtaaa gacacagaag atgctgacct | 8199 |
| caccctgcc acctatccca agacctcact ggtctgtgga cagcagcaga aatgtttgca | 8259 |

```
agataggcca aaatgagtac aaaaggtctg tcttccatca gacccagtga tgctgcgact      8319
cacacgcttc aattcaagac ctgaccgcta gtagggaggt ttattcagat cgctggcagc      8379
ctcggctgag cagatgcaca gaggggatca ctgtgcagtg ggaccaccct cactggcctt      8439
ctgcagcagg gttctgggat gttttcagtg gtcaaaatac tctgtttaga gcaagggctc      8499
agaaaacaga atactgtca tggaggtgct gaacacaggg aaggtctggt acatattgga       8559
aattatgagc agaacaaata ctcaactaaa tgcacaaagt ataaagtgta gccatgtcta      8619
gacaccatgt tgtatcagaa taatttttgt gccaataaat gacatcagaa ttttaaacat      8679
a                                                                     8680
```

<210> SEQ ID NO 4
<211> LENGTH: 2549
<212> TYPE: PRT
<213> ORGANISM: Homo sapiens

<400> SEQUENCE: 4

```
Met Leu Gly Thr Gly Pro Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285
```

-continued

```
Ile Thr Gln Gln Gln Leu Val His Asp Lys Tyr Cys Lys Asp Leu Met
290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
690                 695                 700

Phe Glu Ile Arg Glu Leu Ala Ile Cys Thr Val Gly Arg Leu Ser Ser
```

```
            705                 710                 715                 720
        Met Asn Pro Ala Phe Val Met Pro Phe Leu Arg Lys Met Leu Ile Gln
                        725                 730                 735

Ile Leu Thr Glu Leu Glu His Ser Gly Ile Gly Arg Ile Lys Glu Gln
                        740                 745                 750

Ser Ala Arg Met Leu Gly His Leu Val Ser Asn Ala Pro Arg Leu Ile
                        755                 760                 765

Arg Pro Tyr Met Glu Pro Ile Leu Lys Ala Leu Ile Leu Lys Leu Lys
                        770                 775                 780

Asp Pro Asp Pro Asp Pro Asn Pro Gly Val Ile Asn Asn Val Leu Ala
        785                 790                 795                 800

Thr Ile Gly Glu Leu Ala Gln Val Ser Gly Leu Glu Met Arg Lys Trp
                        805                 810                 815

Val Asp Glu Leu Phe Ile Ile Ile Met Asp Met Leu Gln Asp Ser Ser
                        820                 825                 830

Leu Leu Ala Lys Arg Gln Val Ala Leu Trp Thr Leu Gly Gln Leu Val
                        835                 840                 845

Ala Ser Thr Gly Tyr Val Val Glu Pro Tyr Arg Lys Tyr Pro Thr Leu
        850                 855                 860

Leu Glu Val Leu Leu Asn Phe Leu Lys Thr Glu Gln Asn Gln Gly Thr
        865                 870                 875                 880

Arg Arg Glu Ala Ile Arg Val Leu Gly Leu Leu Gly Ala Leu Asp Pro
                        885                 890                 895

Tyr Lys His Lys Val Asn Ile Gly Met Ile Asp Gln Ser Arg Asp Ala
                        900                 905                 910

Ser Ala Val Ser Leu Ser Glu Ser Lys Ser Ser Gln Asp Ser Ser Asp
                        915                 920                 925

Tyr Ser Thr Ser Glu Met Leu Val Asn Met Gly Asn Leu Pro Leu Asp
                        930                 935                 940

Glu Phe Tyr Pro Ala Val Ser Met Val Ala Leu Met Arg Ile Phe Arg
        945                 950                 955                 960

Asp Gln Ser Leu Ser His His Thr Met Val Val Gln Ala Ile Thr
                        965                 970                 975

Phe Ile Phe Lys Ser Leu Gly Leu Lys Cys Val Gln Phe Leu Pro Gln
                        980                 985                 990

Val Met Pro Thr Phe Leu Asn Val Ile Arg Val Cys Asp Gly Ala Ile
                        995                 1000                1005

Arg Glu Phe Leu Phe Gln Gln Leu Gly Met Leu Val Ser Phe Val
            1010                1015                1020

Lys Ser His Ile Arg Pro Tyr Met Asp Glu Ile Val Thr Leu Met
            1025                1030                1035

Arg Glu Phe Trp Val Met Asn Thr Ser Ile Gln Ser Thr Ile Ile
            1040                1045                1050

Leu Leu Ile Glu Gln Ile Val Ala Leu Gly Gly Glu Phe Lys
            1055                1060                1065

Leu Tyr Leu Pro Gln Leu Ile Pro His Met Leu Arg Val Phe Met
            1070                1075                1080

His Asp Asn Ser Pro Gly Arg Ile Val Ser Ile Lys Leu Leu Ala
            1085                1090                1095

Ala Ile Gln Leu Phe Gly Ala Asn Leu Asp Asp Tyr Leu His Leu
            1100                1105                1110

Leu Leu Pro Pro Ile Val Lys Leu Phe Asp Ala Pro Glu Ala Pro
            1115                1120                1125
```

```
Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Asp Pro Leu Ile Tyr Gln
    1220                1225                1230

His Arg Met Leu Arg Ser Gly Gln Gly Asp Ala Leu Ala Ser Gly
    1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
    1265                1270                1275

Asp Trp Leu Glu Trp Leu Arg Arg Leu Ser Leu Glu Leu Leu Lys
    1280                1285                1290

Asp Ser Ser Ser Pro Ser Leu Arg Ser Cys Trp Ala Leu Ala Gln
    1295                1300                1305

Ala Tyr Asn Pro Met Ala Arg Asp Leu Phe Asn Ala Ala Phe Val
    1310                1315                1320

Ser Cys Trp Ser Glu Leu Asn Glu Asp Gln Gln Asp Glu Leu Ile
    1325                1330                1335

Arg Ser Ile Glu Leu Ala Leu Thr Ser Gln Asp Ile Ala Glu Val
    1340                1345                1350

Thr Gln Thr Leu Leu Asn Leu Ala Glu Phe Met Glu His Ser Asp
    1355                1360                1365

Lys Gly Pro Leu Pro Leu Arg Asp Asp Asn Gly Ile Val Leu Leu
    1370                1375                1380

Gly Glu Arg Ala Ala Lys Cys Arg Ala Tyr Ala Lys Ala Leu His
    1385                1390                1395

Tyr Lys Glu Leu Glu Phe Gln Lys Gly Pro Thr Pro Ala Ile Leu
    1400                1405                1410

Glu Ser Leu Ile Ser Ile Asn Asn Lys Leu Gln Gln Pro Glu Ala
    1415                1420                1425

Ala Ala Gly Val Leu Glu Tyr Ala Met Lys His Phe Gly Glu Leu
    1430                1435                1440

Glu Ile Gln Ala Thr Trp Tyr Glu Lys Leu His Glu Trp Glu Asp
    1445                1450                1455

Ala Leu Val Ala Tyr Asp Lys Lys Met Asp Thr Asn Lys Asp Asp
    1460                1465                1470

Pro Glu Leu Met Leu Gly Arg Met Arg Cys Leu Glu Ala Leu Gly
    1475                1480                1485

Glu Trp Gly Gln Leu His Gln Gln Cys Cys Glu Lys Trp Thr Leu
    1490                1495                1500

Val Asn Asp Glu Thr Gln Ala Lys Met Ala Arg Met Ala Ala Ala
    1505                1510                1515
```

```
Ala Ala Trp Gly Leu Gly Gln Trp Asp Ser Met Glu Glu Tyr Thr
    1520                1525                1530

Cys Met Ile Pro Arg Asp Thr His Asp Gly Ala Phe Tyr Arg Ala
    1535                1540                1545

Val Leu Ala Leu His Gln Asp Leu Phe Ser Leu Ala Gln Gln Cys
    1550                1555                1560

Ile Asp Lys Ala Arg Asp Leu Leu Asp Ala Glu Leu Thr Ala Met
    1565                1570                1575

Ala Gly Glu Ser Tyr Ser Arg Ala Tyr Gly Ala Met Val Ser Cys
    1580                1585                1590

His Met Leu Ser Glu Leu Glu Glu Val Ile Gln Tyr Lys Leu Val
    1595                1600                1605

Pro Glu Arg Arg Glu Ile Ile Arg Gln Ile Trp Trp Glu Arg Leu
    1610                1615                1620

Gln Gly Cys Gln Arg Ile Val Glu Asp Trp Gln Lys Ile Leu Met
    1625                1630                1635

Val Arg Ser Leu Val Val Ser Pro His Glu Asp Met Arg Thr Trp
    1640                1645                1650

Leu Lys Tyr Ala Ser Leu Cys Gly Lys Ser Gly Arg Leu Ala Leu
    1655                1660                1665

Ala His Lys Thr Leu Val Leu Leu Leu Gly Val Asp Pro Ser Arg
    1670                1675                1680

Gln Leu Asp His Pro Leu Pro Thr Val His Pro Gln Val Thr Tyr
    1685                1690                1695

Ala Tyr Met Lys Asn Met Trp Lys Ser Ala Arg Lys Ile Asp Ala
    1700                1705                1710

Phe Gln His Met Gln His Phe Val Gln Thr Met Gln Gln Gln Ala
    1715                1720                1725

Gln His Ala Ile Ala Thr Glu Asp Gln Gln His Lys Gln Glu Leu
    1730                1735                1740

His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800

Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Thr Ala Thr Thr Thr Ala Ser Thr Glu Gly Ser Asn
    1835                1840                1845

Ser Glu Ser Glu Ala Glu Ser Thr Glu Asn Ser Pro Thr Pro Ser
    1850                1855                1860

Pro Leu Gln Lys Lys Val Thr Glu Asp Leu Ser Lys Thr Leu Leu
    1865                1870                1875

Met Tyr Thr Val Pro Ala Val Gln Gly Phe Phe Arg Ser Ile Ser
    1880                1885                1890

Leu Ser Arg Gly Asn Asn Leu Gln Asp Thr Leu Arg Val Leu Thr
    1895                1900                1905

Leu Trp Phe Asp Tyr Gly His Trp Pro Asp Val Asn Glu Ala Leu
```

```
                    1910                1915                1920
Val Glu Gly Val Lys Ala Ile Gln Ile Asp Thr Trp Leu Gln Val
        1925                1930                1935

Ile Pro Gln Leu Ile Ala Arg Ile Asp Thr Pro Arg Pro Leu Val
        1940                1945                1950

Gly Arg Leu Ile His Gln Leu Leu Thr Asp Ile Gly Arg Tyr His
        1955                1960                1965

Pro Gln Ala Leu Ile Tyr Pro Leu Thr Val Ala Ser Lys Ser Thr
        1970                1975                1980

Thr Thr Ala Arg His Asn Ala Ala Asn Lys Ile Leu Lys Asn Met
        1985                1990                1995

Cys Glu His Ser Asn Thr Leu Val Gln Gln Ala Met Met Val Ser
        2000                2005                2010

Glu Glu Leu Ile Arg Val Ala Ile Leu Trp His Glu Met Trp His
        2015                2020                2025

Glu Gly Leu Glu Glu Ala Ser Arg Leu Tyr Phe Gly Glu Arg Asn
        2030                2035                2040

Val Lys Gly Met Phe Glu Val Leu Glu Pro Leu His Ala Met Met
        2045                2050                2055

Glu Arg Gly Pro Gln Thr Leu Lys Glu Thr Ser Phe Asn Gln Ala
        2060                2065                2070

Tyr Gly Arg Asp Leu Met Glu Ala Gln Glu Trp Cys Arg Lys Tyr
        2075                2080                2085

Met Lys Ser Gly Asn Val Lys Asp Leu Thr Gln Ala Trp Asp Leu
        2090                2095                2100

Tyr Tyr His Val Phe Arg Arg Ile Ser Lys Gln Leu Pro Gln Leu
        2105                2110                2115

Thr Ser Leu Glu Leu Gln Tyr Val Ser Pro Lys Leu Leu Met Cys
        2120                2125                2130

Arg Asp Leu Glu Leu Ala Val Pro Gly Thr Tyr Asp Pro Asn Gln
        2135                2140                2145

Pro Ile Ile Arg Ile Gln Ser Ile Ala Pro Ser Leu Gln Val Ile
        2150                2155                2160

Thr Ser Lys Gln Arg Pro Arg Lys Leu Thr Leu Met Gly Ser Asn
        2165                2170                2175

Gly His Glu Phe Val Phe Leu Leu Lys Gly His Glu Asp Leu Arg
        2180                2185                2190

Gln Asp Glu Arg Val Met Gln Leu Phe Gly Leu Val Asn Thr Leu
        2195                2200                2205

Leu Ala Asn Asp Pro Thr Ser Leu Arg Lys Asn Leu Ser Ile Gln
        2210                2215                2220

Arg Tyr Ala Val Ile Pro Leu Ser Thr Asn Ser Gly Leu Ile Gly
        2225                2230                2235

Trp Val Pro His Cys Asp Thr Leu His Ala Leu Ile Arg Asp Tyr
        2240                2245                2250

Arg Glu Lys Lys Lys Ile Leu Leu Asn Ile Glu His Arg Ile Met
        2255                2260                2265

Leu Arg Met Ala Pro Asp Tyr Asp His Leu Thr Leu Met Gln Lys
        2270                2275                2280

Val Glu Val Phe Glu His Ala Val Asn Asn Thr Ala Gly Asp Asp
        2285                2290                2295

Leu Ala Lys Leu Leu Trp Leu Lys Ser Pro Ser Ser Glu Val Trp
        2300                2305                2310
```

```
Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545
```

<210> SEQ ID NO 5
<211> LENGTH: 8155
<212> TYPE: DNA
<213> ORGANISM: Homo sapiens
<220> FEATURE:
<221> NAME/KEY: CDS
<222> LOCATION: (19)..(7668)

<400> SEQUENCE: 5

```
cgcgaacctc agggcaag atg ctt gga acc gga cct gcc gcc gcc acc acc       51
                    Met Leu Gly Thr Gly Pro Ala Ala Ala Thr Thr
                    1               5                   10 gct gcc acc aca tct agc aat gtg agc gtc ctg cag cag ttt gcc agt       99
Ala Ala Thr Thr Ser Ser Asn Val Ser Val Leu Gln Gln Phe Ala Ser
            15                  20                  25 ggc cta aag agc cgg aat gag gaa acc agg gcc aaa gcc gcc aag gag      147
Gly Leu Lys Ser Arg Asn Glu Glu Thr Arg Ala Lys Ala Ala Lys Glu
        30                  35                  40 ctc cag cac tat gtc acc atg gaa ctc cga gag atg agt caa gag gag      195
Leu Gln His Tyr Val Thr Met Glu Leu Arg Glu Met Ser Gln Glu Glu
    45                  50                  55 tct act cgc ttc tat gac caa ctg aac cat cac att ttt gaa ttg gtt      243
Ser Thr Arg Phe Tyr Asp Gln Leu Asn His His Ile Phe Glu Leu Val
60                  65                  70                  75
```

-continued

| | | |
|---|---|---|
| tcc agc tca gat gcc aat gag agg aaa ggt ggc atc ttg gcc ata gct<br>Ser Ser Ser Asp Ala Asn Glu Arg Lys Gly Gly Ile Leu Ala Ile Ala<br>80                            85                           90 | 291 | |
| agc ctc ata gga gtg gaa ggt ggg aat gcc acc cga att ggc aga ttt<br>Ser Leu Ile Gly Val Glu Gly Gly Asn Ala Thr Arg Ile Gly Arg Phe<br>             95                       100                     105 | 339 | |
| gcc aac tat ctt cgg aac ctc ctc ccc tcc aat gac cca gtt gtc atg<br>Ala Asn Tyr Leu Arg Asn Leu Leu Pro Ser Asn Asp Pro Val Val Met<br>          110                     115                     120 | 387 | |
| gaa atg gca tcc aag gcc att ggc cgt ctt gcc atg gca ggg gac act<br>Glu Met Ala Ser Lys Ala Ile Gly Arg Leu Ala Met Ala Gly Asp Thr<br>125                          130                     135 | 435 | |
| ttt acc gct gag tac gtg gaa ttt gag gtg aag cga gcc ctg gaa tgg<br>Phe Thr Ala Glu Tyr Val Glu Phe Glu Val Lys Arg Ala Leu Glu Trp<br>140                        145                     150                155 | 483 | |
| ctg ggt gct gac cgc aat gag ggc cgg aga cat gca gct gtc ctg gtt<br>Leu Gly Ala Asp Arg Asn Glu Gly Arg Arg His Ala Ala Val Leu Val<br>                      160                     165                 170 | 531 | |
| ctc cgt gag ctg gcc atc agc gtc cct acc ttc ttc cag caa gtg<br>Leu Arg Glu Leu Ala Ile Ser Val Pro Thr Phe Phe Gln Gln Val<br>               175                     180                     185 | 579 | |
| caa ccc ttc ttt gac aac att ttt gtg gcc gtg tgg gac ccc aaa cag<br>Gln Pro Phe Phe Asp Asn Ile Phe Val Ala Val Trp Asp Pro Lys Gln<br>                      190                     195                 200 | 627 | |
| gcc atc cgt gag gga gct gta gcc gcc ctt cgt gcc tgt ctg att ctc<br>Ala Ile Arg Glu Gly Ala Val Ala Ala Leu Arg Ala Cys Leu Ile Leu<br>205                          210                     215 | 675 | |
| aca acc cag cgt gag ccg aag gag atg cag aag cct cag tgg tac agg<br>Thr Thr Gln Arg Glu Pro Lys Glu Met Gln Lys Pro Gln Trp Tyr Arg<br>220                          225                     230                235 | 723 | |
| cac aca ttt gaa gaa gca gag aag gga ttt gat gag acc ttg gcc aaa<br>His Thr Phe Glu Glu Ala Glu Lys Gly Phe Asp Glu Thr Leu Ala Lys<br>                      240                     245                     250 | 771 | |
| gag aag ggc atg aat cgg gat gat cgg atc cat gga gcc ttg ttg atc<br>Glu Lys Gly Met Asn Arg Asp Asp Arg Ile His Gly Ala Leu Leu Ile<br>                      255                     260                 265 | 819 | |
| ctt aac gag ctg gtc cga atc agc agc atg gag gga gag cgt ctg aga<br>Leu Asn Glu Leu Val Arg Ile Ser Ser Met Glu Gly Glu Arg Leu Arg<br>        270                     275                     280 | 867 | |
| gaa gaa atg gaa gaa atc aca cag cag cag ctg gta cac gac aag tac<br>Glu Glu Met Glu Glu Ile Thr Gln Gln Gln Leu Val His Asp Lys Tyr<br>285                          290                     295 | 915 | |
| tgc aaa gat ctc atg ggc ttc gga aca aaa cct cgt cac att acc ccc<br>Cys Lys Asp Leu Met Gly Phe Gly Thr Lys Pro Arg His Ile Thr Pro<br>300                          305                     310                315 | 963 | |
| ttc acc agt ttc cag gct gta cag ccc cag cag tca aat gcc ttg gtg<br>Phe Thr Ser Phe Gln Ala Val Gln Pro Gln Gln Ser Asn Ala Leu Val<br>                      320                     325                     330 | 1011 | |
| ggg ctg ctg ggg tac agc tct cac caa ggc ctc atg gga ttt ggg acc<br>Gly Leu Leu Gly Tyr Ser Ser His Gln Gly Leu Met Gly Phe Gly Thr<br>                      335                     340                 345 | 1059 | |
| tcc ccc agt cca gct aag tcc acc ctg gtg gag agc cgg tgt tgc aga<br>Ser Pro Ser Pro Ala Lys Ser Thr Leu Val Glu Ser Arg Cys Cys Arg<br>                    350                     355                 360 | 1107 | |
| gac ttg atg gag gag aaa ttt gat cag gtg tgc cag tgg gtg ctg aaa<br>Asp Leu Met Glu Glu Lys Phe Asp Gln Val Cys Gln Trp Val Leu Lys<br>365                          370                     375 | 1155 | |
| tgc agg aat agc aag aac tcg ctg atc caa atg aca atc ctt aat ttg<br>Cys Arg Asn Ser Lys Asn Ser Leu Ile Gln Met Thr Ile Leu Asn Leu | 1203 | |

-continued

| | | | | | | | | | | | | | | | | |
|---|---|---|---|---|---|---|---|---|---|---|---|---|---|---|---|---|
| 380 | | | | | 385 | | | | | 390 | | | | | 395 | |

```
ttg ccc cgc ttg gct gca ttc cga cct tct gcc ttc aca gat acc cag      1251
Leu Pro Arg Leu Ala Ala Phe Arg Pro Ser Ala Phe Thr Asp Thr Gln
            400                 405                 410 tat ctc caa gat acc atg aac cat gtc cta agc tgt gtc aag aag gag      1299
Tyr Leu Gln Asp Thr Met Asn His Val Leu Ser Cys Val Lys Lys Glu
        415                 420                 425 aag gaa cgt aca gcg gcc ttc caa gcc ctg ggg cta ctt tct gtg gct      1347
Lys Glu Arg Thr Ala Ala Phe Gln Ala Leu Gly Leu Leu Ser Val Ala
    430                 435                 440 gtg agg tct gag ttt aag gtc tat ttg cct cgc gtg ctg gac atc atc      1395
Val Arg Ser Glu Phe Lys Val Tyr Leu Pro Arg Val Leu Asp Ile Ile
445                 450                 455 cga gcg gcc ctg ccc cca aag gac ttc gcc cat aag agg cag aag gca      1443
Arg Ala Ala Leu Pro Pro Lys Asp Phe Ala His Lys Arg Gln Lys Ala
460                 465                 470                 475 atg cag gtg gac gcc aca gtc ttc act tgc atc agc atg ctg gct cga      1491
Met Gln Val Asp Ala Thr Val Phe Thr Cys Ile Ser Met Leu Ala Arg
                480                 485                 490 gca atg ggg cca ggc atc cag cag gat atc aag gag ctg ctg gag ccc      1539
Ala Met Gly Pro Gly Ile Gln Gln Asp Ile Lys Glu Leu Leu Glu Pro
            495                 500                 505 atg ctg gca gtg gga cta agc cct gcc ctc act gca gtg ctc tac gac      1587
Met Leu Ala Val Gly Leu Ser Pro Ala Leu Thr Ala Val Leu Tyr Asp
        510                 515                 520 ctg agc cgt cag att cca cag cta aag aag gac att caa gat ggg cta      1635
Leu Ser Arg Gln Ile Pro Gln Leu Lys Lys Asp Ile Gln Asp Gly Leu
    525                 530                 535 ctg aaa atg ctg tcc ctg gtc ctt atg cac aaa ccc ctt cgc cac cca      1683
Leu Lys Met Leu Ser Leu Val Leu Met His Lys Pro Leu Arg His Pro
540                 545                 550                 555 ggc atg ccc aag ggc ctg gcc cat cag ctg gcc tct cct ggc ctc acg      1731
Gly Met Pro Lys Gly Leu Ala His Gln Leu Ala Ser Pro Gly Leu Thr
                560                 565                 570 acc ctc cct gag gcc agc gat gtg ggc agc atc act ctt gcc ctc cga      1779
Thr Leu Pro Glu Ala Ser Asp Val Gly Ser Ile Thr Leu Ala Leu Arg
            575                 580                 585 acg ctt ggc agc ttt gaa ttt gaa ggc cac tct ctg acc caa ttt gtt      1827
Thr Leu Gly Ser Phe Glu Phe Glu Gly His Ser Leu Thr Gln Phe Val
        590                 595                 600 cgc cac tgt gcg gat cat ttt ctg aac agt gag cac aag gag atc cgc      1875
Arg His Cys Ala Asp His Phe Leu Asn Ser Glu His Lys Glu Ile Arg
    605                 610                 615 atg gag gct gcc cgc acc tgc tcc cgc ctg ctc aca ccc tcc atc cac      1923
Met Glu Ala Ala Arg Thr Cys Ser Arg Leu Leu Thr Pro Ser Ile His
620                 625                 630                 635 ctc atc agt ggc cat gct cat gtg gtt agc cag acc gca gtg caa gtg      1971
Leu Ile Ser Gly His Ala His Val Val Ser Gln Thr Ala Val Gln Val
                640                 645                 650 gtg gca gat gtg ctt agc aaa ctg ctc gta gtt ggg ata aca gat cct      2019
Val Ala Asp Val Leu Ser Lys Leu Leu Val Val Gly Ile Thr Asp Pro
            655                 660                 665 gac cct gac att cgc tac tgt gtc ttg gcg tcc ctg gac gag cgc ttt      2067
Asp Pro Asp Ile Arg Tyr Cys Val Leu Ala Ser Leu Asp Glu Arg Phe
        670                 675                 680 gat gca cac ctg gcc cag gcg gag aac ttg cag gcc ttg ttt gtg gct      2115
Asp Ala His Leu Ala Gln Ala Glu Asn Leu Gln Ala Leu Phe Val Ala
    685                 690                 695 ctg aat gac cag gtg ttt gag atc cgg gag ctg gcc atc tgc act gtg      2163
Leu Asn Asp Gln Val Phe Glu Ile Arg Glu Leu Ala Ile Cys Thr Val
```

```
Leu Asn Asp Gln Val Phe Glu Ile Arg Glu Leu Ala Ile Cys Thr Val
700                 705                 710                 715 ggc cga ctc agt agc atg aac cct gcc ttt gtc atg cct ttc ctg cgc    2211
Gly Arg Leu Ser Ser Met Asn Pro Ala Phe Val Met Pro Phe Leu Arg
            720                 725                 730 aag atg ctc atc cag att ttg aca gag ttg gag cac agt ggg att gga    2259
Lys Met Leu Ile Gln Ile Leu Thr Glu Leu Glu His Ser Gly Ile Gly
                735                 740                 745 aga atc aaa gag cag agt gcc cgc atg ctg ggg cac ctg gtc tcc aat    2307
Arg Ile Lys Glu Gln Ser Ala Arg Met Leu Gly His Leu Val Ser Asn
            750                 755                 760 gcc ccc cga ctc atc cgc ccc tac atg gag cct att ctg aag gca tta    2355
Ala Pro Arg Leu Ile Arg Pro Tyr Met Glu Pro Ile Leu Lys Ala Leu
        765                 770                 775 att ttg aaa ctg aaa gat cca gac cct gat cca aac cca ggt gtg atc    2403
Ile Leu Lys Leu Lys Asp Pro Asp Pro Asp Pro Asn Pro Gly Val Ile
780                 785                 790                 795 aat aat gtc ctg gca aca ata gga gaa ttg gca cag gtt agt ggc ctg    2451
Asn Asn Val Leu Ala Thr Ile Gly Glu Leu Ala Gln Val Ser Gly Leu
                800                 805                 810 gaa atg agg aaa tgg gtt gat gaa ctt ttt att atc atc atg gac atg    2499
Glu Met Arg Lys Trp Val Asp Glu Leu Phe Ile Ile Ile Met Asp Met
            815                 820                 825 ctc cag gat tcc tct ttg ttg gcc aaa agg cag gtg gct ctg tgg acc    2547
Leu Gln Asp Ser Ser Leu Leu Ala Lys Arg Gln Val Ala Leu Trp Thr
        830                 835                 840 ctg gga cag ttg gtg gcc agc act ggc tat gta gta gag ccc tac agg    2595
Leu Gly Gln Leu Val Ala Ser Thr Gly Tyr Val Val Glu Pro Tyr Arg
845                 850                 855 aag tac cct act ttg ctt gag gtg cta ctg aat ttt ctg aag act gag    2643
Lys Tyr Pro Thr Leu Leu Glu Val Leu Leu Asn Phe Leu Lys Thr Glu
860                 865                 870                 875 cag aac cag ggt aca cgc aga gag gcc atc cgt gtg tta ggg ctt tta    2691
Gln Asn Gln Gly Thr Arg Arg Glu Ala Ile Arg Val Leu Gly Leu Leu
                880                 885                 890 ggg gct ttg gat cct tac aag cac aaa gtg aac att ggc atg ata gac    2739
Gly Ala Leu Asp Pro Tyr Lys His Lys Val Asn Ile Gly Met Ile Asp
            895                 900                 905 cag tcc cgg gat gcc tct gct gtc agc ctg tca gaa tcc aag tca agt    2787
Gln Ser Arg Asp Ala Ser Ala Val Ser Leu Ser Glu Ser Lys Ser Ser
        910                 915                 920 cag gat tcc tct gac tat agc act agt gaa atg ctg gtc aac atg gga    2835
Gln Asp Ser Ser Asp Tyr Ser Thr Ser Glu Met Leu Val Asn Met Gly
925                 930                 935 aac ttg cct ctg gat gag ttc tac cca gct gtg tcc atg gtg gcc ctg    2883
Asn Leu Pro Leu Asp Glu Phe Tyr Pro Ala Val Ser Met Val Ala Leu
940                 945                 950                 955 atg cgg atc ttc cga gac cag tca ctc tct cat cat cac acc atg gtt    2931
Met Arg Ile Phe Arg Asp Gln Ser Leu Ser His His His Thr Met Val
                960                 965                 970 gtc cag gcc atc acc ttc atc ttc aag tcc ctg gga ctc aaa tgt gtg    2979
Val Gln Ala Ile Thr Phe Ile Phe Lys Ser Leu Gly Leu Lys Cys Val
            975                 980                 985 cag ttc ctg ccc cag gtc atg ccc acg ttc ctt aat gtc att cga gtc    3027
Gln Phe Leu Pro Gln Val Met Pro Thr Phe Leu Asn Val Ile Arg Val
        990                 995                 1000 tgt gat ggg gcc atc cgg gaa ttt ttg ttc cag cag ctg gga atg        3072
Cys Asp Gly Ala Ile Arg Glu Phe Leu Phe Gln Gln Leu Gly Met
    1005                1010                1015
```

| | | | | | | | | | | | |
|---|---|---|---|---|---|---|---|---|---|---|---|
| ttg | gtg | tcc | ttt | gtg | aag | agc | cac | atc | aga | cct | tat | atg | gat | gaa | 3117 |
| Leu | Val | Ser | Phe | Val | Lys | Ser | His | Ile | Arg | Pro | Tyr | Met | Asp | Glu | |
| 1020 | | | | 1025 | | | | | 1030 | | | | | | |

| ata | gtc | acc | ctc | atg | aga | gaa | ttc | tgg | gtc | atg | aac | acc | tca | att | 3162 |
|---|---|---|---|---|---|---|---|---|---|---|---|---|---|---|---|
| Ile | Val | Thr | Leu | Met | Arg | Glu | Phe | Trp | Val | Met | Asn | Thr | Ser | Ile | |
| 1035 | | | | | 1040 | | | | | 1045 | | | | | |

| cag | agc | acg | atc | att | ctt | ctc | att | gag | caa | att | gtg | gta | gct | ctt | 3207 |
|---|---|---|---|---|---|---|---|---|---|---|---|---|---|---|---|
| Gln | Ser | Thr | Ile | Ile | Leu | Leu | Ile | Glu | Gln | Ile | Val | Val | Ala | Leu | |
| 1050 | | | | | 1055 | | | | | 1060 | | | | | |

| ggg | ggt | gaa | ttt | aag | ctc | tac | ctg | ccc | cag | ctg | atc | cca | cac | atg | 3252 |
|---|---|---|---|---|---|---|---|---|---|---|---|---|---|---|---|
| Gly | Gly | Glu | Phe | Lys | Leu | Tyr | Leu | Pro | Gln | Leu | Ile | Pro | His | Met | |
| 1065 | | | | | 1070 | | | | | 1075 | | | | | |

| ctg | cgt | gtc | ttc | atg | cat | gac | aac | agc | cca | ggc | cgc | att | gtc | tct | 3297 |
|---|---|---|---|---|---|---|---|---|---|---|---|---|---|---|---|
| Leu | Arg | Val | Phe | Met | His | Asp | Asn | Ser | Pro | Gly | Arg | Ile | Val | Ser | |
| 1080 | | | | | 1085 | | | | | 1090 | | | | | |

| atc | aag | tta | ctg | gct | gca | atc | cag | ctg | ttt | ggc | gcc | aac | ctg | gat | 3342 |
|---|---|---|---|---|---|---|---|---|---|---|---|---|---|---|---|
| Ile | Lys | Leu | Leu | Ala | Ala | Ile | Gln | Leu | Phe | Gly | Ala | Asn | Leu | Asp | |
| 1095 | | | | | 1100 | | | | | 1105 | | | | | |

| gac | tac | ctg | cat | tta | ctg | ctg | cct | cct | att | gtt | aag | ttg | ttt | gat | 3387 |
|---|---|---|---|---|---|---|---|---|---|---|---|---|---|---|---|
| Asp | Tyr | Leu | His | Leu | Leu | Leu | Pro | Pro | Ile | Val | Lys | Leu | Phe | Asp | |
| 1110 | | | | | 1115 | | | | | 1120 | | | | | |

| gcc | cct | gaa | gct | cca | ctg | cca | tct | cga | aag | gca | gcg | cta | gag | act | 3432 |
|---|---|---|---|---|---|---|---|---|---|---|---|---|---|---|---|
| Ala | Pro | Glu | Ala | Pro | Leu | Pro | Ser | Arg | Lys | Ala | Ala | Leu | Glu | Thr | |
| 1125 | | | | | 1130 | | | | | 1135 | | | | | |

| gtg | gac | cgc | ctg | acg | gag | tcc | ctg | gat | ttc | act | gac | tat | gcc | tcc | 3477 |
|---|---|---|---|---|---|---|---|---|---|---|---|---|---|---|---|
| Val | Asp | Arg | Leu | Thr | Glu | Ser | Leu | Asp | Phe | Thr | Asp | Tyr | Ala | Ser | |
| 1140 | | | | | 1145 | | | | | 1150 | | | | | |

| cgg | atc | att | cac | cct | att | gtt | cga | aca | ctg | gac | cag | agc | cca | gaa | 3522 |
|---|---|---|---|---|---|---|---|---|---|---|---|---|---|---|---|
| Arg | Ile | Ile | His | Pro | Ile | Val | Arg | Thr | Leu | Asp | Gln | Ser | Pro | Glu | |
| 1155 | | | | | 1160 | | | | | 1165 | | | | | |

| ctg | cgc | tcc | aca | gcc | atg | gac | acg | ctg | tct | tca | ctt | gtt | ttt | cag | 3567 |
|---|---|---|---|---|---|---|---|---|---|---|---|---|---|---|---|
| Leu | Arg | Ser | Thr | Ala | Met | Asp | Thr | Leu | Ser | Ser | Leu | Val | Phe | Gln | |
| 1170 | | | | | 1175 | | | | | 1180 | | | | | |

| ctg | ggg | aag | aag | tac | caa | att | ttc | att | cca | atg | gtg | aat | aaa | gtt | 3612 |
|---|---|---|---|---|---|---|---|---|---|---|---|---|---|---|---|
| Leu | Gly | Lys | Lys | Tyr | Gln | Ile | Phe | Ile | Pro | Met | Val | Asn | Lys | Val | |
| 1185 | | | | | 1190 | | | | | 1195 | | | | | |

| ctg | gtg | cga | cac | cga | atc | aat | cat | cag | cgc | tat | gat | gtg | ctc | atc | 3657 |
|---|---|---|---|---|---|---|---|---|---|---|---|---|---|---|---|
| Leu | Val | Arg | His | Arg | Ile | Asn | His | Gln | Arg | Tyr | Asp | Val | Leu | Ile | |
| 1200 | | | | | 1205 | | | | | 1210 | | | | | |

| tgc | aga | att | gtc | aag | gga | tac | aca | ctt | gct | gat | gaa | gag | gag | gat | 3702 |
|---|---|---|---|---|---|---|---|---|---|---|---|---|---|---|---|
| Cys | Arg | Ile | Val | Lys | Gly | Tyr | Thr | Leu | Ala | Asp | Glu | Glu | Glu | Asp | |
| 1215 | | | | | 1220 | | | | | 1225 | | | | | |

| cct | ttg | att | tac | cag | cat | cgg | atg | ctt | agg | agt | ggc | caa | ggg | gat | 3747 |
|---|---|---|---|---|---|---|---|---|---|---|---|---|---|---|---|
| Pro | Leu | Ile | Tyr | Gln | His | Arg | Met | Leu | Arg | Ser | Gly | Gln | Gly | Asp | |
| 1230 | | | | | 1235 | | | | | 1240 | | | | | |

| gca | ttg | gct | agt | gga | cca | gtg | gaa | aca | gga | ccc | atg | aag | aaa | ctg | 3792 |
|---|---|---|---|---|---|---|---|---|---|---|---|---|---|---|---|
| Ala | Leu | Ala | Ser | Gly | Pro | Val | Glu | Thr | Gly | Pro | Met | Lys | Lys | Leu | |
| 1245 | | | | | 1250 | | | | | 1255 | | | | | |

| cac | gtc | agc | acc | atc | aac | ctc | caa | aag | gcc | tgg | ggc | gct | gcc | agg | 3837 |
|---|---|---|---|---|---|---|---|---|---|---|---|---|---|---|---|
| His | Val | Ser | Thr | Ile | Asn | Leu | Gln | Lys | Ala | Trp | Gly | Ala | Ala | Arg | |
| 1260 | | | | | 1265 | | | | | 1270 | | | | | |

| agg | gtc | tcc | aaa | gat | gac | tgg | ctg | gaa | tgg | ctg | aga | cgg | ctg | agc | 3882 |
|---|---|---|---|---|---|---|---|---|---|---|---|---|---|---|---|
| Arg | Val | Ser | Lys | Asp | Asp | Trp | Leu | Glu | Trp | Leu | Arg | Arg | Leu | Ser | |
| 1275 | | | | | 1280 | | | | | 1285 | | | | | |

| ctg | gag | ctg | ctg | aag | gac | tca | tca | tcg | ccc | tcc | ctg | cgc | tcc | tgc | 3927 |
|---|---|---|---|---|---|---|---|---|---|---|---|---|---|---|---|
| Leu | Glu | Leu | Leu | Lys | Asp | Ser | Ser | Ser | Pro | Ser | Leu | Arg | Ser | Cys | |
| 1290 | | | | | 1295 | | | | | 1300 | | | | | |

| tgg | gcc | ctg | gca | cag | gcc | tac | aac | ccg | atg | gcc | agg | gat | ctc | ttc | 3972 |
|---|---|---|---|---|---|---|---|---|---|---|---|---|---|---|---|
| Trp | Ala | Leu | Ala | Gln | Ala | Tyr | Asn | Pro | Met | Ala | Arg | Asp | Leu | Phe | |
| 1305 | | | | | 1310 | | | | | 1315 | | | | | |

-continued

```
aat gct gca ttt gtg tcc tgc tgg tct gaa ctg aat gaa gat caa       4017
Asn Ala Ala Phe Val Ser Cys Trp Ser Glu Leu Asn Glu Asp Gln
1320            1325                1330 cag gat gag ctc atc aga agc atc gag ttg gcc ctc acc tca caa       4062
Gln Asp Glu Leu Ile Arg Ser Ile Glu Leu Ala Leu Thr Ser Gln
    1335                1340                1345 gac atc gct gaa gtc aca cag acc ctc tta aac ttg gct gaa ttc       4107
Asp Ile Ala Glu Val Thr Gln Thr Leu Leu Asn Leu Ala Glu Phe
1350                1355                1360 atg gaa cac agt gac aag ggc ccc ctg cca ctg aga gat gac aat       4152
Met Glu His Ser Asp Lys Gly Pro Leu Pro Leu Arg Asp Asp Asn
        1365                1370                1375 ggc att gtt ctg ctg ggt gag aga gct gcc aag tgc cga gca tat       4197
Gly Ile Val Leu Leu Gly Glu Arg Ala Ala Lys Cys Arg Ala Tyr
1380                1385                1390 gcc aaa gca cta cac tac aaa gaa ctg gag ttc cag aaa ggc ccc       4242
Ala Lys Ala Leu His Tyr Lys Glu Leu Glu Phe Gln Lys Gly Pro
    1395                1400                1405 acc cct gcc att cta gaa tct ctc atc agc att aat aat aag cta       4287
Thr Pro Ala Ile Leu Glu Ser Leu Ile Ser Ile Asn Asn Lys Leu
1410                1415                1420 cag cag ccg gag gca gcg gcc gga gtg tta gaa tat gcc atg aaa       4332
Gln Gln Pro Glu Ala Ala Ala Gly Val Leu Glu Tyr Ala Met Lys
        1425                1430                1435 cac ttt gga gag ctg gag atc cag gct acc tgg tat gag aaa ctg       4377
His Phe Gly Glu Leu Glu Ile Gln Ala Thr Trp Tyr Glu Lys Leu
1440                1445                1450 cac gag tgg gag gat gcc ctt gtg gcc tat gac aag aaa atg gac       4422
His Glu Trp Glu Asp Ala Leu Val Ala Tyr Asp Lys Lys Met Asp
    1455                1460                1465 acc aac aag gac gac cca gag ctg atg ctg ggc cgc atg cgc tgc       4467
Thr Asn Lys Asp Asp Pro Glu Leu Met Leu Gly Arg Met Arg Cys
1470                1475                1480 ctc gag gcc ttg ggg gaa tgg ggt caa ctc cac cag cag tgc tgt       4512
Leu Glu Ala Leu Gly Glu Trp Gly Gln Leu His Gln Gln Cys Cys
        1485                1490                1495 gaa aag tgg acc ctg gtt aat gat gag acc caa gcc aag atg gcc       4557
Glu Lys Trp Thr Leu Val Asn Asp Glu Thr Gln Ala Lys Met Ala
1500                1505                1510 cgg atg gct gct gca gct gca tgg ggt tta ggt cag tgg gac agc       4602
Arg Met Ala Ala Ala Ala Ala Trp Gly Leu Gly Gln Trp Asp Ser
    1515                1520                1525 atg gaa gaa tac acc tgt atg atc cct cgg gac acc cat gat ggg       4647
Met Glu Glu Tyr Thr Cys Met Ile Pro Arg Asp Thr His Asp Gly
1530                1535                1540 gca ttt tat aga gct gtg ctg gca ctg cat cag gac ctc ttc tcc       4692
Ala Phe Tyr Arg Ala Val Leu Ala Leu His Gln Asp Leu Phe Ser
        1545                1550                1555 ttg gca caa cag tgc att gac aag gcc agg gac ctg ctg gat gct       4737
Leu Ala Gln Gln Cys Ile Asp Lys Ala Arg Asp Leu Leu Asp Ala
1560                1565                1570 gaa tta act gcg atg gca gga gag agt tac agt cgg gca tat ggg       4782
Glu Leu Thr Ala Met Ala Gly Glu Ser Tyr Ser Arg Ala Tyr Gly
    1575                1580                1585 gcc atg gtt tct tgc cac atg ctg tcc gag ctg gag gag gtt atc       4827
Ala Met Val Ser Cys His Met Leu Ser Glu Leu Glu Glu Val Ile
1590                1595                1600 cag tac aaa ctt gtc ccc gag cga cga gag atc atc cgc cag atc       4872
Gln Tyr Lys Leu Val Pro Glu Arg Arg Glu Ile Ile Arg Gln Ile
```

|     |     |     |     |     |     |     |     |     |     |      |
|-----|-----|-----|-----|-----|-----|-----|-----|-----|-----|------|
|     |     | 1605 |     |     | 1610 |     |     | 1615 |     |      |
| tgg | tgg | gag | aga | ctg | cag | ggc | tgc | cag | cgt | atc gta gag gac tgg | 4917 |
| Trp | Trp | Glu | Arg | Leu | Gln | Gly | Cys | Gln | Arg | Ile Val Glu Asp Trp |      |
|     | 1620 |     |     |     | 1625 |     |     |     | 1630 |      |
| cag | aaa | atc | ctt | atg | gtg | cgg | tcc | ctt | gtg | gtc agc cct cat gaa | 4962 |
| Gln | Lys | Ile | Leu | Met | Val | Arg | Ser | Leu | Val | Val Ser Pro His Glu |      |
|     | 1635 |     |     |     | 1640 |     |     |     | 1645 |      |
| gac | atg | aga | acc | tgg | ctc | aag | tat | gca | agc | ctg tgc ggc aag agt | 5007 |
| Asp | Met | Arg | Thr | Trp | Leu | Lys | Tyr | Ala | Ser | Leu Cys Gly Lys Ser |      |
|     | 1650 |     |     |     | 1655 |     |     |     | 1660 |      |
| ggc | agg | ctg | gct | ctt | gct | cat | aaa | act | tta | gtg ttg ctc ctg gga | 5052 |
| Gly | Arg | Leu | Ala | Leu | Ala | His | Lys | Thr | Leu | Val Leu Leu Leu Gly |      |
|     | 1665 |     |     |     | 1670 |     |     |     | 1675 |      |
| gtt | gat | ccg | tct | cgg | caa | ctt | gac | cat | cct | ctg cca aca gtt cac | 5097 |
| Val | Asp | Pro | Ser | Arg | Gln | Leu | Asp | His | Pro | Leu Pro Thr Val His |      |
|     | 1680 |     |     |     | 1685 |     |     |     | 1690 |      |
| cct | cag | gtg | acc | tat | gcc | tac | atg | aaa | aac | atg tgg aag agt gcc | 5142 |
| Pro | Gln | Val | Thr | Tyr | Ala | Tyr | Met | Lys | Asn | Met Trp Lys Ser Ala |      |
|     | 1695 |     |     |     | 1700 |     |     |     | 1705 |      |
| cgc | aag | atc | gat | gcc | ttc | cag | cac | atg | cag | cat ttt gtc cag acc | 5187 |
| Arg | Lys | Ile | Asp | Ala | Phe | Gln | His | Met | Gln | His Phe Val Gln Thr |      |
|     | 1710 |     |     |     | 1715 |     |     |     | 1720 |      |
| atg | cag | caa | cag | gcc | cag | cat | gcc | atc | gct | act gag gac cag cag | 5232 |
| Met | Gln | Gln | Gln | Ala | Gln | His | Ala | Ile | Ala | Thr Glu Asp Gln Gln |      |
|     | 1725 |     |     |     | 1730 |     |     |     | 1735 |      |
| cat | aag | cag | gaa | ctg | cac | aag | ctc | atg | gcc | cga tgc ttc ctg aaa | 5277 |
| His | Lys | Gln | Glu | Leu | His | Lys | Leu | Met | Ala | Arg Cys Phe Leu Lys |      |
|     | 1740 |     |     |     | 1745 |     |     |     | 1750 |      |
| ctt | gga | gag | tgg | cag | ctg | aat | cta | cag | ggc | atc aat gag agc aca | 5322 |
| Leu | Gly | Glu | Trp | Gln | Leu | Asn | Leu | Gln | Gly | Ile Asn Glu Ser Thr |      |
|     | 1755 |     |     |     | 1760 |     |     |     | 1765 |      |
| atc | ccc | aaa | gtg | ctg | cag | tac | tac | agc | gcc | gcc aca gag cac gac | 5367 |
| Ile | Pro | Lys | Val | Leu | Gln | Tyr | Tyr | Ser | Ala | Ala Thr Glu His Asp |      |
|     | 1770 |     |     |     | 1775 |     |     |     | 1780 |      |
| cgc | agc | tgg | tac | aag | gcc | tgg | cat | gcg | tgg | gca gtg atg aac ttc | 5412 |
| Arg | Ser | Trp | Tyr | Lys | Ala | Trp | His | Ala | Trp | Ala Val Met Asn Phe |      |
|     | 1785 |     |     |     | 1790 |     |     |     | 1795 |      |
| gaa | gct | gtg | cta | cac | tac | aaa | cat | cag | aac | caa gcc cgc gat gag | 5457 |
| Glu | Ala | Val | Leu | His | Tyr | Lys | His | Gln | Asn | Gln Ala Arg Asp Glu |      |
|     | 1800 |     |     |     | 1805 |     |     |     | 1810 |      |
| aag | aag | aaa | ctg | cgt | cat | gcc | agc | ggg | gcc | aac atc acc aac gcc | 5502 |
| Lys | Lys | Lys | Leu | Arg | His | Ala | Ser | Gly | Ala | Asn Ile Thr Asn Ala |      |
|     | 1815 |     |     |     | 1820 |     |     |     | 1825 |      |
| acc | act | gcc | gcc | acc | acg | gcc | gcc | act | gcc | acc acc act gcc agc | 5547 |
| Thr | Thr | Ala | Ala | Thr | Thr | Ala | Ala | Thr | Ala | Thr Thr Thr Ala Ser |      |
|     | 1830 |     |     |     | 1835 |     |     |     | 1840 |      |
| acc | gag | ggc | agc | aac | agt | gag | agt | gag | gcc | gag agc acc gag aac | 5592 |
| Thr | Glu | Gly | Ser | Asn | Ser | Glu | Ser | Glu | Ala | Glu Ser Thr Glu Asn |      |
|     | 1845 |     |     |     | 1850 |     |     |     | 1855 |      |
| agc | ccc | acc | cca | tcg | ccg | ctg | cag | aag | aag | gtc act gag gat ctg | 5637 |
| Ser | Pro | Thr | Pro | Ser | Pro | Leu | Gln | Lys | Lys | Val Thr Glu Asp Leu |      |
|     | 1860 |     |     |     | 1865 |     |     |     | 1870 |      |
| tcc | aaa | acc | ctc | ctg | atg | tac | acg | gtg | cct | gcc gtc cag ggc ttc | 5682 |
| Ser | Lys | Thr | Leu | Leu | Met | Tyr | Thr | Val | Pro | Ala Val Gln Gly Phe |      |
|     | 1875 |     |     |     | 1880 |     |     |     | 1885 |      |
| ttc | cgt | tcc | atc | tcc | ttg | tca | cga | ggc | aac | aac ctc cag gat aca | 5727 |
| Phe | Arg | Ser | Ile | Ser | Leu | Ser | Arg | Gly | Asn | Asn Leu Gln Asp Thr |      |
|     | 1890 |     |     |     | 1895 |     |     |     | 1900 |      |
| ctc | aga | gtt | ctc | acc | tta | tgg | ttt | gat | tat | ggt cac tgg cca gat | 5772 |

```
                Leu Arg Val Leu Thr Leu Trp Phe Asp Tyr Gly His Trp Pro Asp
                    1905            1910            1915 gtc aat gag gcc tta gtg gag ggg gtg aaa gcc atc cag att gat         5817
Val Asn Glu Ala Leu Val Glu Gly Val Lys Ala Ile Gln Ile Asp
    1920            1925            1930 acc tgg cta cag gtt ata cct cag ctc att gca aga att gat acg         5862
Thr Trp Leu Gln Val Ile Pro Gln Leu Ile Ala Arg Ile Asp Thr
1935            1940            1945 ccc aga ccc ttg gtg gga cgt ctc att cac cag ctt ctc aca gac         5907
Pro Arg Pro Leu Val Gly Arg Leu Ile His Gln Leu Leu Thr Asp
    1950            1955            1960 att ggt cgg tac cac ccc cag gcc ctc atc tac cca ctg aca gtg         5952
Ile Gly Arg Tyr His Pro Gln Ala Leu Ile Tyr Pro Leu Thr Val
    1965            1970            1975 gct tct aag tct acc acg aca gcc cgg cac aat gca gcc aac aag         5997
Ala Ser Lys Ser Thr Thr Thr Ala Arg His Asn Ala Ala Asn Lys
1980            1985            1990 att ctg aag aac atg tgt gag cac agc aac acc ctg gtc cag cag         6042
Ile Leu Lys Asn Met Cys Glu His Ser Asn Thr Leu Val Gln Gln
    1995            2000            2005 gcc atg atg gtg agc gag gag ctg atc cga gtg gcc atc ctc tgg         6087
Ala Met Met Val Ser Glu Glu Leu Ile Arg Val Ala Ile Leu Trp
2010            2015            2020 cat gag atg tgg cat gaa ggc ctg gaa gag gca tct cgt ttg tac         6132
His Glu Met Trp His Glu Gly Leu Glu Glu Ala Ser Arg Leu Tyr
    2025            2030            2035 ttt ggg gaa agg aac gtg aaa ggc atg ttt gag gtg ctg gag ccc         6177
Phe Gly Glu Arg Asn Val Lys Gly Met Phe Glu Val Leu Glu Pro
2040            2045            2050 ttg cat gct atg atg gaa cgg ggc ccc cag act ctg aag gaa aca         6222
Leu His Ala Met Met Glu Arg Gly Pro Gln Thr Leu Lys Glu Thr
    2055            2060            2065 tcc ttt aat cag gcc tat ggt cga gat tta atg gag gcc caa gag         6267
Ser Phe Asn Gln Ala Tyr Gly Arg Asp Leu Met Glu Ala Gln Glu
2070            2075            2080 tgg tgc agg aag tac atg aaa tca ggg aat gtc aag gac ctc acc         6312
Trp Cys Arg Lys Tyr Met Lys Ser Gly Asn Val Lys Asp Leu Thr
    2085            2090            2095 caa gcc tgg gac ctc tat tat cat gtg ttc cga cga atc tca aag         6357
Gln Ala Trp Asp Leu Tyr Tyr His Val Phe Arg Arg Ile Ser Lys
2100            2105            2110 cag ctg cct cag ctc aca tcc tta gag ctg caa tat gtt tcc cca         6402
Gln Leu Pro Gln Leu Thr Ser Leu Glu Leu Gln Tyr Val Ser Pro
    2115            2120            2125 aaa ctt ctg atg tgc cgg gac ctt gaa ttg gct gtg cca gga aca         6447
Lys Leu Leu Met Cys Arg Asp Leu Glu Leu Ala Val Pro Gly Thr
2130            2135            2140 tat gac ccc aac cag cca atc att cgc att cag tcc ata gca ccg         6492
Tyr Asp Pro Asn Gln Pro Ile Ile Arg Ile Gln Ser Ile Ala Pro
    2145            2150            2155 tct ttg caa gtc atc aca tcc aag cag agg ccc cgg aaa ttg aca         6537
Ser Leu Gln Val Ile Thr Ser Lys Gln Arg Pro Arg Lys Leu Thr
2160            2165            2170 ctt atg ggc agc aac gga cat gag ttt gtt ttc ctt cta aaa ggc         6582
Leu Met Gly Ser Asn Gly His Glu Phe Val Phe Leu Leu Lys Gly
    2175            2180            2185 cat gaa gat ctg cgc cag gat gag cgt gtg atg cag ctc ttc ggc         6627
His Glu Asp Leu Arg Gln Asp Glu Arg Val Met Gln Leu Phe Gly
2190            2195            2200
```

```
ctg gtt aac acc ctc ctg gcc aat gac cca aca tct ctt cgg aaa      6672
Leu Val Asn Thr Leu Leu Ala Asn Asp Pro Thr Ser Leu Arg Lys
    2205                2210                2215 aac ctc agc atc cag aga tac gct gtc atc cct tta tcg acc aac      6717
Asn Leu Ser Ile Gln Arg Tyr Ala Val Ile Pro Leu Ser Thr Asn
2220                2225                2230 tcg ggc ctc att ggc tgg gtt ccc cac tgt gac aca ctg cac gcc      6762
Ser Gly Leu Ile Gly Trp Val Pro His Cys Asp Thr Leu His Ala
        2235                2240                2245 ctc atc cgg gac tac agg gag aag aag aag atc ctt ctc aac atc      6807
Leu Ile Arg Asp Tyr Arg Glu Lys Lys Lys Ile Leu Leu Asn Ile
2250                2255                2260 gag cat cgc atc atg ttg cgg atg gct ccg gac tat gac cac ttg      6852
Glu His Arg Ile Met Leu Arg Met Ala Pro Asp Tyr Asp His Leu
    2265                2270                2275 act ctg atg cag aag gtg gag gtg ttt gag cat gcc gtc aat aat      6897
Thr Leu Met Gln Lys Val Glu Val Phe Glu His Ala Val Asn Asn
        2280                2285                2290 aca gct ggg gac gac ctg gcc aag ctg cta tgg ctg aaa agc ccc      6942
Thr Ala Gly Asp Asp Leu Ala Lys Leu Leu Trp Leu Lys Ser Pro
2295                2300                2305 agc tcc gag gtg tgg ttt gac cga aga acc aat tat acc cgt tct      6987
Ser Ser Glu Val Trp Phe Asp Arg Arg Thr Asn Tyr Thr Arg Ser
    2310                2315                2320 tta gcg gtc atg tca atg gtt ggg tat att tta ggc ctg gga gat      7032
Leu Ala Val Met Ser Met Val Gly Tyr Ile Leu Gly Leu Gly Asp
        2325                2330                2335 aga cac cca tcc aac ctg atg ctg gac cgt ctg agt ggg aag atc      7077
Arg His Pro Ser Asn Leu Met Leu Asp Arg Leu Ser Gly Lys Ile
2340                2345                2350 ctg cac att gac ttt ggg gac tgc ttt gag gtt gct atg acc cga      7122
Leu His Ile Asp Phe Gly Asp Cys Phe Glu Val Ala Met Thr Arg
    2355                2360                2365 gag aag ttt cca gag aag att cca ttt aga cta aca aga atg ttg      7167
Glu Lys Phe Pro Glu Lys Ile Pro Phe Arg Leu Thr Arg Met Leu
        2370                2375                2380 acc aat gct atg gag gtt aca ggc ctg gat ggc aac tac aga atc      7212
Thr Asn Ala Met Glu Val Thr Gly Leu Asp Gly Asn Tyr Arg Ile
2385                2390                2395 aca tgc cac aca gtg atg gag gtg ctg cga gag cac aag gac agt      7257
Thr Cys His Thr Val Met Glu Val Leu Arg Glu His Lys Asp Ser
    2400                2405                2410 gtc atg gcc gtg ctg gaa gcc ttt gtc tat gac ccc ttg ctg aac      7302
Val Met Ala Val Leu Glu Ala Phe Val Tyr Asp Pro Leu Leu Asn
        2415                2420                2425 tgg agg ctg atg gac aca aat acc aaa ggc aac aag cga tcc cga      7347
Trp Arg Leu Met Asp Thr Asn Thr Lys Gly Asn Lys Arg Ser Arg
2430                2435                2440 acg agg acg gat tcc tac tct gct ggc cag tca gtc gaa att ttg      7392
Thr Arg Thr Asp Ser Tyr Ser Ala Gly Gln Ser Val Glu Ile Leu
    2445                2450                2455 gac ggt gtg gaa ctt gga gag cca gcc cat aag aaa acg ggg acc      7437
Asp Gly Val Glu Leu Gly Glu Pro Ala His Lys Lys Thr Gly Thr
        2460                2465                2470 aca gtg cca gaa tct att cat tct ttc att gga gac ggt ttg gtg      7482
Thr Val Pro Glu Ser Ile His Ser Phe Ile Gly Asp Gly Leu Val
2475                2480                2485 aaa cca gag gcc cta aat aag aaa gct atc cag att att aac agg      7527
Lys Pro Glu Ala Leu Asn Lys Lys Ala Ile Gln Ile Ile Asn Arg
    2490                2495                2500
```

```
gtt cga gat aag ctc act ggt cgg gac ttc tct cat gat gac act    7572
Val Arg Asp Lys Leu Thr Gly Arg Asp Phe Ser His Asp Asp Thr
    2505            2510                2515 ttg gat gtt cca acg caa gtt gag ctg ctc atc aaa caa gcg aca    7617
Leu Asp Val Pro Thr Gln Val Glu Leu Leu Ile Lys Gln Ala Thr
    2520            2525                2530 tcc cat gaa aac ctc tgc cag tgc tat att ggc tgg tgc cct ttc    7662
Ser His Glu Asn Leu Cys Gln Cys Tyr Ile Gly Trp Cys Pro Phe
    2535            2540                2545 tgg taa ctggaggccc agatgtgccc atcacgtttt ttctgaggct tttgtacttt    7718
Trp agtaaatgct tccactaaac tgaaaccatg gtgagaaagt ttgactttgt taaatatttt    7778
gaaatgtaaa tgaaagaac tactgtatat taaaagttgg tttgaaccaa ctttctagct    7838
gctgttgaag aatatattgt cagaaacaca aggcttgatt tggttcccag gacagtgaaa    7898
catagtaata ccacgtaaat caagccattc attttgggga acagaagatc cataacttta    7958
gaaatacggg ttttgactta actcacaaga gaactcatca taagtacttg ctgatggaag    8018
aatgacctag ttgctcctct caacatgggt acagcaaact cagcacagcc aagaagcctc    8078
aggtcgtgga gaacatggat taggatccta gactgtaaag acacagaaga tgctgacctc    8138 accctgcca cctatcc    8155

<210> SEQ ID NO 6
<211> LENGTH: 2549
<212> TYPE: PRT
<213> ORGANISM: Homo sapiens

<400> SEQUENCE: 6

Met Leu Gly Thr Gly Pro Ala Ala Thr Thr Ala Ala Thr Thr Ser
1               5                   10                  15

Ser Asn Val Ser Val Leu Gln Gln Phe Ala Ser Gly Leu Lys Ser Arg
                20                  25                  30

Asn Glu Glu Thr Arg Ala Lys Ala Ala Lys Glu Leu Gln His Tyr Val
            35                  40                  45

Thr Met Glu Leu Arg Glu Met Ser Gln Glu Glu Ser Thr Arg Phe Tyr
        50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205
```

```
Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
                340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
                420                 425                 430

Ala Phe Gln Ala Leu Gly Leu Leu Ser Val Ala Val Arg Ser Glu Phe
            435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
            515                 520                 525

Pro Gln Leu Lys Lys Asp Ile Gln Asp Gly Leu Leu Lys Met Leu Ser
530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
                580                 585                 590

Glu Phe Glu Gly His Ser Leu Thr Gln Phe Val Arg His Cys Ala Asp
            595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
```

```
          625                 630                 635                 640
Ala His Val Val Ser Gln Thr Ala Val Gln Val Val Ala Asp Val Leu
                    645                 650                 655

Ser Lys Leu Leu Val Val Gly Ile Thr Asp Pro Asp Pro Asp Ile Arg
                    660                 665                 670

Tyr Cys Val Leu Ala Ser Leu Asp Glu Arg Phe Asp Ala His Leu Ala
                    675                 680                 685

Gln Ala Glu Asn Leu Gln Ala Leu Phe Val Ala Leu Asn Asp Gln Val
                    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                    725                 730                 735

Ile Leu Thr Glu Leu Glu His Ser Gly Ile Gly Arg Ile Lys Glu Gln
                    740                 745                 750

Ser Ala Arg Met Leu Gly His Leu Val Ser Asn Ala Pro Arg Leu Ile
                    755                 760                 765

Arg Pro Tyr Met Glu Pro Ile Leu Lys Ala Leu Ile Leu Lys Leu Lys
                    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                    805                 810                 815

Val Asp Glu Leu Phe Ile Ile Met Asp Met Leu Gln Asp Ser Ser
                    820                 825                 830

Leu Leu Ala Lys Arg Gln Val Ala Leu Trp Thr Leu Gly Gln Leu Val
                    835                 840                 845

Ala Ser Thr Gly Tyr Val Val Glu Pro Tyr Arg Lys Tyr Pro Thr Leu
                    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                    885                 890                 895

Tyr Lys His Lys Val Asn Ile Gly Met Ile Asp Gln Ser Arg Asp Ala
                    900                 905                 910

Ser Ala Val Ser Leu Ser Glu Ser Lys Ser Ser Gln Asp Ser Ser Asp
                    915                 920                 925

Tyr Ser Thr Ser Glu Met Leu Val Asn Met Gly Asn Leu Pro Leu Asp
930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
                    965                 970                 975

Phe Ile Phe Lys Ser Leu Gly Leu Lys Cys Val Gln Phe Leu Pro Gln
                    980                 985                 990

Val Met Pro Thr Phe Leu Asn Val  Ile Arg Val Cys Asp  Gly Ala Ile
          995                  1000                1005

Arg Glu  Phe Leu Phe Gln Gln  Leu Gly Met Leu Val  Ser Phe Val
    1010                 1015                1020

Lys Ser  His Ile Arg Pro Tyr  Met Asp Glu Ile Val  Thr Leu Met
    1025                 1030                1035

Arg Glu  Phe Trp Val Met Asn  Thr Ser Ile Gln Ser  Thr Ile Ile
    1040                 1045                1050
```

-continued

Leu Leu Ile Glu Gln Ile Val Val Ala Leu Gly Gly Glu Phe Lys
1055                1060                1065

Leu Tyr Leu Pro Gln Leu Ile Pro His Met Leu Arg Val Phe Met
1070                1075                1080

His Asp Asn Ser Pro Gly Arg Ile Val Ser Ile Lys Leu Leu Ala
1085                1090                1095

Ala Ile Gln Leu Phe Gly Ala Asn Leu Asp Asp Tyr Leu His Leu
1100                1105                1110

Leu Leu Pro Pro Ile Val Lys Leu Phe Asp Ala Pro Glu Ala Pro
1115                1120                1125

Leu Pro Ser Arg Lys Ala Ala Leu Glu Thr Val Asp Arg Leu Thr
1130                1135                1140

Glu Ser Leu Asp Phe Thr Asp Tyr Ala Ser Arg Ile Ile His Pro
1145                1150                1155

Ile Val Arg Thr Leu Asp Gln Ser Pro Glu Leu Arg Ser Thr Ala
1160                1165                1170

Met Asp Thr Leu Ser Ser Leu Val Phe Gln Leu Gly Lys Lys Tyr
1175                1180                1185

Gln Ile Phe Ile Pro Met Val Asn Lys Val Leu Val Arg His Arg
1190                1195                1200

Ile Asn His Gln Arg Tyr Asp Val Leu Ile Cys Arg Ile Val Lys
1205                1210                1215

Gly Tyr Thr Leu Ala Asp Glu Glu Asp Pro Leu Ile Tyr Gln
1220                1225                1230

His Arg Met Leu Arg Ser Gly Gln Gly Asp Ala Leu Ala Ser Gly
1235                1240                1245

Pro Val Glu Thr Gly Pro Met Lys Lys Leu His Val Ser Thr Ile
1250                1255                1260

Asn Leu Gln Lys Ala Trp Gly Ala Ala Arg Arg Val Ser Lys Asp
1265                1270                1275

Asp Trp Leu Glu Trp Leu Arg Arg Leu Ser Leu Glu Leu Leu Lys
1280                1285                1290

Asp Ser Ser Ser Pro Ser Leu Arg Ser Cys Trp Ala Leu Ala Gln
1295                1300                1305

Ala Tyr Asn Pro Met Ala Arg Asp Leu Phe Asn Ala Ala Phe Val
1310                1315                1320

Ser Cys Trp Ser Glu Leu Asn Glu Asp Gln Gln Asp Glu Leu Ile
1325                1330                1335

Arg Ser Ile Glu Leu Ala Leu Thr Ser Gln Asp Ile Ala Glu Val
1340                1345                1350

Thr Gln Thr Leu Leu Asn Leu Ala Glu Phe Met Glu His Ser Asp
1355                1360                1365

Lys Gly Pro Leu Pro Leu Arg Asp Asp Asn Gly Ile Val Leu Leu
1370                1375                1380

Gly Glu Arg Ala Ala Lys Cys Arg Ala Tyr Ala Lys Ala Leu His
1385                1390                1395

Tyr Lys Glu Leu Glu Phe Gln Lys Gly Pro Thr Pro Ala Ile Leu
1400                1405                1410

Glu Ser Leu Ile Ser Ile Asn Asn Lys Leu Gln Gln Pro Glu Ala
1415                1420                1425

Ala Ala Gly Val Leu Glu Tyr Ala Met Lys His Phe Gly Glu Leu
1430                1435                1440

-continued

```
Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Asp Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830
```

```
Thr Ala Ala Thr Ala Thr Thr Thr Ala Ser Thr Glu Gly Ser Asn
1835              1840              1845

Ser Glu Ser Glu Ala Glu Ser Thr Glu Asn Ser Pro Thr Pro Ser
1850              1855              1860

Pro Leu Gln Lys Lys Val Thr Glu Asp Leu Ser Lys Thr Leu Leu
1865              1870              1875

Met Tyr Thr Val Pro Ala Val Gln Gly Phe Phe Arg Ser Ile Ser
1880              1885              1890

Leu Ser Arg Gly Asn Asn Leu Gln Asp Thr Leu Arg Val Leu Thr
1895              1900              1905

Leu Trp Phe Asp Tyr Gly His Trp Pro Asp Val Asn Glu Ala Leu
1910              1915              1920

Val Glu Gly Val Lys Ala Ile Gln Ile Asp Thr Trp Leu Gln Val
1925              1930              1935

Ile Pro Gln Leu Ile Ala Arg Ile Asp Thr Pro Arg Pro Leu Val
1940              1945              1950

Gly Arg Leu Ile His Gln Leu Leu Thr Asp Ile Gly Arg Tyr His
1955              1960              1965

Pro Gln Ala Leu Ile Tyr Pro Leu Thr Val Ala Ser Lys Ser Thr
1970              1975              1980

Thr Thr Ala Arg His Asn Ala Ala Asn Lys Ile Leu Lys Asn Met
1985              1990              1995

Cys Glu His Ser Asn Thr Leu Val Gln Gln Ala Met Met Val Ser
2000              2005              2010

Glu Glu Leu Ile Arg Val Ala Ile Leu Trp His Glu Met Trp His
2015              2020              2025

Glu Gly Leu Glu Glu Ala Ser Arg Leu Tyr Phe Gly Glu Arg Asn
2030              2035              2040

Val Lys Gly Met Phe Glu Val Leu Glu Pro Leu His Ala Met Met
2045              2050              2055

Glu Arg Gly Pro Gln Thr Leu Lys Glu Thr Ser Phe Asn Gln Ala
2060              2065              2070

Tyr Gly Arg Asp Leu Met Glu Ala Gln Glu Trp Cys Arg Lys Tyr
2075              2080              2085

Met Lys Ser Gly Asn Val Lys Asp Leu Thr Gln Ala Trp Asp Leu
2090              2095              2100

Tyr Tyr His Val Phe Arg Arg Ile Ser Lys Gln Leu Pro Gln Leu
2105              2110              2115

Thr Ser Leu Glu Leu Gln Tyr Val Ser Pro Lys Leu Leu Met Cys
2120              2125              2130

Arg Asp Leu Glu Leu Ala Val Pro Gly Thr Tyr Asp Pro Asn Gln
2135              2140              2145

Pro Ile Ile Arg Ile Gln Ser Ile Ala Pro Ser Leu Gln Val Ile
2150              2155              2160

Thr Ser Lys Gln Arg Pro Arg Lys Leu Thr Leu Met Gly Ser Asn
2165              2170              2175

Gly His Glu Phe Val Phe Leu Leu Lys Gly His Glu Asp Leu Arg
2180              2185              2190

Gln Asp Glu Arg Val Met Gln Leu Phe Gly Leu Val Asn Thr Leu
2195              2200              2205

Leu Ala Asn Asp Pro Thr Ser Leu Arg Lys Asn Leu Ser Ile Gln
2210              2215              2220
```

```
Arg Tyr Ala Val Ile Pro Leu Ser Thr Asn Ser Gly Leu Ile Gly
    2225                2230                2235

Trp Val Pro His Cys Asp Thr Leu His Ala Leu Ile Arg Asp Tyr
    2240                2245                2250

Arg Glu Lys Lys Lys Ile Leu Leu Asn Ile Glu His Arg Ile Met
    2255                2260                2265

Leu Arg Met Ala Pro Asp Tyr Asp His Leu Thr Leu Met Gln Lys
    2270                2275                2280

Val Glu Val Phe Glu His Ala Val Asn Asn Thr Ala Gly Asp Asp
    2285                2290                2295

Leu Ala Lys Leu Leu Trp Leu Lys Ser Pro Ser Ser Glu Val Trp
    2300                2305                2310

Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Ile Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 7
<211> LENGTH: 3376
<212> TYPE: DNA
<213> ORGANISM: Lymphocytic choriomeningitis virus
<220> FEATURE:
<221> NAME/KEY: CDS
<222> LOCATION: (78)..(1574)
```

<400> SEQUENCE: 7

```
cgcaccgggg atcctaggct ttttggattg cgctttcctc tagatcaact gggtgtcagg        60
ccctatccta cagaagg atg ggt cag att gtg aca atg ttt gag gct ctg          110
                Met Gly Gln Ile Val Thr Met Phe Glu Ala Leu
                 1               5                  10 cct cac atc atc gat gag gtg atc aac att gtc att att gtg ctt atc        158
Pro His Ile Ile Asp Glu Val Ile Asn Ile Val Ile Ile Val Leu Ile
            15                  20                  25 gtg atc acg ggt atc aag gct gtc tac aat ttt gcc acc tgt ggg ata        206
Val Ile Thr Gly Ile Lys Ala Val Tyr Asn Phe Ala Thr Cys Gly Ile
            30                  35                  40 ttc gca ttg atc agt ttc cta ctt ctg gct ggc agg tcc tgt ggc atg        254
Phe Ala Leu Ile Ser Phe Leu Leu Leu Ala Gly Arg Ser Cys Gly Met
        45                  50                  55 tac ggt ctt aag gga ccc gac att tac aaa gga gtt tac caa ttt aag        302
Tyr Gly Leu Lys Gly Pro Asp Ile Tyr Lys Gly Val Tyr Gln Phe Lys
 60                  65                  70                  75 tca gtg gag ttt gat atg tca cat ctg aac ctg acc atg ccc aac gca        350
Ser Val Glu Phe Asp Met Ser His Leu Asn Leu Thr Met Pro Asn Ala
                80                  85                  90 tgt tca gcc aac aac tcc cac cat tac atc agt atg ggg act tct gga        398
Cys Ser Ala Asn Asn Ser His His Tyr Ile Ser Met Gly Thr Ser Gly
                95                 100                 105 cta gaa ttg acc ttc acc aat gat tcc atc atc agt cac aac ttt tgc        446
Leu Glu Leu Thr Phe Thr Asn Asp Ser Ile Ile Ser His Asn Phe Cys
            110                 115                 120 aat ctg acc tct gcc ttc aac aaa aag acc ttt gac cac aca ctc atg        494
Asn Leu Thr Ser Ala Phe Asn Lys Lys Thr Phe Asp His Thr Leu Met
        125                 130                 135 agt ata gtt tcg agc cta cac ctc agt atc aga ggg aac tcc aac tat        542
Ser Ile Val Ser Ser Leu His Leu Ser Ile Arg Gly Asn Ser Asn Tyr
140                 145                 150                 155 aag gca gta tcc tgc gac ttc aac aat ggc ata acc atc caa tac aac        590
Lys Ala Val Ser Cys Asp Phe Asn Asn Gly Ile Thr Ile Gln Tyr Asn
                160                 165                 170 ttg aca ttc tca gat cga caa agt gct cag agc cag tgt aga acc ttc        638
Leu Thr Phe Ser Asp Arg Gln Ser Ala Gln Ser Gln Cys Arg Thr Phe
            175                 180                 185 aga ggt aga gtc cta gat atg ttt aga act gcc ttc ggg gga aaa tac        686
Arg Gly Arg Val Leu Asp Met Phe Arg Thr Ala Phe Gly Gly Lys Tyr
        190                 195                 200 atg agg agt ggc tgg ggc tgg aca ggc tca gat ggc aag acc acc tgg        734
Met Arg Ser Gly Trp Gly Trp Thr Gly Ser Asp Gly Lys Thr Thr Trp
205                 210                 215 tgt agc cag acg agt tac caa tac ctg att ata caa aat aga acc tgg        782
Cys Ser Gln Thr Ser Tyr Gln Tyr Leu Ile Ile Gln Asn Arg Thr Trp
220                 225                 230                 235 gaa aac cac tgc aca tat gca ggt cct ttt ggg atg tcc agg att ctc        830
Glu Asn His Cys Thr Tyr Ala Gly Pro Phe Gly Met Ser Arg Ile Leu
                240                 245                 250 ctt tcc caa gag aag act aag ttc ttc act agg aga cta gcg ggc aca        878
Leu Ser Gln Glu Lys Thr Lys Phe Phe Thr Arg Arg Leu Ala Gly Thr
            255                 260                 265 ttc acc tgg act ttg tca gac tct tca ggg gtg gag aat cca ggt ggt        926
Phe Thr Trp Thr Leu Ser Asp Ser Ser Gly Val Glu Asn Pro Gly Gly
        270                 275                 280 tat tgc ctg acc aaa tgg atg att ctt gct gca gag ctt aag tgt ttc        974
Tyr Cys Leu Thr Lys Trp Met Ile Leu Ala Ala Glu Leu Lys Cys Phe
285                 290                 295
```

-continued

| | |
|---|---|
| ggg aac aca gca gtt gcg aaa tgc aat gta aat cat gat gcc gaa ttc<br>Gly Asn Thr Ala Val Ala Lys Cys Asn Val Asn His Asp Ala Glu Phe<br>300                  305                  310                  315 | 1022 |
| tgt gac atg ctg cga cta att gac tac aac aag gct gct ttg agt aag<br>Cys Asp Met Leu Arg Leu Ile Asp Tyr Asn Lys Ala Ala Leu Ser Lys<br>320                  325                  330 | 1070 |
| ttc aaa gag gac gta gaa tct gcc ttg cac tta ttc aaa aca aca gtg<br>Phe Lys Glu Asp Val Glu Ser Ala Leu His Leu Phe Lys Thr Thr Val<br>335                  340                  345 | 1118 |
| aat tct ttg att tca gat caa cta ctg atg agg aac cac ttg aga gat<br>Asn Ser Leu Ile Ser Asp Gln Leu Leu Met Arg Asn His Leu Arg Asp<br>350                  355                  360 | 1166 |
| ctg atg ggg gtg cca tat tgc aat tac tca aag ttt tgg tac cta gaa<br>Leu Met Gly Val Pro Tyr Cys Asn Tyr Ser Lys Phe Trp Tyr Leu Glu<br>365                  370                  375 | 1214 |
| cat gca aag acc ggc gaa act agt gtc ccc aag tgc tgg ctt gtc acc<br>His Ala Lys Thr Gly Glu Thr Ser Val Pro Lys Cys Trp Leu Val Thr<br>380                  385                  390                  395 | 1262 |
| aat ggt tct tac tta aat gag acc cac ttc agt gat caa atc gaa cag<br>Asn Gly Ser Tyr Leu Asn Glu Thr His Phe Ser Asp Gln Ile Glu Gln<br>400                  405                  410 | 1310 |
| gaa gcc gat aac atg att aca gag atg ttg agg aag gat tac ata aag<br>Glu Ala Asp Asn Met Ile Thr Glu Met Leu Arg Lys Asp Tyr Ile Lys<br>415                  420                  425 | 1358 |
| agg cag ggg agt acc ccc cta gca ttg atg gac ctt ctg atg ttt tcc<br>Arg Gln Gly Ser Thr Pro Leu Ala Leu Met Asp Leu Leu Met Phe Ser<br>430                  435                  440 | 1406 |
| aca tct gca tat cta gtc agc atc ttc ctg cac ctt gtc aaa ata cca<br>Thr Ser Ala Tyr Leu Val Ser Ile Phe Leu His Leu Val Lys Ile Pro<br>445                  450                  455 | 1454 |
| aca cac agg cac ata aaa ggt ggc tca tgt cca aag cca cac cga tta<br>Thr His Arg His Ile Lys Gly Gly Ser Cys Pro Lys Pro His Arg Leu<br>460                  465                  470                  475 | 1502 |
| acc aac aaa gga att tgt agt tgt ggt gca ttt aag gtg cct ggt gta<br>Thr Asn Lys Gly Ile Cys Ser Cys Gly Ala Phe Lys Val Pro Gly Val<br>480                  485                  490 | 1550 |
| aaa acc gtc tgg aaa aga cgc tga agaacagcgc ctccctgact ctccacctcg<br>Lys Thr Val Trp Lys Arg Arg<br>495 | 1604 |
| aaagaggtgg agagtcaggg aggcccagag ggtcttagag tgtcacaaca tttgggcctc | 1664 |
| taaaaattag gtcatgtggc agaatgttgt gaacagtttt cagatctggg agccttgctt | 1724 |
| tggaggcgct ttcaaaaatg atgcagtcca tgagtgcaca gtgcgggtg atctcttttct | 1784 |
| tcttttttgtc ccttactatt ccagtatgca tcttacacaa ccagccatat ttgtcccaca | 1844 |
| ctttgtcttc atactccctc gaagcttccc tggtcatttc aacatcgata agcttaatgt | 1904 |
| ccttcctatt ctgtgagtcc agaagctttc tgatgtcatc ggagccttga cagcttagaa | 1964 |
| ccatcccctg cggaagagca cctataactg acgaggtcaa cccgggttgc gcattgaaga | 2024 |
| ggtcggcaag atccatgccg tgtgagtact tggaatcttg cttgaattgt ttttgatcaa | 2084 |
| cgggttccct gtaaaagtgt atgaactgcc cgttctgtgg ttggaaaatt gctatttcca | 2144 |
| ctggatcatt aaatctaccc tcaatgtcaa tccatgtagg agcgttgggg tcaattcctc | 2204 |
| ccatgaggtc ttttaaaagc attgtctggc tgtagcttaa gcccacctga ggtggacctg | 2264 |
| ctgctccagg cgctggcctg ggtgaattga ctgcaggttt ctcgcttgtg agatcaattg | 2324 |
| ttgtgttttc ccatgctctc cccacaatcg atgttctaca agctatgtat ggccatcctt | 2384 |
| cacctgaaag gcaaacttta tagaggatgt tttcataagg gttcctgtcc ccaacttggt | 2444 |

```
ctgaaacaaa catgttgagt tttctcttgg ccccgagaac tgccttcaag aggtcctcgc    2504
tgttgcttgg cttgatcaaa attgactcta acatgttacc cccatccaac agggctgccc    2564
ctgccttcac ggcagcacca agactaaagt tatagccaga aatgttgatg ctggactgct    2624
gttcagtgat gaccoccaga actgggtgct tgtctttcag cctttcaaga tcattaagat    2684
ttggatactt gactgtgtaa agcaagccaa ggtctgtgag cgcttgtaca acgtcattga    2744
gcggagtctg tgactgtttg ccatacaag ccatagttag acttggcatt gtgccaaatt     2804
gattgttcaa aagtgatgag tctttcacat cccaaactct taccacacca cttgcaccct    2864
gctgaggctt tctcatccca actatctgta ggatctgaga tctttggtct agttgctgtg    2924
ttgttaagtt ccccatatat accctgaag cctggggcct ttcagacctc atgatcttgg     2984
ccttcagctt ctcaaggtca gccgcaagag acatcagttc ttctgcactg agcctcccca    3044
ctttcaaaac attcttcttt gatgttgact ttaaatccac aagagaatgt acagtctggt    3104
tgagacttct gagtctctgt aggtctttgt catctctctt ttccttcctc atgatcctct    3164
gaacattgct gacctcagag aagtccaacc cattcagaag gttggttgca tccttaatga    3224
cagcagcctt cacatctgat gtgaagctct gcaattctct tctcaatgct gcgtccatt     3284 ggaagctctt aacttcctta gacaaggaca tcttgttgct caatggtttc tcaagacaaa    3344
tgcgcaatca aatgcctagg atccactgtg cg                                  3376
```

<210> SEQ ID NO 8
<211> LENGTH: 498
<212> TYPE: PRT
<213> ORGANISM: Lymphocytic choriomeningitis virus

<400> SEQUENCE: 8

```
Met Gly Gln Ile Val Thr Met Phe Glu Ala Leu Pro His Ile Ile Asp
 1               5                  10                  15

Glu Val Ile Asn Ile Val Ile Ile Val Leu Ile Val Ile Thr Gly Ile
             20                  25                  30

Lys Ala Val Tyr Asn Phe Ala Thr Cys Gly Ile Phe Ala Leu Ile Ser
         35                  40                  45

Phe Leu Leu Leu Ala Gly Arg Ser Cys Gly Met Tyr Gly Leu Lys Gly
     50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Ala Asn Asn
                 85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Arg Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205
```

```
Gly Trp Thr Gly Ser Asp Gly Lys Thr Thr Trp Cys Ser Gln Thr Ser
    210                 215                 220
Tyr Gln Tyr Leu Ile Ile Gln Asn Arg Thr Trp Glu Asn His Cys Thr
225                 230                 235                 240
Tyr Ala Gly Pro Phe Gly Met Ser Arg Ile Leu Leu Ser Gln Glu Lys
                245                 250                 255
Thr Lys Phe Phe Thr Arg Arg Leu Ala Gly Thr Phe Thr Trp Thr Leu
            260                 265                 270
Ser Asp Ser Ser Gly Val Glu Asn Pro Gly Gly Tyr Cys Leu Thr Lys
        275                 280                 285
Trp Met Ile Leu Ala Ala Glu Leu Lys Cys Phe Gly Asn Thr Ala Val
    290                 295                 300
Ala Lys Cys Asn Val Asn His Asp Ala Glu Phe Cys Asp Met Leu Arg
305                 310                 315                 320
Leu Ile Asp Tyr Asn Lys Ala Ala Leu Ser Lys Phe Lys Glu Asp Val
                325                 330                 335
Glu Ser Ala Leu His Leu Phe Lys Thr Thr Val Asn Ser Leu Ile Ser
            340                 345                 350
Asp Gln Leu Leu Met Arg Asn His Leu Arg Asp Leu Met Gly Val Pro
        355                 360                 365
Tyr Cys Asn Tyr Ser Lys Phe Trp Tyr Leu Glu His Ala Lys Thr Gly
    370                 375                 380
Glu Thr Ser Val Pro Lys Cys Trp Leu Val Thr Asn Gly Ser Tyr Leu
385                 390                 395                 400
Asn Glu Thr His Phe Ser Asp Gln Ile Glu Gln Glu Ala Asp Asn Met
                405                 410                 415
Ile Thr Glu Met Leu Arg Lys Asp Tyr Ile Lys Arg Gln Gly Ser Thr
            420                 425                 430
Pro Leu Ala Leu Met Asp Leu Leu Met Phe Ser Thr Ser Ala Tyr Leu
        435                 440                 445
Val Ser Ile Phe Leu His Leu Val Lys Ile Pro Thr His Arg His Ile
    450                 455                 460
Lys Gly Gly Ser Cys Pro Lys Pro His Arg Leu Thr Asn Lys Gly Ile
465                 470                 475                 480
Cys Ser Cys Gly Ala Phe Lys Val Pro Gly Val Lys Thr Val Trp Lys
                485                 490                 495
Arg Arg

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Lys Ala Val Tyr Asn Phe Ala Thr Met
1               5

<210> SEQ ID NO 10
<211> LENGTH: 58
<212> TYPE: DNA
<213> ORGANISM: Artificial Sequence
<220> FEATURE:
<223> OTHER INFORMATION: Synthetic oligonucleotide
```

<400> SEQUENCE: 10
ccgggccaga atccatccat tcattctcga gaatgaatgg atggattctg gcttttttg    58

<210> SEQ ID NO 11
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 11
aattcaaaaa gccagaatcc atccattcat tctcgagaat gaatggatgg attctggc      58

<210> SEQ ID NO 12
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 12
ccgggcccga gtctgtgaat gtaatctcga gattacattc acagactcgg gcttttttg    58

<210> SEQ ID NO 13
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 13
aattcaaaaa gcccgagtct gtgaatgtaa tctcgagatt acattcacag actcgggc     58

<210> SEQ ID NO 14
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 14
ccgggccaaa ctgataatct cctcactcga gtgaggagat tatcagtttg gcttttttg    58

<210> SEQ ID NO 15
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 15
aattcaaaaa gccaaactga taatctcctc actcgagtga ggagattatc agtttggc     58

<210> SEQ ID NO 16
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 16
ccgggcatgg aacattgtga gaaatctcga gatttctcac aatgttccat gcttttttg    58

```
<210> SEQ ID NO 17
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 17
aattcaaaaa gcatggaaca ttgtgagaaa tctcgagatt tctcacaatg ttccatgc        58

<210> SEQ ID NO 18
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 18
ccggccgaag atagtgattg gttatctcga gataaccaat cactatcttc ggttttg         58

<210> SEQ ID NO 19
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 19
aattcaaaaa ccgaagatag tgattggtta tctcgagata accaatcact atcttcgg       58
```